US011242513B2

(12) United States Patent
Van Der Oost et al.

(10) Patent No.: US 11,242,513 B2
(45) Date of Patent: *Feb. 8, 2022

(54) THERMOSTABLE CAS9 NUCLEASES

(71) Applicants: Wageningen Universiteit, Wageningen (NL); Stichting Voor De Technische Wetenschappen, Utrecht (NL)

(72) Inventors: John Van Der Oost, Renkum (NL); Richard Van Kranenburg, Gorinchem (NL); Elleke Fenna Bosma, Denmark (NL); Ioannis Mougiakos, Wageningen (NL)

(73) Assignees: Wageningen Universiteit, Wageningen (NL); Stichting Voor De Technische Wetenschappen, Utrecht (NL)

(*) Notice: Subject to any disclaimer, the term of this patent is extended or adjusted under 35 U.S.C. 154(b) by 366 days.

This patent is subject to a terminal disclaimer.

(21) Appl. No.: 16/469,674

(22) PCT Filed: Dec. 14, 2016

(86) PCT No.: PCT/EP2016/081077
§ 371 (c)(1),
(2) Date: Jun. 14, 2019

(87) PCT Pub. No.: WO2018/108272
PCT Pub. Date: Jun. 21, 2018

(65) Prior Publication Data
US 2019/0367893 A1 Dec. 5, 2019

(51) Int. Cl.
C12N 9/22 (2006.01)
C12N 15/90 (2006.01)
C12N 15/11 (2006.01)
C12N 15/113 (2010.01)
C12N 15/63 (2006.01)

(52) U.S. Cl.
CPC .............. *C12N 9/22* (2013.01); *C12N 15/11* (2013.01); *C12N 15/907* (2013.01); *C12N 2310/20* (2017.05)

(58) Field of Classification Search
None
See application file for complete search history.

(56) References Cited

U.S. PATENT DOCUMENTS

2016/0139124 A1  5/2016  Newman

FOREIGN PATENT DOCUMENTS

| JP | 2006230303 | | 9/2006 |
|---|---|---|---|
| JP | 2007537724 | A | 12/2007 |
| JP | 2010510776 | A | 4/2010 |
| WO | 2005084409 | | 9/2005 |
| WO | 2008066280 | | 6/2008 |
| WO | 2014144951 | | 9/2014 |
| WO | 2015139008 | | 9/2015 |
| WO | 2016073990 | | 5/2016 |
| WO | 2016179038 | A1 | 11/2016 |
| WO | 2016186946 | A1 | 11/2016 |
| WO | 2016198361 | A1 | 12/2016 |
| WO | 2018108272 | A1 | 6/2018 |

OTHER PUBLICATIONS

Uniprot Accession No. A0A178TEJ9_GEOSE dated Sep. 7, 2016, retrieved from the Internet: <<https://www.uniprot.org/uniprot/A0A178TEJ9>>, retrieved on Aug. 31, 2021.*
Harrington et al.,"A thermostable Cas9 with increased lifetime in human plasma," Nat Commun. 2017; 8: 1424, 26 pages.
Mougiakos et al., "Next Generation Prokaryotic Engineering: The CRISPR-Cas Toolkit," Trends Biotechnol. Jul. 2016;34(7):575-587.
Mougiakos et al., "Efficient Genome Editing of a Facultative Thermophile Using Mesophilic spCas9," ACS Synth Biol. May 19, 2017;6(5):849-861.
Blenke et al., CRISPR-Cas9 gene editing: Delivery aspects and therapeutic potential, J Control Release. Dec. 28, 2016;244(Pt B):139-148.
"RecName: Full=CRISPR-associated endonuclease Cas9 {ECO:0000256|HAMAP-Rule:MF_01480}; EC=3.1.-.- {ECO:0000256|HAMAP-Rule:MF_01480};", UniProt,(Sep. 7, 2016), Database accession No. A0A178TEJ9, URL: EBI, XP002773239, 2 pages.
Mougiakos Ioannis et al, "Characterizing a thermostable Cas9 for bacterial genome editing and silencing.", Nature Communications, (Nov. 21, 2017), vol. 8, No. 1, doi:10.1038/s41467-017-01591-4, ISSN 2041-1723, pp. 1-11, XP002779888.
Written Opinion in App. No. SG11201905380U, dated Oct. 5, 2020, 6 pages.
Written Opinion in App. No. SG11201905381X, dated Oct. 3, 2020, 7 pages.
Written Opinion in App. No. SG11201905383Y, dated Sep. 28, 2020, 7 pages.
Written Opinion in App. No. SG11201905378P, dated Oct. 5, 2020, 7 pages.

(Continued)

*Primary Examiner* — Suzanne M Noakes
*Assistant Examiner* — Jae W Lee
(74) *Attorney, Agent, or Firm* — Riverside Law LLP

(57) ABSTRACT

The present invention relates to the field of genetic engineering and more particularly to nucleic acid editing and genome modification. The present invention provides an isolated Cas protein or polypeptide fragment thereof having an amino acid sequence of SEQ ID NO: 1 or a sequence of at least 77% identity therewith. The Cas protein or polypeptide is capable of binding, cleaving, marking or modifying a double stranded target polynucleotide at a temperature in the range 30° C. and 100° C. inclusive. The invention further provides isolated nucleic acid molecules encoding the Cas9 nucleases, expression vectors and host cells. The invention also provides PAM sequences recognized by the Cas protein or polypeptide, The Cas9 nucleases disclosed herein provide novel tools for genetic engineering at elevated temperatures and are of particular value in the genetic manipulation of thermophilic organisms; particularly microorganisms.

20 Claims, 16 Drawing Sheets
Specification includes a Sequence Listing.

(56) References Cited

OTHER PUBLICATIONS

Daas et al., 2016, "Isolation of a genetically accessible thermophilic xylan degrading bacterium from compost." Biotechnol Biofuels, 9:210.
Karvelis et al., (2015) "Rapid characterization of CRISPR-Cas9 protospacer adjacent motif sequence elements," Genome Biology 16:253.
Leenay et al., 2016, "Identifying and Visualizing Functional PAM Diversity across CRISPR-Cas Systems," Molecular Cell, 62(1):137-147.
Notice of Allowance dated Sep. 24, 2021 for U.S. Appl. No. 16/469,677 (pp. 1-17).
Translation of JP2006230303A "Thermophilic lipase producing bacterium and use thereof".
Corrected Notice of Allowability dated Nov. 22, 2021 for U.S. Appl. No. 16/469,677 (pp. 1-2).
CRISPR-associated endonuclease Cas9 [Geobacillus stearothermophilus] GenBank: KZE96909.1.

* cited by examiner

Figure 6

```
tracrRNA t12    1   atgtttcccctcccatgcacaatagtttatagtaaaaagacctgacgttccgccaaggtcttc
repeat gb           |||||||||||||||||||||||||||||||||||||||||||||||||||||||||||||||| tracrRNA t12    71  gtcgcctaagagtggggaatgccgaagaaagcggcgatagccacgcgccacggtcagtct
repeat gb           |||||||||||||||||||||||||||||||||||||||||||||||||||||||||||||||| tracrRNA t12    141 gcctataggcagaaagccctatcatagtaacctgagatcatgctgtggtataacctattactataa
repeat gb       1   -----------------------gtcatagttccctgagattatcgctggttgtataat----- tracrRNA t12    211 taatgtttatattggaaaatcaagtcctttctatatatttttcattctcttgcattat
repeat gb           |||||||||||||||||||||||||||||||||||||||||||||||||||||||| tracrRNA t12    281 gatgatgtgagggaggatagattctgacaggaggtttccacatcg   (SEQ ID NO:23)
repeat gb                                                         (SEQ ID NO:24)
```

Figure 7

1. Match to: DQ453159 DQ453159 Geobacillus virus E2, complete genome(DQ453159) position: 39980-39921, with: spacer4 CRISPR No.4 Spacer No.1 (spacer4_4_1) position: 1-30, Strand: +

(SEQ ID NO:25) — CRISPR spacer RNA
(SEQ ID NO:26) — Protospacer Sequence
(SEQ ID NO:27) — Entrez Nucleotide Score: 30

2. Match to: Bacillus alveayensis strain 24KAM51 LG50_053, whole genome shotgun sequence(NZ_JYCT01000053) position: 110818-110859, with: spacer9 CRISPR No.9 Spacer No.1 (spacer9_9_1) position: 1-30, Strand: +

(SEQ ID NO:28) — CRISPR spacer RNA
(SEQ ID NO:29) — Protospacer Sequence
(SEQ ID NO:30) — Entrez Nucleotide Score: 30

3. Match to: Anoxybacillus flavithermus WK1, complete genome(CP000922) position: 701422-701450, with: spacer5 CRISPR No.5 Spacer No.1 (spacer5_5_1) position: 1-29, Strand: -

(SEQ ID NO:31) — CRISPR spacer RNA
(SEQ ID NO:32) — Protospacer Sequence
(SEQ ID NO:33) — Entrez Nucleotide Score: 29

4. Match to: Geobacillus kaustophilus strain E323 LG51_086, whole genome shotgun sequence(NZ_JYCT01000086) position: 15565-15537, with: spacer5 CRISPR No.5 Spacer No.1 (spacer5_5_1) position: 1-29, Strand: +

(SEQ ID NO:34) — CRISPR spacer RNA
(SEQ ID NO:35) — Protospacer Sequence

Figure 7 (continued)

(SEQ ID NO:36) 5' [sequence] 3'    <- Entrez Nucleotide

Score: 29

5. Match to: DQ453159 DQ453159 Geobacillus virus E2, complete genome(DQ453159) position: 6492-6461, with: spacer6 CRISPR No.6 Spacer No.1 (spacer6_6_1) position: 1-30, Strand: +

(SEQ ID NO:37) 5' [sequence] CAACACCTTCCSCGCTGTCCGTCTACTGT [sequence] 3'    <- CRISPR spacer RNA (SEQ ID NO:38) 3' [sequence] TTGTGGAAGGCACCACAGACTAGATGAAA [sequence] 5'    <- Protospacer Sequence (SEQ ID NO:39) 5' [sequence] CAACACCTTCCGTGCTGTCTCATCTACTTT [sequence] 3'    <- (Entrez Nucleotide)

Score: 26

6. Match to: Pasteurella bettyae CCTG 2042 contig00003, whole genome shotgun sequence(NZ_AJSX01000041) position: 137780-137809, with: spacer7 CRISPR No.7 Spacer No.1 (spacer7_7_1) position: 1-30, Strand: -

(SEQ ID NO:40) 5' [sequence] 3'    <- CRISPR spacer RNA (SEQ ID NO:41) 3' [sequence] AACTAATCGTTAAACTGACGCCTTAAATCA [sequence] 5'    <- Protospacer Sequence (SEQ ID NO:42) 5' [sequence] TTGATTAGCAATTTGACTGCGGAATTTAGT [sequence] 3'    <- (Entrez Nucleotide)

Colonies are indicated with arrows.

THERMOSTABLE CAS9 NUCLEASES

CROSS-REFERENCE TO RELATED APPLICATIONS

This application is a U.S. national phase application filed under 35 U.S.C. § 371 claiming priority to International Patent Application No. PCT/EP16/081077, filed Dec. 14, 2016, the contents of each of which are incorporated by reference herein in their entireties.

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file: "206071-0012-00US_SubstituteSequenceListing.txt"; created on Sep. 9, 2021, and 42,325 bytes in size, is hereby incorporated by reference.

FIELD OF THE INVENTION

The present invention relates to the field of genetic engineering and more particularly to nucleic acid editing and genome modification. The present invention concerns genetic engineering tools in the form of nucleases which can be configured for sequence-directed site-specific binding, nicking, cutting and modification of genetic material; also ribonucleoproteins which exert activity, particularly nuclease activity, on sequence specific sites of genetic material, and modified nucleases and ribonucleoproteins for use as markers. The invention therefore also concerns associated expression constructs for delivery and expression of nucleases and guide RNAs within cells. Further, the invention concerns the sequence-specific editing of nucleic acids in vitro or in vivo and methods used to achieve that. A particular area to which the invention relates is the genetic manipulation of thermophilic organisms, particularly microorganisms.

BACKGROUND TO THE INVENTION

It was first demonstrated in 2007 that CRISPR-Cas is an adaptive immune system in many bacteria and most archaea (Barrangou et al., 2007, Science 315: 1709-1712), Brouns et al., 2008, Science 321: 960-964). Based on functional and structural criteria, three types of CRISPR-Cas systems have so far been characterized, most of which use small RNA molecules as guide to target complementary DNA sequences (Makarova et al., 2011, Nat Rev Microbiol 9: 467-477; Van der Oost et al., 2014, Nat Rev Microbiol 12: 479-492).

In a recent study by the Doudna/Charpentier labs, a thorough characterization of the effector enzyme of the type II CRISPR-Cas system (Cas9) was performed, including demonstration that the introduction of designed CRISPR RNA guides (with specific spacer sequences) targets complementary sequences (protospacers) on a plasmid, causing double strand breaks of this plasmid (Jinek et al., 2012, Science 337: 816-821). Following Jinek et al., 2012, Cas9 is used as a tool for genome editing.

Cas9 has been used to engineer the genomes of a range of eukaryotic cells (e.g. fish, plant, man) (Charpentier and Doudna, 2013, Nature 495: 50-51).

In addition, Cas9 has been used to improve yields of homologous recombination in bacteria by selecting for dedicated recombination events (Jiang et al., 2013, Nature Biotechnol 31: 233-239). To achieve this, a toxic fragment (Targeting construct) is co-transfected with a rescuing fragment carrying the desired alteration (Editing construct, carrying point mutation or deletions). The Targeting construct consists of Cas9 in combination with a design CRISPR and an antibiotic resistance marker, defining the site of the desired recombination on the host chromosome; in the presence of the corresponding antibiotic, integration of the Targeting construct in the host chromosome is selected for. Only when the additional recombination occurs of the Editing construct with the CRISPR target site on the host chromosome, the host can escape from the auto-immunity problem. Hence, in the presence of the antibiotic, only the desired (marker-free) mutants are able to survive and grow. A related strategy to select for subsequent removal of the integrated Targeting construct from the chromosome is presented as well, generating a genuine marker free mutant.

It has been established in recent years that CRISPR-Cas mediated genome editing constitutes a useful tool for genetic engineering. It has been established that the prokaryotic CRISPR systems serve their hosts as adaptive immune systems (Jinek et al., 2012, Science 337: 816-821) and can be used for quick and effective genetic engineering (Mali et al., 2013, Nat Methods 10:957-963, for example), requiring only modification of the guide sequence in order to target sequences of interest.

However, there is a continuing need for the development of agents with improved sequence-specific nucleic acid detection, cleavage and manipulation under a variety of experimental conditions for application in the area of genetic research and genome editing. In particular, currently available sequence-specific genome editing tools, including Cas9, are not applicable for use in all conditions or organisms, for example, sequence-specific nucleases are relatively thermo-sensitive and therefore not applicable for use in strictly thermophilic microorganisms (which are capable of growth between 41° C. and 122° C. and grow optimally in the ranges of temperatures from >45° C. to 80° C. with hyperthermophiles capable of optimal growth above 80° C.), for example, microorganisms that are used in industrial fermentations or for in vitro laboratory processes conducted at elevated temperatures.

To date there is no experimental evidence for active Cas9 proteins in thermophiles. Based on a comparative genome screening by Chylinski et al. (2014; Nucleic Acids Research 42: 6091-61-05) on the presence of Cas9 in bacteria it was found that the Type II-C CRISPR-Cas system is only present in approximately 3.3% of all bacterial genomes. Among thermophilic bacteria, the Type II system is underrepresented based on statistical analysis (P=0.0019). In addition, no Type II system has been found in archaea however, this could possibly be due to the absence of the RNase III protein (involved in the Type II system) in archaea. Chylinski, et al., (2014; Nucleic Acids Research 42: 6091-6105) did describe the classification and evolution of type II CRISPR-Cas systems, in particular, two species are identified which exhibit these systems, however these species grow maximally at 55° C. and do not exhibit strictly thermophilic growth with optimum growth temperature 60-80° C., with hyperthermophiles capable of growing optimally above 80° C.

Despite the rarity of the CRISPR-Cas system in bacterial genomes and in particular the fact that Cas9 has been found only in bacteria (not archaea) with optimal growth temperatures below 45° C., the inventors have surprisingly discovered several thermostable Cas9 variants which enable genome editing to be carried out at elevated temperatures.

The inventors have also discovered optimised protospacer adjacent motif (PAM) sequences that work with the thermostable Cas9 variants to enable genome editing to be carried out over a wide range of temperatures, including at the elevated temperatures. These Cas9 nucleases, and RNA molecules that are designed with knowledge of the associated PAM sequences, provide novel tools for genetic engineering at elevated temperatures and are of particular value in the genetic manipulation of thermophilic organisms; particularly microorganisms.

SUMMARY OF THE INVENTION

Accordingly, the present invention provides an isolated clustered regularly interspaced short palindromic repeat (CRISPR)-associated (Cas) protein or polypeptide comprising;
a. the amino acid motif EKDGKYYC [SEQ ID NO: 2]; and/or
b. the amino acid motif $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and/or
c. the amino acid motif $X_5LKX_6IE$ [SEQ ID NO: 4] wherein $X_5$ is independently selected from Methionine or Phenylalanine and $X_6$ is independently selected from Histidine or Asparagine; and/or
d. the amino acid motif $X_7VYSX_8K$ [SEQ ID NO: 5] wherein $X_7$ is Glutamate or Isoleucine and $X_8$ is one of Tryptophan, Serine or Lysine; and/or
e. the amino acid motif $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

A polypeptide in the context of this invention may be viewed as a fragment of the full length Cas protein. Such fragments may be inactive and used in ways and for purposes not associated directly with binding, editing and/or cutting of genetic material, for example for standards in assays or raising antibodies or the like.

In preferred embodiments however, the Cas protein or polypeptide is functional and capable of cleavage, binding, marking or modifying at a temperature in the range 20° C. and 100° C., inclusive, when associated with at least one targeting RNA molecule, and a polynucleotide comprising a target nucleic acid sequence recognised by the targeting RNA molecule. Preferably the Cas protein or polypeptide is functional and capable of said cleavage, binding, marking or modifying at a temperature in the range 50° C. and 70° C., for example 55° C. or 60° C.

In particular embodiments, the invention may provide a Cas protein or polypeptide comprising the amino acid motif EKDGKYYC [SEQ ID NO: 2]. In other embodiments, the Cas proteins or polypeptides may further comprise the amino acid motif $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine.

In other embodiments the Cas proteins or polypeptides defined herein may additionally further comprise the amino acid motif $X_5LKX_6IE$ [SEQ ID NO: 4] wherein $X_5$ is independently selected from Methionine or Phenylalanine and $X_6$ is independently selected from Histidine or Asparagine.

In other embodiments, the Cas proteins or polypeptides defined herein may additionally further comprise the amino acid motif $X_7VYSX_8K$ [SEQ ID NO: 5] wherein $X_7$ is Glutamate or Isoleucine and $X_8$ is one of Tryptophan, Serine or Lysine.

In other embodiments, the Cas proteins or polypeptides defined herein may additionally further comprise the amino acid motif $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

In accordance with the present invention, it may be appreciated that a Cas protein or polypeptide of the invention may comprise any of the motifs of SEQ ID NOs 2 to 6, either alone or in combination. The following summarises each of the combinations of motifs which may characterize Cas proteins or polypeptides of the invention:

[SEQ ID NO: 2]
EKDGKYYC.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine; and $X_9FYX_1X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_7VYSX_8K$ [SEQ ID NO: 5] wherein $X_7$ is Glutamate or Isoleucine and $X_8$ is one of Tryptophan, Serine or Lysine; and $X_9FYX_1X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_5LKX_6IE$ [SEQ ID NO: 4] wherein $X_5$ is independently selected from Methionine or Phenylalanine and $X_6$ is independently selected from Histidine or Asparagine.

EKDGKYYC [SEQ ID NO: 2]; and $X_7VYSX_8K$ [SEQ ID NO: 5] wherein $X_7$ is Glutamate or Isoleucine and $X_8$ is one of Tryptophan, Serine or Lysine.

EKDGKYYC [SEQ ID NO: 2]; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine.

EKDGKYYC [SEQ ID NO: 2]; and $X_5LKX_6IE$ [SEQ ID NO: 4] wherein $X_5$ is independently selected from Methionine or Phenylalanine and $X_6$ is independently selected from Histidine or Asparagine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_7VYSX_8K$ [SEQ ID NO: 5] wherein $X_7$ is Glutamate or Isoleucine and $X_8$ is one of Tryptophan, Serine or Lysine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine.

$X_5LKX_6IE$ [SEQ ID NO: 4] wherein $X_5$ is independently selected from Methionine or Phenylalanine and $X_6$ is independently selected from Histidine or Asparagine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

In another aspect, the present invention provides an isolated Cas protein or polypeptide fragment thereof having an amino acid sequence of SEQ ID NO: 1 or a sequence of at least 77% identity therewith. Preferably the Cas protein or polypeptide is capable of binding, cleavage, marking or modifying at a temperature in the range 20° C. and 100° C. inclusive. Preferably the Cas protein or polypeptide is capable of said cleavage, binding, marking or modifying at a temperature in the range between 50° C. and 70° C., for example 55° C. or 60° C. Preferably the Cas protein or polypeptide is capable of said cleavage, binding, marking or modifying at a temperature in the range between 300° C. and 80° C., at a temperature between 37° C. and 78° C., preferably at a temperature above 55° C.; more preferably at a temperature between 55° C. and 80° C.; even more preferably at a temperature between 55° C. and 65° C. or 60° C. and 65° C.

The present invention also provides uses of a targeting RNA molecule and a Cas protein or polypeptide provided herein, for binding, cleaving, marking or modifying a target polynucleotide comprising a target nucleic acid sequence. The targeting RNA molecule recognizes the target nucleic acid sequence on a target nucleic acid strand of the polynucleotide.

The target polynucleotide that comprises the target nucleic acid sequence may be double stranded and so comprise a target nucleic acid strand, comprising said target nucleic acid sequence, and a non-target nucleic acid strand, comprising a protospacer nucleic acid sequence. The protospacer nucleic acid sequence is substantially complementary to the target nucleic acid sequence and pairs with it in the double stranded target polynucleotide. The non-target nucleic acid strand may further comprise a protospacer adjacent motif (PAM) sequence directly adjacent the 3' end of the protospacer sequence. The PAM sequence may be at least 6, 7, or 8 nucleic acids in length. Preferably, the PAM sequence has a cytosine in the fifth position. Preferably the PAM sequence comprises the sequence 5'-NNNNC-3', so that from the 5'-end the PAM sequence begins 5'-NNNNC-3'. Additionally or alternatively, the PAM sequence may have an adenine in the eighth position, so that the PAM sequence comprises the sequence 5'-NNNNNNNA-3', and from the 5'-end the PAM sequence begins 5'-NNNNNNNA-3'. Additionally or alternatively, the PAM sequence may have a cytosine in one or more of the first, second, third, fourth, and sixth positions, such that from the 5'-end the PAM sequence begins 5'-CNNNN-3', 5'-NCNNN-3', 5'-NNCNN-3', 5'-NNNCN-3', and/or 5'-NNNNNC-3'. Preferably the PAM sequence comprises, so that from the 5'-end the PAM sequence begins, 5'-CCCCCCNA-3' [SEQ ID NO: 10], and further preferably the PAM sequence comprises, so that from the 5'-end the PAM sequence begins, 5'-CCCCCCAA-3' [SEQ ID NO: 11]. Other preferred PAM sequences include 5'-ATCCCCAA-3' [SEQ ID NO: 21] and 5'-ACGGCCAA-3' [SEQ ID NO: 22].

Preferably, the Cas protein or polypeptide is capable of the binding, cleaving, marking or modifying at a temperature in the range 40° C. to 800° C. inclusive, preferably in the range 45° C. to 800° C. inclusive, and further preferably in the range 50° C. to 800° C. inclusive. For example, the binding, cleaving, marking or modifying occurs at a temperature of 45° C., 46° C., 47° C., 480° C., 49° C., 50° C., 51° C., 52° C., 53° C., 54° C., 55° C., 56° C., 57° C., 58° C., 59° C., 600° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C. or 800° C. More preferably the Cas protein or polypeptide is capable of the binding, cleaving, marking or modifying at a temperature in the range 55 to 65° C. In preferred aspects, a Cas protein or polypeptide fragment of the invention may comprises an amino acid sequence of at least 75% identity; preferably at least 85%; more preferably at least 90%; even more preferably at least 95% identity to SEQ ID NO: 1.

The Cas protein or polypeptide may be used in combination with a targeting RNA molecule that recognizes a target nucleic acid sequence on the target nucleic acid strand, where the non-target nucleic acid sequence has a PAM sequence directly adjacent the 3' end of the protospacer sequence on the non-target strand, as disclosed herein. Thus, the PAM sequence may comprise the sequence 5'-NNNNC-3', and the Cas protein may bind, cleave, mark or modify the target strand at a temperature in the range 20° C. and 100° C. inclusive, preferably in the range 30° C. and 90° C. inclusive, in the range 37° C. and 78° C. inclusive, in the range 40° C. and 80° C. inclusive, in the range 50° C. and 70° C. inclusive, or in the range 55° C. and 65° C., inclusive. Preferably from the 5'-end the PAM sequence begins 5'-NNNNC-3' and the Cas protein may bind, cleave, mark or modify the target strand at a temperature in the range 20° C. and 100° C. inclusive, preferably in the range 30° C. and 90° C. inclusive, in the range 37° C. and 78° C. inclusive, in the range 40° C. and 80° C. inclusive, in the range 50° C. and 70° C. inclusive, or in the range 55° C. and 65° C., inclusive. Preferably from the 5'-end the PAM sequence begins 5'-NNNNNNNA-3' and the Cas protein may bind, cleave, mark or modify the target strand at a temperature in the range 20° C. and 100° C. inclusive, preferably in the range 30° C. and 90° C. inclusive, in the range 37° C. and 78° C. inclusive, in the range 40° C. and 80° C. inclusive, the range 550° C. and 70° C. inclusive, or in the range 55° C. and 65° C., inclusive. Further preferably the 5'-end of the PAM sequence begins 5'-NNNNCNNA-3' and the Cas protein may bind, cleave, mark or modify the target strand at a temperature in the range 20° C. and 100° C. inclusive, preferably in the range 30° C. and 90° C. inclusive, in the range 37° C. and 78° C. inclusive, in the range 40° C. and 80° C. inclusive, in the range 50° C. and 70° C. inclusive, or in the range 55° C. and 65° C., inclusive.

More particularly, a Cas protein or polypeptide of the invention may comprise an amino acid sequence with a percentage identity with SEQ ID NO:1 as follows: at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5% or at least 99.8%. The percentage identity may be at least 89%. The percentage identity may be at least 90%. Preferably the percentage identity will be at least 95%, for example 98%.

The percentage amino acid sequence identity with SEQ ID NO: 1 is determinable as a function of the number of identical positions shared by the sequences in a selected comparison window, taking into account the number of gaps, and the length of each gap, which need to be introduced for optimal alignment of the two sequences.

A Cas protein or polypeptide fragment of the invention may be characterised in terms of both the reference sequence SEQ ID NO: 1 and any aforementioned percentage variant thereof as defined by percentage sequence identity, alone or in combination with any of the aforementioned amino acid motifs (i.e. SEQ ID NOS 2 and/or 3 and/or 4 and/or 5 and/or 6) as essential features.

The invention provides a use of a targeting RNA molecule as provided herein and a Cas protein or polypeptide of the invention for binding, cleaving, marking or modifying a target nucleic acid strand comprising a target nucleic acid sequence. Preferably said binding, cleaving, marking or modifying occurs at a temperature disclosed herein, for example at a temperature of between 20 and 100° C. The invention also provides a method of binding, cleaving, marking or modifying a target nucleic acid sequence in a target nucleic acid strand comprising designing a targeting RNA molecule as provided herein and forming a ribonucleoprotein complex comprising the targeting RNA molecule and a Cas protein or polypeptide of the invention. Preferably the ribonucleoprotein complex binding, cleaving, marking or modifying the target nucleic acid sequence at a temperature disclosed herein, for example at a temperature of between 37 and 100° C.

The uses and methods of the invention may be carried out, and the nucleoproteins of the invention formed and used, in vivo, for example in bacterial cells. Alternatively the uses and methods of the invention may be carried out, and the nucleoproteins of the invention formed and used, in vitro. The Cas protein of the invention may be provided in isolated form, for example when used in vitro or when added to cells by transfection, the Cas protein may be heterologously expressed, for example following transient or stable transformation of the cell by nucleic acid encoding the Cas protein, the targeting RNA molecule may be transcribed from an expression vector following transient or stable transformation of the cell by nucleic acid encoding the RNA molecule, and/or the RNA molecule may be provided in isolated form, for example when used in vitro or when added to cells by transfection. In preferred embodiments, the Cas protein or polypeptide is expressed from the genome of a host cell, following stable intergration of a nucleic acid encoding the Cas protein or polypeptide in the genome of the host cell. Thus the Cas protein and/or RNA molecule may be added to the in vivo or in vitro environment using any artificial or contrived method for adding a protein or nucleic acid molecule to a cell in which it is not otherwise present.

The polynucleotide comprising the target nucleic acid sequence may be cleaved by the Cas protein, and optionally the cleavage may be DNA cleavage. The target nucleic acid strand comprising the target sequence may be double stranded DNA and the method or use may result in a double stranded break in the polynucleotide comprising the target nucleic acid sequence. The polynucleotide comprising the target nucleic acid sequence may be double stranded DNA, the Cas protein may lack the ability to cut the double stranded DNA and the use or method may result in gene silencing of the polynucleotide.

The Cas protein or polypeptide may be provided for the methods, uses and nucleoproteins of the invention at a concentration of 250 nM or less, for example at a concentration of 200 nM or less, 150 nM or less, 100 nM or less, 50 nM or less, 25 nM or less, 10 nM or less, 5 nM or less, 1 nM or less or 0.5 nM or less. Alternatively, the Cas protein or polypeptide may be provided at a concentration of at least 0.5 nM, at least 1 nM, at least 5 nM, at least 10 nM, at least 25 nM, at least 50 nM, at least 100 nM, at least 150 nM, at least 200 nM, or at least 250 nM. The PAM sequence of the invention may have an adenine in the eighth position, so that the PAM sequence comprises the sequence 5'-NNNNNNNA-3', and the concentration of Cas protein or polypeptide may be 100 nM or less, 50 nM or less, 25 nM or less, 10 nM or less, 5 nM or less, nM or less or 0.5 nM or less. The PAM sequence may comprise the sequence 5'-NNNNCNNA-3', and the concentration of Cas protein or polypeptide may be 100 nM or less, 50 nM or less, 25 nM or less, 10 nM or less, 5 nM or less, 1 nM or less or 0.5 nM or less. The PAM sequence may comprise the sequence 5'-CCCCCCNA-3' [SEQ ID NO: 10], and the concentration of Cas protein or polypeptide may be 100 nM or less, 50 nM or less, 25 nM or less, 10 nM or less, 5 nM or less, 1 nM or less or 0.5 nM or less.

Also, the invention provides nucleic acids encoding any of the aforementioned proteins or polypeptides of the invention. The nucleic acids may be isolated or in the form of expression constructs.

In all aforementioned aspects of the present invention, amino acid residues may be substituted conservatively or non-conservatively. Conservative amino acid substitutions refer to those where amino acid residues are substituted for other amino acid residues with similar chemical properties (e.g., charge or hydrophobicity) and therefore do not alter the functional properties of the resulting polypeptide.

Similarly it will be appreciated by a person of average skill in the art that nucleic acid sequences may be substituted conservatively or non-conservatively without affecting the function of the polypeptide. Conservatively modified nucleic acids are those substituted for nucleic acids which encode identical or functionally identical variants of the amino acid sequences. It will be appreciated by the skilled reader that each codon in a nucleic acid (except AUG and UGG; typically the only codons for methionine or tryptophan, respectively) can be modified to yield a functionally identical molecule. Accordingly, each silent variation (i.e. synonymous codon) of a polynucleotide or polypeptide, which encodes a polypeptide of the present invention, is implicit in each described polypeptide sequence.

The invention provides a transformed cell, having a target nucleic acid sequence in a double stranded target polynucleotide, said cell comprising a Cas protein or polypeptide as provided herein and at least one targeting RNA molecule as provided herein, and an expression vector comprising a nucleic acid encoding at least one of said Cas protein and said targeting RNA molecule. The Cas protein and targeting RNA molecule may enable or permit binding, cleaving, marking or modifying of the target sequence to occur in the transformed cell at a raised temperature, or at a range of temperatures, for example between 37 and 100° C., as disclosed herein. The invention further provides a method of binding, cleaving, marking or modifying a target nucleic acid in a cell comprising either 1) transforming, transfecting or transducing the cell with an expression vector comprising a nucleotide sequence encoding a Cas protein or polypeptide of the invention and a nucleotide sequence encoding a targeting RNA molecule of the invention; or 2) transforming, transfecting or transducing the cell with an expression vector comprising a nucleotide sequence encoding a Cas protein or polypeptide of the invention and a further expression vector comprising a nucleotide sequence encoding a targeting RNA molecule of the invention; or 3) transforming, transfecting or transducing the cell with an expression vector comprising a nucleotide sequence encoding a Cas protein or polypeptide of the invention, and delivering a targeting RNA molecule as provided herein to, or into the cell. The Cas protein or polypeptide may be expressed from the genome of the transformed cell, for example following stable integration into the genome of a nucleotide sequence encoding the Cas protein or polypeptide.

The invention also provides kits comprising one or more of the reagents for carrying out the uses and methods of the invention, or for generating the transformed cells or nucleoprotein complex of the invention, said kits including: a Cas protein or polypeptide of the invention or an expression vector comprising a nucleic acid sequence encoding a Cas protein or polypeptide of the invention; and/or a targeting RNA molecule of the invention or an expression vector comprising a nucleic acid sequence encoding a targeting RNA molecule of the invention. The kits may further include instructions for carrying out the invention, for example instructions for how to design a targeting RNA molecule in accordance with the invention.

RNA Guides and Target Sequences

Cas proteins of the invention allow for sequence-specific binding, cleavage, tagging, marking or modification of target nucleic acids at elevated temperatures. Target nucleic acids may be DNA (single-stranded or double-stranded), RNA or synthetic nucleic acids. A particularly useful application of the present invention is the sequence-specific targeting and modification of genomic DNA by one or more Cas proteins of the invention in complex with one or more guide RNAs (gRNAs) that complementarily bind to a targeted sequence of the genomic DNA. Consequently, the target nucleic acid is preferably double-stranded DNA. Such targeting may be performed in vitro or in vivo. Preferably such targeting is performed in vivo. In this way, Cas proteins of the invention may be used to target and modify specific DNA sequences located in the genomic DNA of a cell. It is envisaged that the Cas system may be used to modify genomes in a variety of cell types of and/or in different organisms.

The gRNAs, also called targeting RNA molecules, recognize the target nucleic acid sequence on the polynucleotide target strand. The RNA molecules may be designed to recognize a target sequence in a double stranded target polynucleotide, wherein the non-target strand comprises a protospacer adjacent motif (PAM) sequence directly adjacent the 3' end of the protospacer sequence. Disclosed herein are PAM sequences that work in an optimal manner with the Cas proteins and polypeptides of the invention. With knowledge of these PAM sequences, gRNAs may be designed for use with the Cas proteins and polypeptides of the invention across the temperature ranges and increased temperatures of the invention.

Accordingly, the present invention provides a ribonucleoprotein complex comprising a Cas protein or a polypeptide of the invention as hereinbefore described, and further comprising at least one RNA molecule which has a targeting function in that it recognizes a particular nucleotide sequence in a target polynucleotide. The present invention also provides use of at least one targeting RNA molecule and a Cas protein or polypeptide for binding, cleaving, marking or modifying a target nucleic acid strand, and a method of binding, cleaving, marking or modifying a target nucleic acid sequence in a target nucleic acid strand using a ribonucleoprotein or nucleoprotein of the invention, as well as transformed cells having the Cas protein or polypeptide and targeting RNA molecule. The target polynucleotide may further comprise a defined PAM sequence directly adjacent the 3' end of a protospacer sequence, in accordance with a PAM sequence provided herein. The PAM sequence may be 6, 7, or 8 nucleic acids in length, or longer, preferably 8 nucleic acids in length. Preferably, the RNA molecule is a single-stranded RNA molecule, e.g. a CRISPR RNA (crRNA) and is associated, e.g. by hybridization with a tracrRNA. The targeting RNA may be a chimera of a crRNA and tracrRNA. The aforementioned RNA molecules may have a ribonucleotide sequence of at least 90% identity, or complementarity to a target nucleotide sequence. Optionally, the RNA molecule has a ribonucleotide sequence of at least 90%, at least 91%, at least 92%, at least 93%, at least 94%, at least 95%, at least 96%, at least 97%, at least 98%, at least 99% or 100% identity or complementarity to a target nucleotide sequence. The preferred target nucleotide sequence is a DNA.

In a preferred aspect, the present invention provides a ribonucleoprotein complex as hereinbefore described, wherein the at least one targeting RNA molecule is substantially complementary along its length to a target DNA sequence.

The targeting RNA molecule may be bound to or associated with the target sequence within the nucleoprotein complex, so that the target polynucleotide, comprising the target sequence and PAM sequence on the non-target strand, may be associated with and so form part of a nucleoprotein complex of the invention.

Alteration of the sequence of the RNA guide which associates with the Cas protein of the invention therefore allows the Cas protein to be programmed to mark or cut double-stranded DNA at sites complementary to the guide RNA.

Preferably, the length of the at least one targeting RNA molecule in a ribonucleoprotein complex of the invention is in the range 35 to 135 residues, optionally in the range 35 to 134 residues, 35 to 133 residues, 35 to 132 residues, 35 to 131 residues, 35 to 130 residues, 35 to 129 residues, 35 to 128 residues, 35 to 127 residues, 35 to 126 residues, 35 to 125 residues, 35 to 124 residues, 35 to 123 residues, 35 to 122 residues, 35 to 121 residues, 35 to 120 residues, 35 to 119 residues, 35 to 118 residues, 35 to 117 residues, 35 to 116 residues, 35 to 115 residues, 35 to 114 residues, 35 to 113 residues, 35 to 112 residues, 35 to 111 residues, 35 to 100 residues, 35 to 109 residues, 35 to 108 residues, 35 to 107 residues, 35 to 106 residues, 35 to 105 residues, 35 to 104 residues, 35 to 103 residues, 35 to 102 residues, 35 to 101 residues, 35 to 100 residues, 35 to 99 residues, 35 to 98 residues, 35 to 97 residues, 35 to 96 residues, 35 to 95 residues, 35 to 94 residues, 35 to 93 residues, 35 to 92 residues, 35 to 91 residues, 35 to 90 residues, 35 to 89 residues, 35 to 88 residues, 35 to 87 residues, 35 to 86 residues, 35 to 85 residues, 35 to 84 residues, 35 to 83 residues, 35 to 82 residues, 35 to 81 residues, 35 to 80 residues, 35 to 79 residues, 35 to 78 residues, 35 to 77 residues, 35 to 76 residues, 35 to 75 residues, 35 to 74 residues, 35 to 73 residues, 35 to 72 residues, 35 to 71 residues, 35 to 70 residues, 35 to 69 residues, 35 to 68 residues, 35 to 67 residues, 35 to 66 residues, 35 to 65 residues, 35 to 64 residues, 35 to 63 residues, 35 to 62 residues, 35 to 61 residues, 35 to 60 residues, 35 to 59 residues, 35 to 58 residues, 35 to 57 residues, 35 to 56 residues, 35 to 55 residues, 35 to 54 residues, 35 to 53 residues, 35 to 52 residues, 35 to 51 residues, 35 to 50 residues, 35 to 49 residues, 35 to 48 residues, 35 to 47 residues, 35 to 46 residues, 35 to 45 residues, 35 to 44 residues, 35 to 43 residues, 35 to 42 residues, 35 to 41 residues, 35 to 40 residues, 35 to 39 residues, 35 to 38 residues, 35 to 37 residues, 35 to 36 residues or 35 residues. Preferably, the length of the at least one RNA molecule is in the range 36 to 174 residues, 37 to 173 residues, 38 to 172 residues, 39 to 171 residues, 40 to 170 residues, 41 to 169 residues, 42 to 168 residues, 43 to 167 residues, 44 to 166 residues, 45 to 165 residues, 46 to 164 residues, 47 to 163 residues, 48 to 162 residues, 49 to 161 residues, 50 to 160 residues, 51 to 159 residues, 52 to 158 residues, 53 to 157 residues, 54 to 156 residues, 36 to 74 residues, 37 to 73 residues, 38 to 72 residues, 39 to 71 residues, 40 to 70 residues, 41 to 69 residues, 42 to 68 residues, 43 to 67 residues, 44 to 66 residues, 45 to 65 residues, 46 to 64 residues, 47 to 63 residues, 48 to 62 residues, 49 to 61 residues, 50 to 60 residues, 51 to 59 residues, 52 to 58 residues, 53 to 57 residues, 54 to 56 residues.

In preferred aspects, the present invention provides a ribonucleoprotein complex, wherein the complementary portion of the at least one RNA molecule is at least 30 residues long. Alternatively, the complementary portion of the at least one RNA molecule may be 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74 or 75 residues long.

The targeting RNA molecule will preferably require a high specificity and affinity for the target nucleic acid sequence. A dissociation constant ($K_d$) in the range 1 µM to 1 pM, preferably 1 nM to 1 pM; more preferably 1-100 pM is desirable as may be determined by native gel electrophoresis, or alternatively isothermal titration calorimetry, surface plasmon resonance, or fluorescence based titration methods. Affinity may be determined using an electrophoretic mobility shift assay (EMSA), also called gel retardation assay (see Semenova et al. (2011) PNAS 108: 10098-10103).

The targeting RNA molecule is preferably modeled on what are known from nature in prokaryotes as CRISPR RNA (crRNA) molecules. The structure of crRNA molecules is already established and explained in more detail in Jore et al., 2011, Nature Structural & Molecular Biology 18: 529-537. In brief, a mature crRNA of type I-E is often 61 nucleotides long and consists of a 5' "handle" region of 8 nucleotides, the "spacer" sequence of 32 nucleotides, and a 3' sequence of 21 nucleotides which form a hairpin with a tetranucleotide loop (FIG. 5). Type I systems differ from type II (Cas9) and details of different systems are described in Van der Oost 2014 Nat Rev Micr 12: 479-492. In type II (Cas9) systems there is a different processing mechanism, making use of a second RNA (tracrRNA) and two ribonucleases. Rather than a hairpin, the mature crRNA in type II remains attached to a fragment of the tracrRNA (FIG. 5). However, the RNA used in the invention does not have to be designed strictly to the design of naturally occurring crRNA, whether in length, regions or specific RNA sequences. What is clear though, is that RNA molecules for use in the invention may be designed based on gene sequence information in the public databases or newly discovered, and then made artificially, e.g. by chemical synthesis in whole or in part. The RNA molecules of the invention may also be designed and produced by way of expression in genetically modified cells or cell free expression systems and this option may include synthesis of some or all of the RNA sequence.

The structure and requirements of crRNA in type II (Cas9) has also been described in Jinek et al., 2012 ibid. In type I, there is a so-called "SEED" portion forming the 5' end of the spacer sequence and which is flanked 5' thereto by the 5' handle of 8 nucleotides. Semenova et al. (2011, PNAS 108: 10098-10103), have found that all residues of the SEED sequence should be complementary to the target sequence, although for the residue at position 6, a mismatch may be tolerated (FIG. 5). In type II, there is a SEED of 10-12 nucleotides that is located at the 3' end of the spacer (FIG. 5) (reviewed by Van der Oost 2014 ibid.). Similarly, when designing and making an RNA component of a ribonucleoprotein complex of the invention directed at a target locus (i.e. sequence), the necessary match and mismatch rules for the type II SEED sequence can be applied.

The invention therefore includes a method of detecting and/or locating a single base change in a target nucleic acid molecule comprising contacting a nucleic acid sample with a ribonucleoprotein complex of the invention as hereinbefore described, or with a Cas protein or polypeptide and separate targeting RNA component of the invention as hereinbefore described, and wherein the sequence of the targeting RNA (including when in the ribonucleoprotein complex) is such that it discriminates between a normal allele and a mutant allele by virtue of a single base change at, for example, position 6 of a contiguous sequence of 8 nucleotide residues.

Without wishing to be bound by a particular theory, a design rule which may be used in preparing a targeting RNA component of ribonucleoprotein complexes of the invention involves the so-called "PAM" (protospacer adjacent motif) sequence in a double stranded target polynucleotide. In the type I-E system of *E. coli*, the PAM sequence may be a conserved triplet of nucleotide residues, such as 5'-CTT-3', 5'-CAT-3', 5'-CCT-3', 5'-CAC-3', 5'-TTT-3', 5'-ATT-3', and 5'-AWG-3', wherein W is A, T or U. In Type I, a PAM sequence located in the targeted strand is usually at a position corresponding to 5' of the SEED. In Type II, however, the PAM is located at the other end, on the displaced, or non-target, strand close to the 3' end of the crRNA spacer, at a position corresponding to 3' of the seed (FIG. 5) (Jinek et al., 2012, op. cit.). For *Streptococcus pyogenes* Cas9, the PAM sequence has a conserved pair of nucleotide residues, 5'-NGG-3'. Recently, different Cas9 variants (Type IIA and Type IIC) (Ran et al., 2015 Nature 520:186-191)—FIG. 1A) have been characterized, and PAMs have been revealed (see Ran et al., 2015, ibid. —FIG. 1C). Currently established Cas9 PAMs include: Type IIA 5'-NGGNNNN-3' (*Streptococcus pyogenes*), 5'-NNGTNNN-3' (*Streptococcus pasteurianus*), 5'-NNGGAAN-3' (*Streptococcus thermophilus*), 5'-NNGGGGN-3' (*Staphylococcus aureus*), and Type IIC 5'-NGGNNNN-3' (*Corynebacterium difteriae*), 5'-NNGGGTN-3' (*Campylobacter lari*), 5'-NNNCATN-3' (*Parvobaculum lavamentivorans*), 5'-NNNNGTA-3' (*Neiseria cinerea*). Cas9 of *Geobacillus thermodenitrificans* T12 (this invention) belongs to Type IIC (Ran et al., 2015, ibid.). The inventors have surprisingly found that the choice of PAM sequences for use with the invention can influence the temperature(s) at which the Cas proteins and polypeptides of the invention will interact with a target sequence. In particular, the inventors have found a preference for an 8-mer PAM sequence to confer activity across a broad temperature range, with a cytosine in the $5^{th}$ position after the 3' end of the target sequence, and/or an adenine in the $8^{th}$ position. There is also a preference for cytosine in the $1^{st}$, $2^{nd}$, $3^{rd}$, $4^{th}$ and/or $6^{th}$ position of the PAM sequence after the 3' end of the protospacer sequence.

In embodiments of the invention, a targeting RNA molecule may have a length in the range of 35-200 residues. In preferred embodiments, the portion of the RNA which is complementary to and used for targeting a desired nucleic acid sequence is from 15 to 32 residues long. In the context of a naturally-occurring crRNA, this would correspond to the spacer portion as shown for example in FIG. 1 of Semenova et al. (2011 ibid.).

A ribonucleoprotein complex of the invention may have a targeting component comprising 8 residues derived from the CRISPR repeat 5' to the RNA sequence which has substantial complementarity to the DNA target sequence. The RNA sequence having complementarity to the DNA target sequence would be understood to correspond in the context of a crRNA as being the spacer sequence. The 5' flanking sequence of the RNA would be considered to correspond to the 5' handle of a crRNA; as shown for example in FIG. 1 of Semenova et al. (2011 ibid.).

A ribonucleoprotein complex of the invention may have a hairpin and tetranucleotide loop forming sequence 3' to the targeting RNA sequence which has complementarity to a DNA target sequence, i.e. 3' to what would correspond to the 3' handle flanking the spacer sequence in a crRNA; for example as shown in FIG. 1 of Semenova et al. (2011 ibid.).

Without wishing to be bound by a particular theory, in a preferred ribonucleoprotein complex and double stranded target polynucleotide, the non-target nucleic acid strand, which does not pair with the targeting RNA of the ribonucleoprotein complex, may comprise a directly 3' adjacent PAM sequence selected from one or more of 5'-NNNNCNNA-3', 5'-CNNNCNN-3', 5'-NNNCCNN-3', 5'-NNCNCNN-3', 5'-NNNNCCN-3', and 5'-NCNNCNN-3'. Preferably the PAM sequence may be selected from 5'-NNNNC-3', 5'-NNNNCNNA-3', 5'-CNNNC-3', 5'-CNNNCNNA-3', 5'-NCNNC-3', 5'-NCNNCNNA-3', 5'-NNCNC-3', 5'-NNCNCNNA-3', 5'-NNNCC-3', 5'-NNNCCNNA-3', 5'-NNNNCC-3', 5'-NNNNCCNA-3', 5'-CCNNC-3', 5'-CCNNCNNA-3', 5'-CNCNC-3', 5'-CNCNCNNA-3', 5'-CNNCCN-3', 5'-CNNCCNNA-3', 5'-CNNNCC-3', 5'-CNNNCCNA-3', 5'-CCCNCN-3', 5'-CCCNCNNA-3', 5'-CCNCCN-3', 5'-CCNCCNNA-3', 5'-CCNNCC-3', 5'-CCNNCCNA-3', 5'-CCCCC-3' [SEQ ID NO: 12], 5'-CCCCCNNA-3' [SEQ ID NO: 13], 5'-CCCCCC-3' [SEQ ID NO: 14], 5'-CCCCCCNA-3' [SEQ ID NO: 10], 5'-NCCNC-3', 5'-NCCNCNNA-3', 5'-NCCCC-3', 5'-NCCCCNNA-3', 5'-NCCCCC-3' [SEQ ID NO: 15], 5'-NCCCCCNA-3' [SEQ ID NO: 16], 5'-NNCCC-3', 5'-NNCCCNNA-3', 5'-NNCCCC-3', 5'-NNCCCCNA-3', 5'-NNNCCC-3', and 5'-NNNCCCNA-3'. The PAM sequence may be 5'-CNCCCCAC-3' [SEQ ID NO: 17], 5'-CCCCCCAG-3' [SEQ ID NO: 18], 5'-CCCCCCAA-3' [SEQ ID NO: 11], 5'-CCCCCCAT-3' [SEQ ID NO: 19], 5'-CCCCCCAC-3' [SEQ ID NO: 20], 5'-ATCCCCAA-3' [SEQ ID NO: 21], or 5'-ACGGCCAA-3' [SEQ ID NO: 22]. Preferably the PAM sequence will be of the sequence 5'-NNNNCNNA-3'. However, it will be appreciated that other combinations of nucleotides may be used depending on the desired application and/or concentration of Cas protein or polypeptide. These sequences correspond to what is termed "protospacer adjacent motif" or "PAM" in the context of naturally occurring crRNAs. In type IIC CRISPR/Cas systems these PAM sequences facilitate stable interaction with the Cascade/crRNA complex with its dsDNA target, in order to ensure high degree of specificity of the crRNA—both in the natural system targets and therefore preferably also of the RNAs according to the present invention—for the target sequence. Preferably the sequence directly adjacent the protospacer will not be 5'-NNNCATN-3'.

The PAM sequences of the invention provided herein comprise the sequences disclosed herein, for example as 6-mer, 7-mer or 8-mer sequences. The 6-mer, 7-mer or 8-mer sequences may begin directly 3' of the protospacer sequence on the non-target strand, with no additional nucleic acids interspaced between the protospacer sequence, complimentary to that bound by the target RNA, and the 5' end of the PAM sequence. However, it will be appreciated that there may be additional nucleic acids forming part of the PAM sequence at the 3' end of the 6-mer, 7-mer or 8-mer sequences. Additionally or alternatively, the non-target strand may comprise additional nucleic acids 3' of the PAM sequence.

A nucleoprotein complex of the invention may comprise a ribonucleoprotein complex of the invention and the target nucleic acid strand of nucleic acid, with which the ribonucleoprotein is associated.

Binding, Cleavage, Marking and Modifying Temperatures

The temperature range, including optimal temperature range of the activity, for example nuclease activity, of the Cas proteins of the present invention is significantly higher than that of known Cas9 proteins. Also, the upper extent of the range in which it retains activity is much higher than that of known Cas9 proteins. A higher optimal temperature and functional range provides a significant advantage in genetic engineering at high temperatures and therefore, for example, in the editing of the genomes of thermophilic organisms, many of which have utility in a range of industrial, agricultural and pharmaceutical processes conducted at elevated temperatures. Thus the methods, uses, nucleoproteins and transformed cells of the invention may be useful in industrial processes, for example providing genome editing for metabolic engineering purposes. The presence of the PAM sequences of the invention, directly adjacent to the protospacer sequence in the non-target strand, improve the specificity of the Cas proteins and polypeptides for the target sequences, and support the use of the Cas proteins and polypeptides at higher temperatures and across larger functional temperature ranges.

Advantageously, Cas proteins or polypeptides of the invention are capable of nucleic acid binding, cleavage, marking or modifying at a temperature from 20° C. to 100° C. but are particularly useful at elevated temperatures, for example at a temperature between 41° C. and 122° C., preferably at a temperature between 50° C. and 100° C. Cas proteins and polypeptides of the invention are capable of binding, cleaving, marking or modifying DNA, RNA and synthetic nucleic acids. Cas proteins or polypeptides of the invention may also provide operability for nuclease activity, gene editing and nucleic acid marking applications at temperatures in the range 20 to 50° C., for example.

Where a temperature range is included herein, it is intended that the endpoints are included in the disclosed temperature range, i.e. that the range is "inclusive". For example, where it is stated that there is activity at a temperature in the range between 20° C. and 100° C., the temperatures of 20° C. and 100° C. are included in said range.

Preferably, Cas proteins or polypeptides of the invention, when associated with suitable gRNA (guide RNA, also called targeting RNA molecule) which recognizes a target sequence in the polynucleotide molecule(s) to be bound, cleaved, marked or modified, does so at temperatures in the range 50° C. to 100° C., optionally in the range 55° C. to 100° C., 60° C. to 100° C., 65° C. to 100° C., 70° C. to 100° C., 75° C. to 100° C., 80° C. to 100° C., 85° C. to 100° C., 90° C. to 100° C., 95° C. to 100° C. More preferably, Cas proteins of the invention cleave, mark or modify nucleic acids at temperatures in the range 51° C. to 99° C., 52° C. to 98° C., 53° C. to 97° C., 54° C. to 96° C., 55° C. to 95° C., 56° C. to 94° C., 57° C. to 93° C., 58° C. to 92° C., 59° C. to 91° C., 60° C. to 90° C., 61° C. to 89° C., 62° C. to 88° C., 63° C. to 87° C., 64° C. to 86° C., 65° C. to 85° C., 66° C. to 84° C., 67° C. to 83° C., 68° C. to 82° C., 69° C. to 81° C., 70° C. to 80° C., 71° C. to 79° C., 72° C. to 78° C., 73° C. to 77° C., 74° C. to 76° C., or at a temperature of 75° C. Preferably, Cas proteins of the invention bind, cleave, mark or modify nucleic acids at temperatures in the range 60° C. to 80° C., 61° C. to 79° C., 62° C. to 78° C., 63° C. to 77° C., 64° C. to 76° C., 60° C. to 75° C., 60° C. to 70° C. Optimally Cas proteins of the invention bind, cleave, mark or modify nucleic acids at temperatures in the range 60° C. to 65° C., preferably at 65° C.

Target RNA molecules may be designed for use with the Cas proteins and polypeptides of the invention, wherein the target RNA molecules bind to the target sequence in a target strand, and the non-target strand further comprises a PAM sequence provided herein immediately 3' of the protospacer sequence. The PAM sequence may comprise 5'-NNNNNNNA-3', preferably 5'-NNNNCNNA-3' for example 5'-CCCCCCNA-3' [SEQ ID NO: 10] or 5'-CCCCCCAA-3' [SEQ ID NO: 11], and the uses, methods, transformed cells, and nucleoproteins of the invention may provide binding, cleaving, marking and/or modifying of the target strand across the temperature range of from 55° C. to 65° C., preferably across the temperature range of from 50° C. to 70° C., from 40° C. to 65° C., from 45° C. to 75° C., from 37° C. to 78° C. and/or from 20° C. to 80° C.

In all aspects of the invention, Cas proteins or polypeptides may be obtained or derived from bacteria, archaea or viruses; or alternatively may be synthesised de novo. In preferred embodiments, a Cas protein or polypeptide of the invention is derived from a thermophilic prokaryotic organism, which may be classified as an archaea or bacterium, but is preferably a bacterium. More preferably a Cas protein or polypeptide of the invention will be derived from a thermophilic bacterium. Herein, the term thermophilic is to be understood as meaning capable of survival and growth at relatively high temperatures, for example in the context of the invention, capable of nucleic acid cleavage, binding or modification at a temperature between 41 and 122° C. (106 and 252° F.). Preferably a Cas protein or polypeptide of the invention may be isolated from one or more thermophilic bacteria and will function above 60° C. Preferably a Cas protein or polypeptide of the invention may be isolated from one or more thermophilic bacteria and will function in the range 60° C. to 80° C. and optimally between 60° C. and 65° C. In preferred embodiments, a Cas protein or polypeptide of the invention is derived from *Geobacillus* sp. More preferably, a Cas protein of the invention is derived from *Geobacillus thermodenitrificans*. Even more preferably, a Cas protein of the invention is derived from *Geobacillus thermodenitrificans* T12. A Cas protein or polypeptide of the invention may be derived from a virus.

Functional Moieties

Advantageously, the ability of Cas proteins, polypeptides and ribonucleoprotein complexes of the invention to target any polynucleotide sequence in a sequence-specific manner may be exploited in order to modify the target nucleic acid in some way, for example by cleaving it and/or marking it and/or modifying it. It will therefore be appreciated that additional proteins may be provided along with the Cas protein or polypeptide to achieve this. Accordingly, the Cas proteins or polypeptides of the invention may further comprise at least one functional moiety and/or the Cas proteins, polypeptides or ribonucleoprotein complexes of the present invention may be provided as part of a protein complex comprising at least one further protein. In a preferred aspect the present invention provides a Cas protein, polypeptide or a ribonucleoprotein complex wherein the Cas protein or at least one further protein further comprises at least one functional moiety. The at least one functional moiety may be fused or linked to the Cas protein. Preferably, the at least one functional moiety may be translationally fused to the Cas protein through expression in natural or artificial protein expression systems. Alternatively, the at least one functional moiety may be covalently linked by a chemical synthesis step to the Cas protein. Preferably, the at least one functional moiety is fused or linked to the N-terminus and/or the C-terminus of the Cas protein; preferably the C-terminus.

Desirably, the at least one functional moiety will be a protein. It may be a heterologous protein or alternatively may be native to the bacterial species from which the Cas protein was derived. The at least one functional moiety may be a protein; optionally selected from a helicase, a nuclease, a helicase-nuclease, a DNA methylase, a histone methylase, an acetylase, a phosphatase, a kinase, a transcription (co-) activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag.

In a particularly preferred aspect, the present invention provides a Cas protein, polypeptide, or a ribonucleoprotein complex, wherein the at least one functional moiety is a marker protein, for example GFP.

Nuclease Activity

A Cas ribonucleoprotein of the invention has nucleic acid binding, cleavage, marking or modification activity at a temperature, preferably an elevated temperature, disclosed herein, for example at a temperature between 50° C. and 100° C. The ribonucleoproteins of the invention may be capable of binding, cleaving, marking or modifying DNA, RNA or synthetic nucleic acids. In preferred aspects Cas ribonucleoproteins of the invention are capable of cleaving DNA in a sequence-specific manner, in particular double-stranded DNA.

Cas proteins, polypeptides or ribonucleoproteins of the invention may have more than one nuclease domain. Site-specific nucleases can permit the generation of double strand breaks (DSBs) at selected positions along a strand of DNA. In a target host cell, this enables DSBs to be made at specific pre-selected positions in the genome. The creation of such breaks by site-specific nucleases prompts the endogenous cellular repair machinery to be repurposed in order to insert, delete or modify DNA at desired positions in the genome of interest.

One or more nuclease activity sites of the protein or polypeptide molecule may be inactivated, e.g. so as to allow the activity of another functional moiety linked or fused to the protein or polypeptide, e.g. a nuclease domain such as FokI nuclease.

Therefore notwithstanding the fact that the Cas proteins, polypeptides and ribonucleoproteins of the invention may have endogenous nuclease activity, for certain applications it may be desirable to inactivate the native nuclease activity of the Cas protein and provide a Cas protein or a ribonucleoprotein complex wherein the native Cas9 nuclease activity is inactivated and the Cas protein is linked to at least one functional moiety. Reducing the incidence of mis-targeting events by complementation of the native Cas9 nuclease activity is one such application. This may desirably be achieved by inactivation of the native Cas9 nuclease activity of the Cas protein or ribonucleoprotein complex and provision of a heterologous nuclease, preferably fused to the Cas protein. Accordingly, the present invention provides a Cas protein or a ribonucleoprotein complex, wherein the at least one functional moiety is a nuclease domain, preferably a FokI nuclease domain. In a particularly preferred aspect, the Cas protein or ribonucleoprotein complex of the invention fused to a FokI nuclease domain is provided as part of a protein complex, preferably comprising another Cas protein or ribonucleoprotein complex of the invention fused to a FokI nuclease domain and wherein the two complexes target opposite strands of the target genomic DNA.

For some applications it may be desirable to completely attenuate the nuclease activity of the Cas protein, polypeptide or ribonucleoprotein, for example in applications where the Cas protein or ribonucleoprotein complex is utilised to recognise and modify a specific target sequence in a nucleic acid, for instance to mark it as part of a diagnostic test. In such applications, the nuclease activity of the Cas protein may be inactivated and the functional moiety fused to the Cas protein may be a protein; optionally selected from a helicase, a nuclease, a helicase-nuclease, a DNA methylase, a histone methylase, an acetylase, a phosphatase, a kinase, a transcription (co-)activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag.

In a preferred aspect, a catalytically inactive, or "dead" Cas protein or polypeptide (dCas) lacking nuclease activity may be bound to a target nucleic acid sequence and thereby sterically repress activity of that sequence. For example, a target RNA may be designed that is complementary to a promoter or exonic sequence of a gene, so that binding of the dCas and target RNA to the gene sterically represses transcriptional initiation or elongation of the gene sequence, thereby repressing expression of the gene. Alternatively, the methods and uses described herein can use modified nuclease variants of gtCas9 that are nickases. A nickase can be created via a mutation in either one of the HNH or the RuvC catalytic domains of the gtCas9 nuclease. This has been shown for *S. pyogenes* Cas9 (spCas) with spCas9-mutants D10A and H840A, which have an inactive RuvC or HNH nuclease domain, respectively. The combination of these two mutations leads to a catalytically dead Cas9 variant (Standage-Beier, K. et al., 2015, ACS Synth. Biol. 4, 1217-1225; Jinek, M. et al., 2012, Science 337, 816-821; Xu, T. et al., 2015, Appl. Environ. Microbiol. 81, 4423-4431). Based on sequence homology (FIG. 3), these residues can be D8 (D17 in FIG. 3) and D581 or H582 (FIG. 3) in gtCas9.

In a particularly preferred aspect, the present invention provides a Cas protein or a ribonucleoprotein complex, wherein the nuclease activity of the Cas protein is inactivated and the at least one functional moiety is a marker protein, for example GFP. In this way it may be possible to specifically target a nucleic acid sequence of interest and to visualize it using a marker which generates an optical signal. Suitable markers may include for example, a fluorescent reporter protein, e.g. Green Fluorescent Protein (GFP), Yellow Fluorescent Protein (YFP), Red Fluorescent Protein (RFP), Cyan Fluorescent Protein (CFP) or mCherry. Such a fluorescent reporter gene provides a suitable marker for visualisation of protein expression since its expression can be simply and directly assayed by fluorescence measurement. Alternatively, the reporter nucleic acid may encode a luminescent protein, such as a luciferase (e.g. firefly luciferase). Alternatively, the reporter gene may be a chromogenic enzyme which can be used to generate an optical signal, e.g. a chromogenic enzyme (such as beta-galactosidase (LacZ) or beta-glucuronidase (Gus)). Reporters used for measurement of expression may also be antigen peptide tags. Other reporters or markers are known in the art, and they may be used as appropriate.

Because the marker may be visualized, in certain embodiments where the target nucleic acid is RNA, specifically mRNA, it may be possible to quantify the transcriptional activity of a gene by detection and quantification of the optical signal provided by the marker, particularly where the optical signal generated by the marker is directly proportionate to the quantity of the expression product. Therefore in preferred embodiments of the invention, Cas proteins or ribonucleoproteins of the invention may be used to assay expression products of a gene of interest.

In one aspect, the gtCas9 described herein may be used in a homologous recombination (HR) mediated genome modification method in microbial cells. Such methods involve HR and site-directed gtCas9 activity, whereby counter selection occurs by the gtCas9 activity removing microbes which do not have a desired modification introduced by HR.

Thus the methods and uses provided herein allow the process of homologous recombination to be favoured during a first step such that the microbial genome can be modified with the desired mutation and a second step in which unmodified cells can be targeted by the gtCas9 ribonuclease complex to introduce a DSDB into the genomes of the unmodified cells. Due to an absence of an efficient non-homologous end joining (NHEJ) repair mechanism in the majority of microbes, DSDB typically leads to cell death. Thus, these methods and uses increase overall the population of microbial cells with the desired mutation whilst eliminating any unmodified microbial cells. Preferably, such methods and uses are used in microbes that have substantially no endogenous NHEJ repair mechanism. Alternatively, the methods and uses may be applied to microbes that have an endogenous NHEJ repair mechanism. The methods and uses described herein may be applied to microbes that have an endogenous NHEJ repair mechanism but wherein the NHEJ repair mechanism is either conditionally reduced or the NHEJ activity is knocked out.

The methods and uses provided herein may utilise a sequence of the homologous recombination polynucleotide that has at least one mis-match with the guide RNA, such that the guide RNA is no longer able to recognise the modified genome. This means that the gtCas9 ribonuclease complex will not recognise the modified genome. Therefore, no DSDB can be introduced by the gtCas9 ribonuclease complex and so the modified cells will survive. However, the cells with unmodified genomes will still have substantial complementarity to the guide RNA and consequently can be cleaved site-specifically by the gtCas9 ribonuclease complex.

In another aspect of the methods and uses of the invention, the way in which the gtCas9 ribonucleoase complex is prevented from acting to cleave the microbial genome is not so much to modify or eliminate the sequence targeted by the guide, but rather the PAM required by the gtCas9 ribonuclease complex. The PAM is either modified or eliminated in order to blind the gtCas9 ribonuclease complex to the specific cutting site. Therefore, methods and uses of the invention may include those using a sequence of the homologous recombination polynucleotide that does not include a PAM sequence recognised by the gtCas9 ribonuclease complex. Therefore, no DSDB can be introduced by the gtCas9 ribonuclease complex and so the HR modified cells will survive. However, the unmodified cells will still be recognised by the gtCas9 ribonuclease complex and its guide and so consequently are cleaved site-specifically.

Thus methods and uses are provided herein that rely on HR to modify the genome of the microbe. Preferably, the upstream flank and downstream flanks are 0.5 kilobases (kb) to 1.0 kb each in length. However, recombination using larger or shorter fragments is possible as well. The homologous recombination polynucleotide may further comprise a polynucleotide sequence between the upstream and downstream flanking regions. This polynucleotide sequence could for example contain a modification that is to be introduced into the microbial genome.

Whilst homologous recombination relies upon the upstream and downstream flanks having substantial complementarity to the target regions, mismatches can be accommodated as well. Therefore, in some embodiments, homologous recombination is known to occur between DNA segments with extensive homology to the upstream and downstream flanks. In alternative embodiments, the upstream and downstream flanks have complete complementarity to the target regions. The upstream and downstream flanks need not be identical in size. However, in some instances the upstream and downstream flanks are identical in size. The efficiency of homologous recombination will vary depending on the likelihood of homologous recombination of the smallest fragment length of the flank. However, even if the homologous recombination process is inefficient, advantageously the method described herein will select for any microbial cell that has the desired modification over the unmodified microbial cell. Homologous recombination also allows large deletions (e.g. 50 kb or more) to be made encompassing complete gene clusters. Homologous recombination is also used for recombineering, which is a well-known method to allow for recombination over smaller fragments (45-100 nt). The methods and uses described herein can optionally further comprise at least another homologous recombination polynucleotide or a polynucleotide comprising a sequence encoding a homologous recombination polynucleotide having a sequence substantially complementary to a second target region containing the target in the microbial genome.

In preferred embodiments, the methods and uses described herein utilise a homologous recombination polynucleotide that is DNA. In some embodiments the DNA is single stranded. In other embodiments, the DNA is double stranded. In further embodiments, the DNA is double stranded and plasmid borne.

HR in the methods and uses provided herein may be used to remove a polynucleotide sequence from the microbial genome. Alternatively, HR in the methods and uses provided herein may be used to insert one or more gene(s), or fragment(s) thereof, in to the microbial genome. As a further alternative, HR in the methods and uses provided herein may be used to modify or replace at least one nucleotide in the microbial genome. Consequently, the methods and uses provided herein may be used for any desired kind of genome modification.

Alternatively, the gtCas9 described herein may be used in a HR mediated genome modification method in microbial cells, whereby the gtCas9 activity introduces DSDB and can induce cellular HR in microbial cells, as has been shown for spCas9 (Jiang et al. (2013) Nature Biotech, 31, 233-239; Xu et al. (2015) Appl Environ Microbiol, 81, 4423-4431; Huang et al. (2015) Acta Biochimica et Biophysica Sinica, 47, 231-243).

Alternatively, homologous recombination may be facilitated through recombineering, e.g., by introducing an oligonucleotide into a microbial cell expressing a gene coding for RecT or beta protein as reviewed by Mougiakos et al. ((2016), Trends Biotechnol. 34: 575-587). In a further embodiment, the Cas9 can be combined with Multiplex Automated Genome Engineering (MAGE) as exemplified by Ronda et al. ((2016), Sci. Rep. 6: 19452.)

Throughout, the reference sequences of the Cas proteins of the invention may be defined as a nucleotide sequence encoding the amino acid sequence. For example the amino acid sequence of the motifs defined in SEQ ID's 2 to 6 also includes all nucleic acid sequences which encode that amino acid sequence.

Accordingly, the present invention also provides an isolated nucleic acid molecule encoding a Cas protein comprising;
  a. the amino acid motif EKDGKYYC [SEQ ID NO: 2]; and/or
  b. the amino acid motif $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and/or
  c. the amino acid motif $X_5LKX_6IE$ [SEQ ID NO: 4] wherein $X_5$ is independently selected from Methionine or Phenylalanine and $X_6$ is independently selected from Histidine or Asparagine; and/or
  d. the amino acid motif $X_7VYSX_8K$ [SEQ ID NO: 5] wherein $X_7$ is Glutamate or Isoleucine and $X_8$ is one of Tryptophan, Serine or Lysine; and/or
  e. the amino acid motif $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine;

wherein the Cas protein is capable of DNA binding, cleavage, marking or modification between 50° C. and 100° C. when associated with at least one targeting RNA molecule, and a polynucleotide comprising a target nucleic acid sequence recognised by the targeting RNA molecule.

In another aspect the present invention also provides an isolated nucleic acid molecule encoding a clustered regularly interspaced short palindromic repeat (CRISPR)-associated (Cas) protein having an amino acid sequence of SEQ ID NO: 1 or a sequence of at least 77% identity therewith.

In another aspect the present invention also provides an isolated nucleic acid molecule, further comprising at least one nucleic acid sequence encoding a peptide which upon translation is fused to the Cas protein.

In another aspect the present invention also provides an isolated nucleic acid molecule, wherein the at least one nucleic acid sequence fused to the nucleic acid molecule encoding the Cas protein encodes a protein selected from a helicase, a nuclease, a helicase-nuclease, a DNA methylase, a histone methylase, an acetylase, a phosphatase, a kinase, a transcription (co-)-activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag.

Expression Vectors

Nucleic acids of the present invention may be isolated. However, in order that expression of the nucleic acid sensing construct may be carried out in a chosen cell, the polynucleotide sequence encoding the Cas protein or ribonucleoprotein will preferably be provided in an expression construct. In some embodiments, the polynucleotide encoding the Cas protein or ribonucleoprotein will be provided as part of a suitable expression vector. In certain embodiments an expression vector of the present invention (with or without nucleotide sequence encoding amino acid residues which on expression will be fused to a Cas protein) may further comprise a nucleotide sequence encoding a targeting RNA molecule as hereinbefore defined. Consequently, such expression vectors can be used in an appropriate host to generate a ribonucleoprotein complex of the invention which can target a desired nucleotide sequence. Alternatively, nucleotide sequences encoding a targeting RNA molecule as hereinbefore defined may be provided in a separate expression vector or alternatively may be delivered to a target cell by other means.

Suitable expression vectors will vary according to the recipient cell and suitably may incorporate regulatory elements which enable expression in the target cell and preferably which facilitate high-levels of expression. Such regulatory sequences may be capable of influencing transcription or translation of a gene or gene product, for example in terms of initiation, accuracy, rate, stability, downstream processing and mobility.

Such elements may include, for example, strong and/or constitutive promoters, 5' and 3' UTR's, transcriptional and/or translational enhancers, transcription factor or protein binding sequences, start sites and termination sequences, ribosome binding sites, recombination sites, polyadenylation sequences, sense or antisense sequences, sequences ensuring correct initiation of transcription and optionally poly-A signals ensuring termination of transcription and transcript stabilisation in the host cell. The regulatory sequences may be plant-, animal-. bacteria-, fungal- or virus derived, and preferably may be derived from the same organism as the host cell. Clearly, appropriate regulatory elements will vary according to the host cell of interest. For example, regulatory elements which facilitate high-level expression in prokaryotic host cells such as in *E. coli* may include the pLac, T7, P(Bla), P(Cat), P(Kat), trp or tac promoters. Regulatory elements which facilitate high-level expression in eukaryotic host cells might include the AOX1 or GAL1 promoter in yeast or the CMV- or SV40-promoters, CMV-enhancer, SV40-enhancer, Herpes simplex virus VIP16 transcriptional activator or inclusion of a globin intron in animal cells. In plants, constitutive high-level expression may be obtained using, for example, the *Zea mays* ubiquitin 1 promoter or 35S and 19S promoters of cauliflower mosaic virus.

Suitable regulatory elements may be constitutive, whereby they direct expression under most environmental conditions or developmental stages, developmental stage specific or inducible. Preferably, the promoter is inducible, to direct expression in response to environmental, chemical or developmental cues, such as temperature, light, chemicals, drought, and other stimuli. Suitably, promoters may be chosen which allow expression of the protein of interest at particular developmental stages or in response to extra- or intra-cellular conditions, signals or externally applied stimuli. For example, a range of promoters exist for use in *E. coli* which give high-level expression at particular stages of growth (e.g. osmY stationary phase promoter) or in response to particular stimuli (e.g. HtpG Heat Shock Promoter).

Suitable expression vectors may comprise additional sequences encoding selectable markers which allow for the selection of said vector in a suitable host cell and/or under particular conditions.

The invention also includes a method of modifying a target nucleic acid in a cell, comprising transfecting, transforming or transducing the cell with any of the expression vectors as hereinbefore described. The methods of transfection, transformation or transduction are of the types well known to a person of skill in the art. Where there is one expression vector used to generate expression of a ribonucleoprotein complex of the invention and when the targeting RNA is added directly to the cell then the same or a different method of transfection, transformation or transduction may be used. Similarly, when there is one expression vector being used to generate expression of a ribonucleoprotein complex of the invention and when another expression vector is being used to generate the targeting RNA in situ via expression, then the same or a different method of transfection, transformation or transduction may be used.

In other embodiments, mRNA encoding the Cas protein or polypeptide is introduced into a cell so that the Cascade complex is expressed in the cell. The targeting RNA which guides the Cas protein complex to the desired target sequence is also introduced into the cell, whether simultaneously, separately or sequentially from the mRNA, such that the necessary ribonucleoprotein complex is formed in the cell.

Accordingly, the invention also provides a method of modifying, i.e. cleaving, tagging, modifying, marking or binding, a target nucleic acid comprising contacting the nucleic acid with a ribonucleoprotein complex as hereinbefore defined.

In addition, the invention also includes a method of modifying a target nucleic acid comprising contacting the nucleic acid with a Cas protein or polypeptide as hereinbefore defined, in addition to a targeting RNA molecule as hereinbefore defined.

In accordance with the above methods, modification of target nucleic acid may therefore be carried out in vitro and in a cell-free environment. In a cell-free environment, addition of each of the target nucleic acid, the Cas protein and the targeting RNA molecule may be simultaneous, sequential (in any order as desired), or separately. Thus it is possible for the target nucleic acid and targeting RNA to be added simultaneously to a reaction mix and then the Cas protein or polypeptide of the invention to be added separately at a later stage.

Equally, the modification of the target nucleic acid may be made in vivo, that is in situ in a cell, whether an isolated cell or as part of a multicellular tissue, organ or organism. In the context of whole tissue and organs, and in the context of an organism, the method may desirably be carried out in vivo or alternatively may be carried out by isolating a cell from the whole tissue, organ or organism, treating the cell with ribonucleoprotein complex in accordance with the method and subsequently returning the cell treated with ribonucleoprotein complex to its former location, or a different location, whether within the same or a different organism.

In these embodiments, the ribonucleoprotein complex or the Cas protein or polypeptide requires an appropriate form of delivery into the cell. Such suitable delivery systems and methods are well known to persons skilled in the art, and include but are not limited to cytoplasmic or nuclear microinjection. In preferred modes of delivery, an Adeno-associated virus (AAV) is used; this delivery system is not disease causing in humans and has been approved for clinical use in Europe.

Accordingly the present invention provides a method of modifying a target nucleic acid comprising contacting the nucleic acid with:
  a. a ribonucleoprotein complex as hereinbefore defined; or
  b. a protein or protein complex as hereinbefore defined and an RNA molecule as hereinbefore defined.

In a further aspect the present invention provides a method of modifying a target nucleic acid in a cell, comprising transforming, transfecting or transducing the cell with an expression vector comprising nucleotide sequences encoding a ribonucleoprotein complex as hereinbefore defined; or alternatively transforming, transfecting or transducing the cell with an expression vector comprising nucleotide sequences encoding a protein or protein complex as hereinbefore defined and a further expression vector comprising a nucleotide sequence encoding a targeting RNA molecule as hereinbefore defined.

In a further aspect, the present invention provides a method of modifying a target nucleic acid in a cell comprising transforming, transfecting or transducing the cell with an expression vector comprising nucleotide sequences encoding a protein or protein complex as hereinbefore defined, and then delivering a targeting RNA molecule as hereinbefore defined into the cell.

In embodiments where the guide (i.e. targeting) RNA (gRNA) molecule and the Cas protein or polypeptide are provided separately rather than as part of a ribonucleoprotein complex, the gRNA molecule requires an appropriate form of delivery into a cell, whether simultaneously, separately or sequentially with the Cas protein or protein complex. Such forms of introducing RNA into cells are well known to a person of skill in the art and may include in vitro or ex vivo delivery via conventional transfection methods. Physical methods, such as microinjection and electroporation, as well as calcium co-precipitation, and commercially available cationic polymers and lipids, and cell-penetrating peptides, cell-penetrating (biolistic) particles may each be used. For example, viruses, particularly preferred is AAV, may be used as delivery vehicles, whether to the cytoplasm and/or nucleus, for example via the (reversible) fusion of Cas protein complex of the invention or a ribonucleoprotein complex of the invention to the viral particle.

In another aspect the present invention provides a method of modifying a target nucleic acid, wherein the at least one functional moiety is a marker protein or reporter protein and the marker protein or reporter protein associates with the target nucleic acid; preferably wherein the marker is a fluorescent protein, for example a green fluorescent protein (GFP).

In the aforementioned methods of modifying a target nucleic acid, the functional moiety may be a marker and the marker associates with the target nucleic acid; preferably wherein the marker is a protein; optionally a fluorescent protein, e.g. green fluorescent protein (GFP), yellow fluorescent protein (YFP), red fluorescent protein (RFP) or mCherry. Whether in vitro, ex vivo or in vivo, then methods of the invention can be used to directly visualise a target locus in a nucleic acid molecule, preferably in the form of a higher order structure such as a supercoiled plasmid or chromosome, or a single stranded target nucleic acid such as mRNA. Direct visualisation of a target locus may use electron micrography, or fluorescence microscopy. However, it will be appreciated that in the context of methods of the invention, other kinds of label may be used as the marker including organic dye molecules, radiolabels and spin labels which may be small molecules.

In methods of the invention for modifying a target nucleic acid wherein the target nucleic acid is dsDNA, the functional moiety may be a nuclease or a helicase-nuclease, and the modification is preferably a single stranded or a double stranded break at a desired locus. In this way unique sequence specific cutting of DNA can be engineered by using a suitable functional moiety fused to a ribonucleoprotein complex. The chosen sequence of the RNA component of the final ribonucleoprotein complex provides the desired sequence specificity for the action of the functional moiety.

Therefore, the invention also provides a method of non-homologous end joining of a dsDNA molecule in a cell at a desired locus to remove at least a part of a nucleotide sequence from the dsDNA molecule; optionally to knockout the function of a gene or genes, wherein the method comprises making double stranded breaks using any of the methods of modifying a target nucleic acid as hereinbefore described.

The invention further provides a method of homologous recombination of a nucleic acid into a dsDNA molecule in a cell at a desired locus in order to modify an existing nucleotide sequence or insert a desired nucleotide sequence, wherein the method comprises making a double stranded break at the desired locus using any of the methods of modifying a target nucleic acid as hereinbefore described.

The invention therefore also provides a method of modifying gene expression in an organism comprising modifying a target nucleic acid sequence according to any of the methods hereinbefore described, wherein the nucleic acid is dsDNA and the functional moiety is selected from a DNA modifying enzyme (e.g. a methylase or acetylase), a transcription activator or a transcription repressor.

The invention additionally provides a method of modifying gene expression in an organism comprising modifying a target nucleic acid sequence according to any of the methods hereinbefore described, wherein the nucleic acid is an mRNA and the functional moiety is a ribonuclease; optionally selected from an endonuclease, a 3' exonuclease or a 5' exonuclease.

The target nucleic acid may be DNA, RNA or synthetic nucleic acid. Preferably the target nucleic acid is DNA; preferably dsDNA.

However, the target nucleic acid can be RNA; preferably mRNA. Alternatively therefore, the present invention also provides methods of modifying a target nucleic acid, wherein the target nucleic acid is RNA.

In another aspect the present invention provides a method of modifying a target nucleic acid, wherein the nucleic acid is dsDNA, the at least one functional moiety is a nuclease or a helicase-nuclease, and the modification is a single-stranded or a double-stranded break at a desired locus.

In another aspect the present invention provides a method of modifying a target nucleic acid in a cell, wherein modification results in a silencing of gene expression at a desired locus; and wherein the method includes the steps of;

a. making double-stranded breaks in the dsDNA molecule; and b. repair of the dsDNA molecule in the cell by non-homologous end joining (NHEJ).

In another aspect the present invention provides a method of modifying a target nucleic acid in a cell; wherein the existing nucleotide sequence is modified or deleted and/or a desired nucleotide sequence is inserted at a desired location wherein the method includes the steps of;

a. making a double stranded break at the desired locus; and b. repair of the dsDNA molecule in the cell by homologous recombination.

In another aspect the present invention provides a method of modifying gene expression in a cell comprising modifying a target nucleic acid sequence as hereinbefore described; wherein the nucleic acid is dsDNA and the functional moiety is selected from a DNA modifying enzyme (e.g. a methylase or acetylase), a transcription activator or a transcription repressor.

In another aspect the present invention provides a method of modifying gene expression in a cell comprising modifying a target nucleic acid sequence as hereinbefore described; wherein the nucleic acid is an mRNA and the functional moiety is a ribonuclease; optionally selected from an endonuclease, a 3' exonuclease or a 5' exonuclease.

In another aspect the present invention provides a method of modifying a target nucleic acid as hereinbefore described, wherein the method is carried out at a temperature between 45° C. and 100° C. Preferably, the method is carried out at a temperature at or above 50° C. More preferably, the method is carried out at a temperature between 55° C. and 80° C. Optimally, the method is carried out at a temperature between 60° C. and 65° C. Alternatively, the method may be carried out at a temperature between 20° C. and 45° C. More preferably, at a temperature between 30° C. and 45° C. Even more preferably at a temperature between 37° C. and 45° C.

In any of the methods of modifying a target nucleic acid hereinbefore described, the cell may be a prokaryotic cell or alternatively, may be a eukaryotic cell.

Host Cells

Advantageously, the present invention is of broad applicability and host cells of the present invention may be derived from any genetically tractable organism which can be cultured. Accordingly, the present invention provides a host cell transformed by a method as hereinbefore described. The invention provides a transformed cell, having a target nucleic acid sequence in a double stranded target polynucleotide, said cell comprising a Cas protein or polypeptide as provided herein and at least one targeting RNA molecule as provided herein, and an expression vector comprising a nucleic acid encoding at least one of said Cas protein and said targeting RNA molecule.

Appropriate host cells may be prokaryotic or eukaryotic. In particular, commonly used host cells may be selected for use in accordance with the present invention including prokaryotic or eukaryotic cells which are genetically accessible and which can be cultured, for example prokaryotic cells, fungal cells, plant cells and animal cells including human cells (but not embryonic stem cells). Preferably, host cells will be selected from a prokaryotic cell, a fungal cell, a plant cell, a protist cell or an animal cell. Preferred host cells for use in accordance with the present invention are commonly derived from species which typically exhibit high growth rates, are easily cultured and/or transformed, display short generation times, species which have established genetic resources associated with them or species which have been selected, modified or synthesized for optimal expression of heterologous protein under specific conditions. In preferred embodiments of the invention where the protein of interest is eventually to be used in specific industrial, agricultural, chemical or therapeutic contexts, an appropriate host cell may be selected based on the desired specific conditions or cellular context in which the protein of interest is to be deployed. Preferably the host cell will be a prokaryotic cell. In preferred embodiments the host cell is a bacterial cell. The host cell may for instance be an *Escherichia coli* (*E. coli*) cell. Preferably the host cell will be a cell of a thermophilic bacterium.

Methods and uses of the invention described herein may be used to modify genomes of bacterial cells. In particular embodiments, the bacteria are thermophilic bacteria, preferably the bacteria are selected from: *Acidithiobacillus* species including *Acidithiobacillus caldus*; *Aeribacillus* species including *Aeribacillus pallidus*; *Alicyclobacillus* species including *Alicyclobacillus acidocaldarius, Alicyclobacillus acidoterrestris, Alicyclobacillus cycloheptanicusl, Alicyclobacillus hesperidum*; *Anoxybacillus* species including *Anoxybacillus caldiproteolyticus, Anoxybacillus flavithermus, Anoxybacillus rupiensis, Anoxybacillus tepidamans*; *Bacillus* species including *Bacillus caldolyticus, Bacillus caldotenax, Bacillus caldovelox, Bacillus coagulans, Bacillus clausii, Bacillus licheniformis, Bacillus methanolicus, Bacillus smithii* including *Bacillus smithii* ET138, *Bacillus subtilis, Bacillus thermocopriae, Bacillus thermolactis, Bacillus thermoamylovorans, Bacillus thermoleovorans*; *Caldibacillus* species including *Caldibacillus debilis*; *Caldicellulosiruptor* species including *Caldicellulosiruptor bescii, Caldicellulosiruptor hydrothermalis, Caldicellulosiruptor kristjanssonii, Caldicellulosiruptor kronotskyensis, Caldicellulosiruptor lactoaceticus, Caldicellulosiruptor obsidiansis, Caldicellulosiruptor owensensis, Caldicellulosiruptor saccharolyticus*; *Clostridium* species including *Clostridium clariflavum, Clostridium straminisolvens, Clostridium tepidiprofundi, Clostridium thermobutyricum, Clostridium thermocellum, Clostridium thermosuccinogenes, Clostridium thermopalmarium*; *Deinococcus* species including *Deinococcus cellulosilyticus, Deinococcus deserti, Deinococcus geothermalis, Deinococcus murrayi, Deinococcus radiodurans*; *Defluviitalea* species including *Defluviitalea phaphyphila, Desulfotomaculum* species including *Desulfotomaculum carboxydivorans, Desulfotomaculum nigrificans, Desulfotomaculum salinum, Desulfotomaculum solfataricum*; *Desulfurella* species including *Desulfurella acetivorans*; *Desulfurobacterium* species including *Desulfurobacterium thermolithotrophum*; *Geobacillus* species including *Geobacillus icigianus, Geobacillus caldoxylosilyticus, Geobacillus jurassicus, Geobacillus galactosidasius, Geobacillus kaustophilus, Geobacillus lituanicus, Geobacillus stearothermophilus, Geobacillus subterraneus, Geobacillus thermantarcticus, Geobacillus thermocatenulatus, Geobacillus thermodenitrificans, Geobacillus thermoglucosidans, Geobacillus thermoleovorans, Geobacillus toebii, Geobacillus uzenensis, Geobacillus vulcanii, Geobacillus zalihae*; *Hydrogenobacter* species including *Hydrogenobacter thermophiles*; *Hydrogenobaculum* species including *Hydrogenobaculum acidophilum*; *Ignavibacterium* species including *Ignavibacterium album*; *Lactobacillus* species including *Lactobacillus bulgaricus, Lactobacillus delbrueckii, Lactobacillus ingluviei, Lactobacillus thermotolerans*; *Marinithermus* species including *Marinithermus hydrothermalis*; *Moorella* species including *Moorella thermoacetica*; *Oceanithermus* species including *Oceanithermus desulfurans*, *Oceanithermus profundus*; *Paenibacillus* species including *Paenibacillus* sp. J2, *Paenibacillus marinum*, *Paenibacillus thermoaerophilus*; *Persephonella* species including *Persephonella guaymasensis*, *Persephonella hydrogeniphila*, *Persephonella marina*; *Rhodothermus* species including *Rhodothermus marinus*, *Rhodothermus obamensis*, *Rhodothermus profundi*; *Sulfobacillus* species including *Sulfobacillus acidophilus*; *Sulfurihydrogenibium* species including *Sulfurihydrogenibium azorense*, *Sulfurihydrogenibium kristjanssonii*, *Sulfurihydrogenibium rodmanii*, *Sulfurihydrogenibium yellowstonense*; *Symbiobacterium* species including *Symbiobacterium thermophilum*, *Symbiobacterium toebii*; *Thermoanaerobacter* species including *Thermoanaerobacter brockii*, *Thermoanaerobacter ethanolicus*, *Thermoanaerobacter italicus*, *Thermoanaerobacter kivui*, *Thermoanaerobacter marianensis*, *Thermoanaerobacter mathranii*, *Thermoanaerobacter pseudoethanolicus*, *Thermoanaerobacter wiegelii*; *Thermoanaerobacterium* species including *Thermoanaerobacterium aciditolerans*, *Thermoanaerobacterium aotearoense*, *Thermoanaerobacterium ethanolicus*, *Thermoanaerobacterium pseudoethanolicus*, *Thermoanaerobacterium saccharolyticum*, *Thermoanaerobacterium thermosaccharolyticum*, *Thermoanaerobacterium xylanolyticum*; *Thermobacillus* species including *Thermobacillus composti*, *Thermobacillus xylanilyticus*; *Thermocrinis* species including *Thermocrinis albus*, *Thermocrinis ruber*; *Thermodulfatator* species including *Thermodesulfatator atlanticus*, *Thermodesulfatator autotrophicus*, *Thermodesulfatator indicus*; *Thermodesulfobacterium* species including *Thermodesulfobacterium commune*, *Thermodesulfobacterium hydrogeniphilum*; *Thermodesulfobium* species including *Thermodesulfobium narugense*; *Thermodesulfovibrio* species including *Thermodesulfovibrio aggregans*, *Thermodesulfovibrio thiophilus*, *Thermodesulfovibrio yellowstonii*; *Thermosipho* species including *Thermosipho africanus*, *Thermosipho atlanticus*, *Thermosipho melanesiensis*; *Thermotoga* species including *Thermotoga maritima*, *Thermotoga neopolitana*, *Thermotoga* sp. RQ7; *Thermovibrio* species including *Thermovibrio ammonificans*, *Thermovibrio ruber*; *Thermovirga* species including *Thermovirga lienii* and *Thermus* species including *Thermus aquaticus*, *Thermus caldophilus*, *Thermus flavus*, *Thermus scotoductus*, *Thermus thermophilus*; *Thiobacillus neapolitanus*.

In another aspect, a method or use described herein can be used to modify bacteria that are mesophilic. In preferred embodiments, the bacteria are selected from: *Acidithiobacillus* species including *Acidithiobacillus caldus*; *Actinobacillus* species including *Actinobacillus succinogenes*; *Anaerobiospirillum* species including *Anaerobiospirillum succiniciproducens*; *Bacillus* species including *Bacillus alcaliphilus*, *Bacillus amyloliquefaciens*, *Bacillus circulans*, *Bacillus cereus*, *Bacillus clausii*, *Bacillus firmus*, *Bacillus halodurans*, *Bacillus lautus*, *Bacillus lentus*, *Bacillus licheniformis*, *Bacillus megaterium*, *Bacillus pumilus*, *Bacillus subtilis*, *Bacillus thuringiensis*; *Basfia* species including *Basfia* succiniciproducens; *Brevibacillus* species including *Brevibacillus brevis*; *Brevibacillus laterosporus*; *Clostridium* species including *Clostridium acetobutylicum*, *Clostridium autoethanogenum*, *Clostridium beijerinkii*, *Clostridium carboxidivorans*, *Clostridium cellulolyticum*, *Clostridium ljungdahlii*, *Clostridium pasteurianum*, *Clostridium perfringens*, *Clostridium ragsdalei*, *Clostridium saccharobutylicum*, *Clostridium saccharoperbutylacetonium*; *Corynebacterium* species including *Corynebacterium glutamicum*; *Desulfitobacterium* species including *Desulfitobacterium dehalogenans*, *Desulfitobacterium hafniense*; *Desulfotomaculum* species including *Desulfotomaculum acetoxidans*, *Desulfotomaculum gibsoniae*, *Desulfotomaculum reducens*, *Desulfotomaculum ruminis*; *Enterobacter* species including *Enterobacter asburiae*; *Enterococcus* species including *Enterococcus faecalis*; *Escherichia* species including *Escherichia coli*; *Lactobacillus* species including *Lactobacillus acidophilus*, *Lactobacillus amylophilus*, *Lactobacillus amylovorus*, *Lactobacillus animalis*, *Lactobacillus arizonensis*, *Lactobacillus bavaricus*, *Lactobacillus brevis*, *Lactobacillus buchneri*, *Lactobacillus bulgaricus*, *Lactobacillus casei*, *Lactobacillus corynoformis*, *Lactobacillus crispatus*, *Lactobacillus curvatus*, *Lactobacillus delbrueckii*, *Lactobacillus fermentum*, *Lactobacillus gasseri*, *Lactobacillus helveticus*, *Lactobacillus johnsonii*, *Lactobacillus pentosus*, *Lactobacillus plantarum*, *Lactobacillus reuteri*, *Lactobacillus rhamnosus*, *Lactobacillus sakei*, *Lactobacillus salivarius*, *Lactobacillus sanfriscensis*; *Mannheimia* species including *Mannheimia succiniciproducens*; *Paenibacillus* species including *Paenibacillus alvei*, *Paenibacillus beijingensis*, *Paenibacillus borealis*, *Paenibacillus dauci*, *Paenibacillus durus*, *Paenibacillus graminis*, *Paenibacillus larvae*, *Paenibacillus lentimorbus*, *Paenibacillus macerans*, *Paenibacillus mucilaginosus*, *Paenibacillus odorifer*, *Paenibacillus polymyxa*, *Paenibacillus stellifer*, *Paenibacillus terrae*, *Paenibacillus wulumuqiensis*; *Pediococcus* species including *Pediococcus acidilactici*, *Pediococcus claussenii*, *Pediococcus ethanolidurans*, *Pediococcus pentosaceus*; *Salmonella typhimurium*; *Sporolactobacillus* species including *Sporolactobacillus inulinus*, *Sporolactobacillus laevolacticus*; *Staphylococcus aureus*; *Streptococcus* species including *Streptococcus agalactiae*, *Streptococcus bovis*, *Streptococcus equisimilis*, *Streptococcus feacalis*, *Streptococcus mutans*, *Streptococcus oralis*, *Streptococcus pneumonia*, *Streptococcus pyogenes*, *Streptococcus salivarius*, *Streptococcus thermophilus*, *Streptococcus sobrinus*, *Streptococcus uberis*; *Streptomyces* species including *Streptomyces achromogenes*, *Streptomyces avermitilis*, *Streptomyces coelicolor*, *Streptomyces griseus*, *Streptomyces lividans*, *Streptomyces parvulus*, *Streptomyces venezuelae*, *Streptomyces vinaceus*; *Tetragenococcus* species including *Tetragenococcus halophilus* and *Zymomonas* species including *Zymomonas mobilis*.

In a further aspect, a method or use defined herein could be used to modify the genome of yeast or fungi. In particular embodiments, the fungal species are mesophilic, preferably the fungi is selected from: an *Aspergillus* species including, but not limited to, *Aspergillus nidulans*, *Aspergillus niger*, *Aspergillus terreus*, *Aspergillus oryzae* and *Aspergillus terreus*, more preferably the *Aspergillus* species is *Aspergillus nidulans* or *Aspergillus niger*. Alternatively, the mesophilic fungal species could be a *Candida* species.

The invention further relates to use of a method as defined herein to modify a yeast or fungal species that are thermophilic, preferably the fungi or yeast is selected from: *Aspergillus* species including *Aspergillus fumigatus*, *Aspergillus nidulans*, *Aspergillus terreus*, *Aspergillus versicolor*; *Canariomyces* species including *Canariomyces thermophile*; *Chaetomium* species including *Chaetomium mesopotamicum*, *Chaetomium thermophilum*; *Candida* species including *Candida bovina*, *Candida sloofii*, *Candida thermophila*, *Candida tropicalis*, *Candida krusei* (=*Issatchenkia orientalis*); *Cercophora* species including *Cercophora coronate*, *Cercophora septentrionalis*; *Coonemeria* species including *Coonemeria aegyptiaca*; *Corynascus* species including *Corynascus thermophiles*; *Geotrichum* species including *Geotrichum candidum*; *Kluyveromyces* species including *Kluyveromyces fragilis, Kluyveromyces marxianus*; *Malbranchea* species including *Malbranchea cinnamomea, Malbranchea sulfurea*; *Melanocarpus* species including *Melanocarpus albomyces*; *Myceliophtora* species including *Myceliophthora fergusii, Myceliophthora thermophila*; *Mycothermus* species including *Mycothermus thermophiles* (=*Scytalidium thermophilum/Torula thermophila*); *Myriococcum* species including *Myriococcum thermophilum*; *Paecilomyces* species including *Paecilomyces thermophila*; *Remersonia* species including *Remersonia thermophila*; *Rhizomucor* species including *Rhizomucor pusillus, Rhizomucor tauricus*; *Saccharomyces* species including *Saccharomyces cerevisiae, Schizosaccharomyces* species including *Schizosaccharomyces pombe, Scytalidium* species including *Scytalidium thermophilum*; *Sordaris* species including *Sordaria thermophila*; *Thermoascus* species including *Thermoascus aurantiacus, Thermoascus thermophiles*; *Thermomucor* species including *Thermomucor indicae-seudaticae* and *Thermomyces* species including *Thermomyces ibadanensis, Thermomyces lanuginosus*.

In the aforementioned lists, microbes identified in bold typeface have been found to be particularly suitable/applicable in use for the present invention.

Some preferred embodiments of the present invention include one or more thermophilic microbes selected from: Thermophilic bacilli, including *Aeribacillus, Alicyclobacillus, Anoxybacillus, Bacillus, Geobacillus; Paenibacillus* species; *Thermophilic clostridia*, including *Anaerobacter, Anaerobacterium, Caldicellulosiruptor, Clostridium, Moorella, Thermoanaerobacter, Thermoanaerobacterium, Thermobrachium, Thermohalobacter* species or one or more thermophilic *Lactobacillus* species and mesophilic bacteria selected from *Bacillus* species, *Escherichia coli*, and *Lactobacillus* species.

BRIEF DESCRIPTION OF THE FIGURES

The invention will now be described in detail with reference to a specific embodiment and with reference to the accompanying drawings, in which:

FIG. 6 shows an alignment of sequences of the *G. thermodenitrificans* T12 type IIc CRISPR system.

FIG. 7 shows six single hits obtained to provide an in silico PAM prediction for gtCas9.

FIG. 12 shows the results of in vivo genome editing of *Bacillus smithii* ET138 cells using gtCas9 and 8 nt PAM sequences, by the growth or absence of colonies of the

Figure 12:
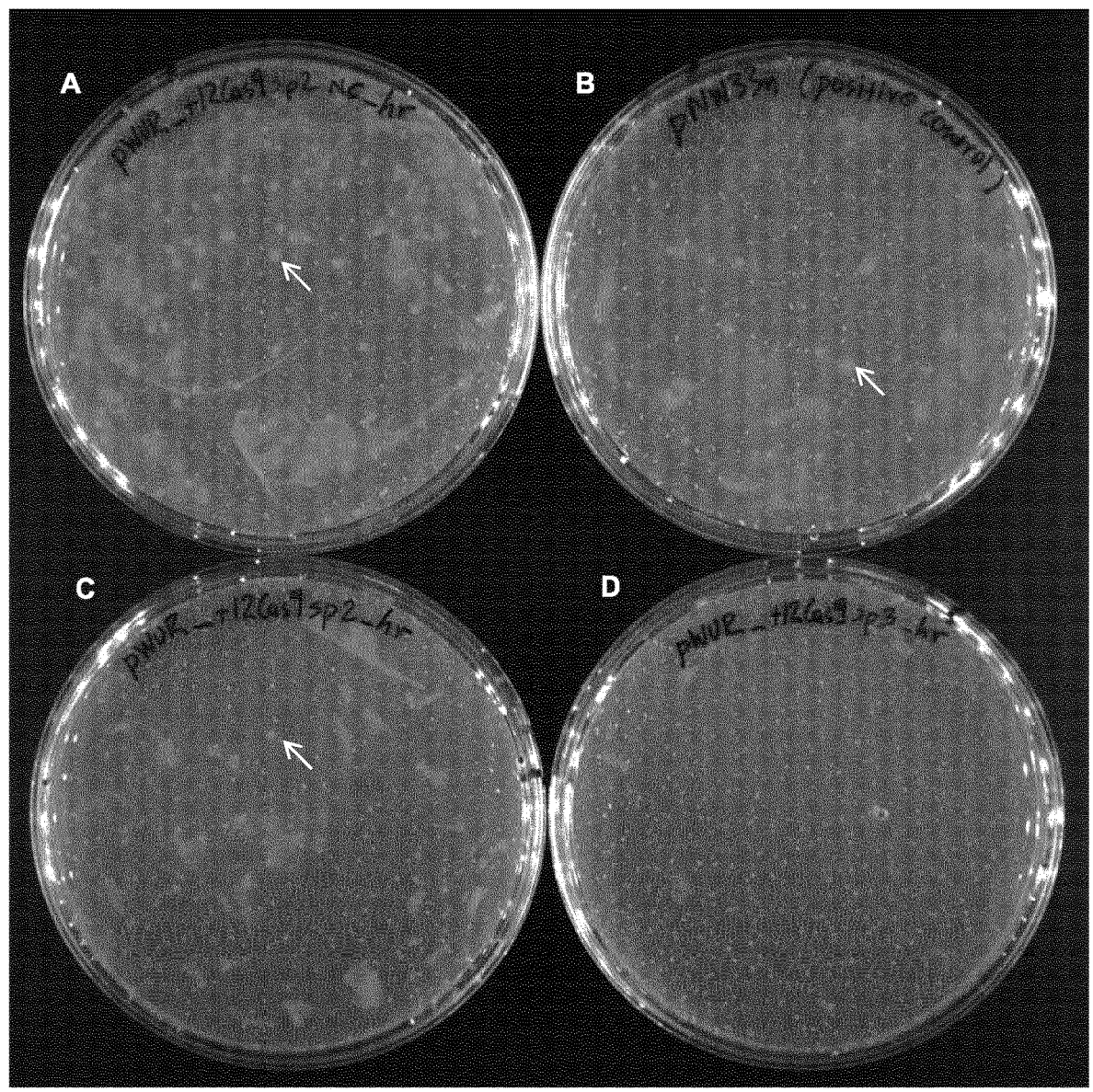

*Bacillus smithii* ET138 cells on selection plates, as explained in Example 9. Colonies are indicated with arrows in FIG. 12.

Figure 13:
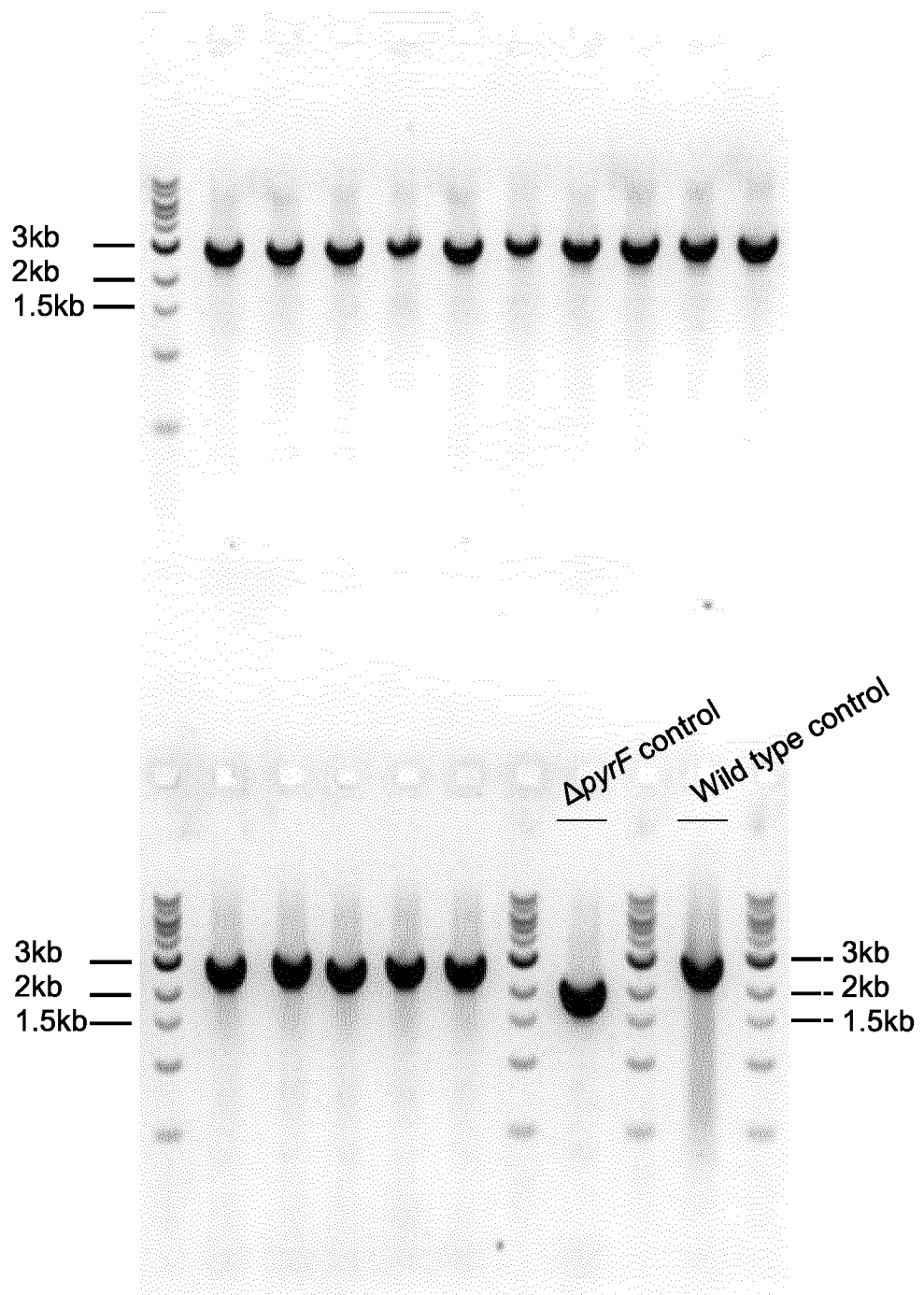

FIG. 13 shows the results of a PCR screen for colonies in which the pyrF gene was deleted. The colonies were generated following transformation of *Bacillus smithii* ET138 cells with construct 3 (negative control). 15 colonies were screened but none showed the deletion genotype –2.1 kb band size and instead all showed the wild type –2.9 kb band size, as explained in Example 9.

Figure 14:
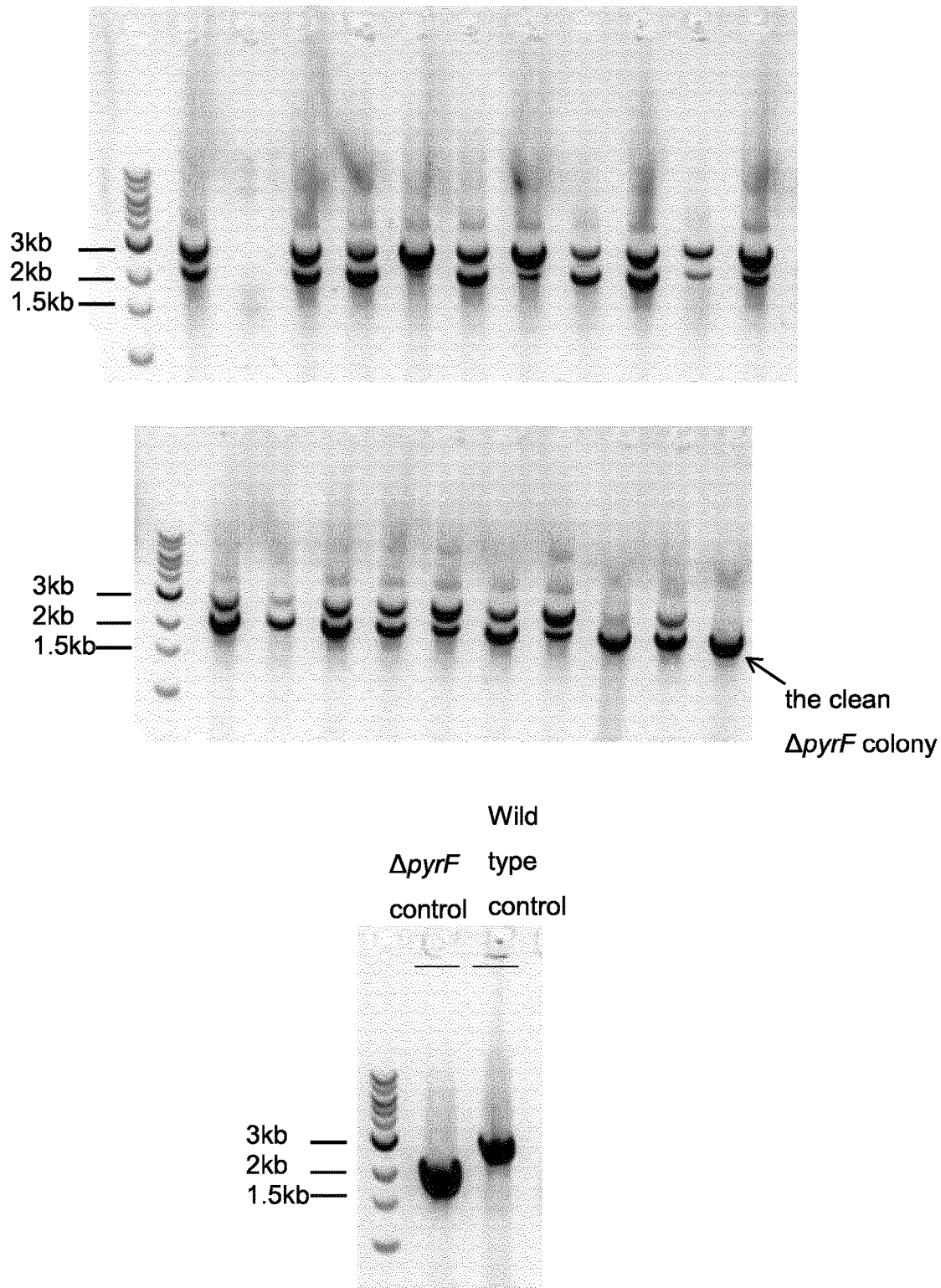

FIG. 14 shows the results of a PCR screen for colonies in which the pyrF gene was deleted. The colonies were generated following transformation of *Bacillus smithii* ET138 cells with construct 1 (PAM sequence ATCCCCAA [SEQ ID NO: 21]). 20 colonies were screened and one showed the deletion genotype –2.1 kb band size whilst the rest showed both the wild type –2.9 kb band size and the deletion genotype –2.1 kb band size, as explained in Example 9. No wild type only genotypes were observed.

Below are polynucleotide and amino acid sequences of Cas proteins used in accordance with the invention.

*Geobacillus thermodenitrificans*
T12 Cas9 protein AA sequence

[SEQ ID NO: 1]

MKYKIGLDIGITSIGWAVINLDIPRIEDLGVRIFDRAENPKTGESLAL

PRRLARSARRRLRRRKHRLERIRRLFVREGILTKEELNKLFEKKHEID

VWQLRVEALDRKLNNDELARILLHLAKRRGFRSNRKSERTNKENSTML

KHIEENQSILSSYRTVAEMVVKDPKFSLHKRNKEDNYTNTVARDDLER

EIKLIFAKQREYGNIVCTEAFEHEYISIWASQRPFASKDDIEKKVGFC

TFEPKEKRAPKATYTFQSFTVWEHINKLRLVSPGGIRALTDDERRLIY

KQAFHKNKITFHDVRTLLNLPDDTRFKGLLYDRNTTLKENEKVRFLEL

GAYHKIRKAIDSVYGKGAAKSFRPIDFDTFGYALTMFKDDTDIRSYLR

NEYEQNGKRMENLADKVYDEELIEELLNLSFSKFGHLSLKALRNILPY

MEQGEVYSTACERAGYTFTGPKKKQKTVLLPNIPPIANPVVMRALTQA

RKVVNAIIKKYGSPVSIHIELARELSQSFDERRKMQKEQEGNRKKNET

AIRQLVEYGLTLNPTGLDIVKFKLWSEQNGKCAYSLQPIEIERLLEPG

YTEVDHVIPYSRSLDDSYTNKVLVLTKENREKGNRTPAEYLGLGSERW

QQFETFVLTNKQFSKKKRDRLLRLHYDENEENEFKNRNLNDTRYISRF

LANFIREHLKFADSDDKQKVYTVNGRITAHLRSRWNFNKNREESNLHH

AVDAAIVACTTPSDIARVTAFYQRREQNKELSKKTDPQFPQPWPHFAD

ELQARLSKNPKESIKALNLGNYDNEKLESLQPVFVSRMPKRSITGAAH

QETLRRYIGIDERSGKIQTVVKKKLSEIQLDKTGHFPMYGKESDPRTY

EAIRQRLLEHNNDPKKAFQEPLYKPKKNGELGPIIRTIKIIDTTNQVI

PLNDGKTVAYNSNIVRVDVFEKDGKYYCVPIYTIDMMKGILPNKAIEP

NKPYSEWKEMTEDYTFRFSLYPNDLIRIEFPREKTIKTAVGEEIKIKD

LFAYYQTIDSSNGGLSLVSHDNNFSLRSIGSRTLKRFEKYQVDVLGNI

YKVRGEKRVGVASSSHSKAGETIRPL*

*Geobacillus thermodenitrificans*
T12 Cas9 DNA Sequence

[SEQ ID NO: 7]

ATGAAGTATAAAATCGGTCTTGATATCGGCATTACGTCTATCGGTTGG

GCTGTCATTAATTTGGACATTCCTCGCATCGAAGATTTAGGTGTCCGC

ATTTTTGACAGAGCGGAAAACCCGAAAACCGGGGAGTCACTAGCTCTT

CCACGTCGCCTCGCCCGCTCCGCCCGACGTCGTCTGCGGCGTCGCAAA

CATCGACTGGAGCGCATTCGCCGCCTGTTCGTCCGCGAAGGAATTTTA

ACGAAGGAAGAGCTGAACAAGCTGTTTGAAAAAAAGCACGAAATCGAC

GTCTGGCAGCTTCGTGTTGAAGCACTGGATCGAAAACTAAATAACGAT

GAATTAGCCCGCATCCTTCTTCATCTGGCTAAACGGCGTGGATTTAGA

TCCAACCGCAAGAGTGAGCGCACCAACAAAGAAAACAGTACGATGCTC

AAACATATTGAAGAAACCAATCCATTCTTTCAAGTTACCGAACGGTT

GCAGAAATGGTTGTCAAGGATCCGAAATTTTCCCTGCACAAGCGTAAT

AAAGAGGATAATTACACCAACACTGTTGCCCGCGACGATCTTGAACGG

GAAATCAAACTGATTTTCGCCAAACAGCGCGAATATGGGAACATCGTT

TGCACAGAAGCATTTGAACACGAGTATATTTCCATTTGGGCATCGCAA

CGCCCTTTTGCTTCTAAGGATGATATCGAGAAAAAAGTCGGTTTCTGT

ACGTTTGAGCCTAAAGAAAAACGCGCGCCAAAAGCAACATACACATTC

CAGTCCTTCACCGTCTGGGAACATATTAACAAACTTCGTCTTGTCTCC

CCGGGAGGCATCCGGGCACTAACCGATGATGAACGTCGTCTTATATAC

AAGCAAGCATTTCATAAAAATAAAATCACCTTCCATGATGTTCGAACA

TTGCTTAACTTGCCTGACGACACCCGTTTTAAAGGTCTTTTATATGAC

CGAAACACCACGCTGAAGGAAAATGAGAAAGTTCGCTTCCTTGAACTC

GGCGCCTATCATAAAATACGGAAAGCGATCGACAGCGTCTATGGCAAA

GGAGCAGCAAAATCATTTCGTCCGATTGATTTTGATACATTTGGCTAC

GCATTAACGATGTTTAAAGACGACACCGACATTCGCAGTTACTTGCGA

AACGAATACGAACAAAATGGAAAACGAATGGAAAATCTAGCGGATAAA

GTCTATGATGAAGAATTGATTGAAGAACTTTTAAACTTATCGTTTTCT

AAGTTTGGTCATCTATCCCTTAAAGCGCTTCGCAACATCCTTCCATAT

ATGGAACAAGGCGAAGTCTACTCAACCGCTTGTGAACGAGCAGGATAT

ACATTTACAGGGCAAAGAAAAAACAGAAAACGGTATTGCTGCCGAAC

ATTCCGCCGATCGCCAATCCGGTCGTCATGCGCGCACTGACACAGGCA

CGCAAAGTGGTCAATGCCATTATCAAAAAGTACGGCTCACCGGTCTCC

ATCCATATCGAACTGGCCCGGGAACTATCACAATCCTTTGATGAACGA

CGTAAAATGCAGAAAGAACAGGAAGGAAACCGAAAGAAAAACGAAACT

GCCATTCGCCAACTTGTTGAATATGGGCTGACGCTCAATCCAACTGGG

CTTGACATTGTGAAATTCAAACTATGGAGCGAACAAAACGGAAAATGT

GCCTATTCACTCCAACCGATCGAAATCGAGCGGTTGCTCGAACCAGGC

TATACAGAAGTCGACCATGTGATTCCATACAGCCGAAGCTTGGACGAT

AGCTATACCAATAAAGTTCTTGTGTTGACAAAGGAGAACCGTGAAAAA

GGAAACCGCACCCCAGCTGAATATTTAGGATTAGGCTCAGAACGTTGG

-continued

```
CAACAGTTCGAGACGTTTGTCTTGACAAATAAGCAGTTTTCGAAAAAG

AAGCGGGATCGACTCCTTCGGCTTCATTACGATGAAAACGAAGAAAAT

GAGTTTAAAAATCGTAATCTAAATGATACCCGTTATATCTCACGCTTC

TTGGCTAACTTTATTCGCGAACATCTCAAATTCGCCGACAGCGATGAC

AAACAAAAAGTATACACGGTCAACGGCCGTATTACCGCCCATTTACGC

AGCCGTTGGAATTTTAACAAAAACCGGGAAGAATCGAATTTGCATCAT

GCCGTCGATGCTGCCATCGTCGCCTGCACAACGCCGAGCGATATCGCC

CGAGTCACCGCCTTCTATCAACGGCGCGAACAAAACAAAGAACTGTCC

AAAAAGACGGATCCGCAGTTTCCGCAGCCTTGGCCGCACTTTGCTGAT

GAACTGCAGGCGCGTTTATCAAAAAATCCAAAGGAGAGTATAAAAGCT

CTCAATCTTGGAAATTATGATAACGAGAAACTCGAATCGTTGCAGCCG

GTTTTTGTCTCCCGAATGCCGAAGCGGAGCATAACAGGAGCGGCTCAT

CAAGAAACATTGCGGCGTTATATCGGCATCGACGAACGGAGCGGAAAA

ATACAGACGGTCGTCAAAAAGAAACTATCCGAGATCCAACTGGATAAA

ACAGGTCATTTCCCAATGTACGGGAAAGAAAGCGATCCAAGGACATAT

GAAGCCATTCGCCAACGGTTGCTTGAACATAACAATGACCCAAAAAAG

GCGTTTCAAGAGCCTCTGTATAAACCGAAGAAGAACGGAGAACTAGGT

CCTATCATCCGAACAATCAAAATCATCGATACGACAAATCAAGTTATT

CCGCTCAACGATGGCAAAACAGTCGCCTACAACAGCAACATCGTGCGG

GTCGACGTCTTTGAGAAAGATGGCAAATATTATTGTGTCCCTATCTAT

ACAATAGATATGATGAAAGGGATCTTGCCAAACAAGGCGATCGAGCCG

AACAAACCGTACTCTGAGTGGAAGGAAATGACGGAGGACTATACATTC

CGATTCAGTCTATACCCAAATGATCTTATCCGTATCGAATTTCCCCGA

GAAAAAACAATAAAGACTGCTGTGGGGAAGAAATCAAAATTAAGGAT

CTGTTCGCCTATTATCAAACCATCGACTCCTCCAATGGAGGGTTAAGT

TTGGTTAGCCATGATAACAACTTTTCGCTCCGCAGCATCGGTTCAAGA

ACCCTCAAACGATTCGAGAAATACCAAGTAGATGTGCTAGGCAACATC

TACAAAGTGAGAGGGGAAAAGAGAGTTGGGGTGGCGTCATCTTCTCAT

TCGAAAGCCGGGGAAACTATCCGTCCGTTATAA
```

DETAILED DESCRIPTION

Example 1: Isolation of *Geobacillus thermodenitrificans*

*G. thermodenitrificans* was surprisingly discovered during a search of a library of ±500 isolates for a thermophile capable of degrading lignocellulosic substrates under anaerobic conditions. At first a library of ±500 isolates was established which, after several selection rounds by isolation on cellulose and xylan, was trimmed down to 110 isolates. This library of 110 isolates consisted solely of *Geobacillus* isolates with *G. thermodenitrificans* representing 79% of the library.

The isolated *G. thermodenitrificans* strain has been named "T12". The Cas9 protein from *G. thermodenitrificans* T12 has been named "gtCas9".

Example 2: Defining the Essential Consensus Sequences for Cas9 in *Geobacillus thermodenitrificans*

The following database searches and alignments were performed:
pBLAST and nBLAST were performed on the in-house BLAST server, in which either the protein or gene sequence of *G. thermodenitrificans* T12 was used as query sequence. This database was last updated May 2014 and therefore does not contain the most recently added *Geobacillus* genomes, but normal online BLAST was not used to prevent publication of the T12 sequence. Sequence identities found to be greater than 40% in the BLAST search are included in FIG. 1.

To include more recent sequence data, the sequence of *Geobacillus* MAS1 (most closely related to gtCas9) was used to perform a PSI-BLAST on the NCBI website (Johnson et al., 2008 Nucleic Acids Res. 36 (Web Server issue): W5-9). Two consecutive rounds of PSI-BLAST were performed, in which only sequences that met the following criteria were used for the next round: minimum sequence coverage of 96% in the first round and 97% in the second and third round, minimum identity 40%, only one strain per species.

Figure 1:
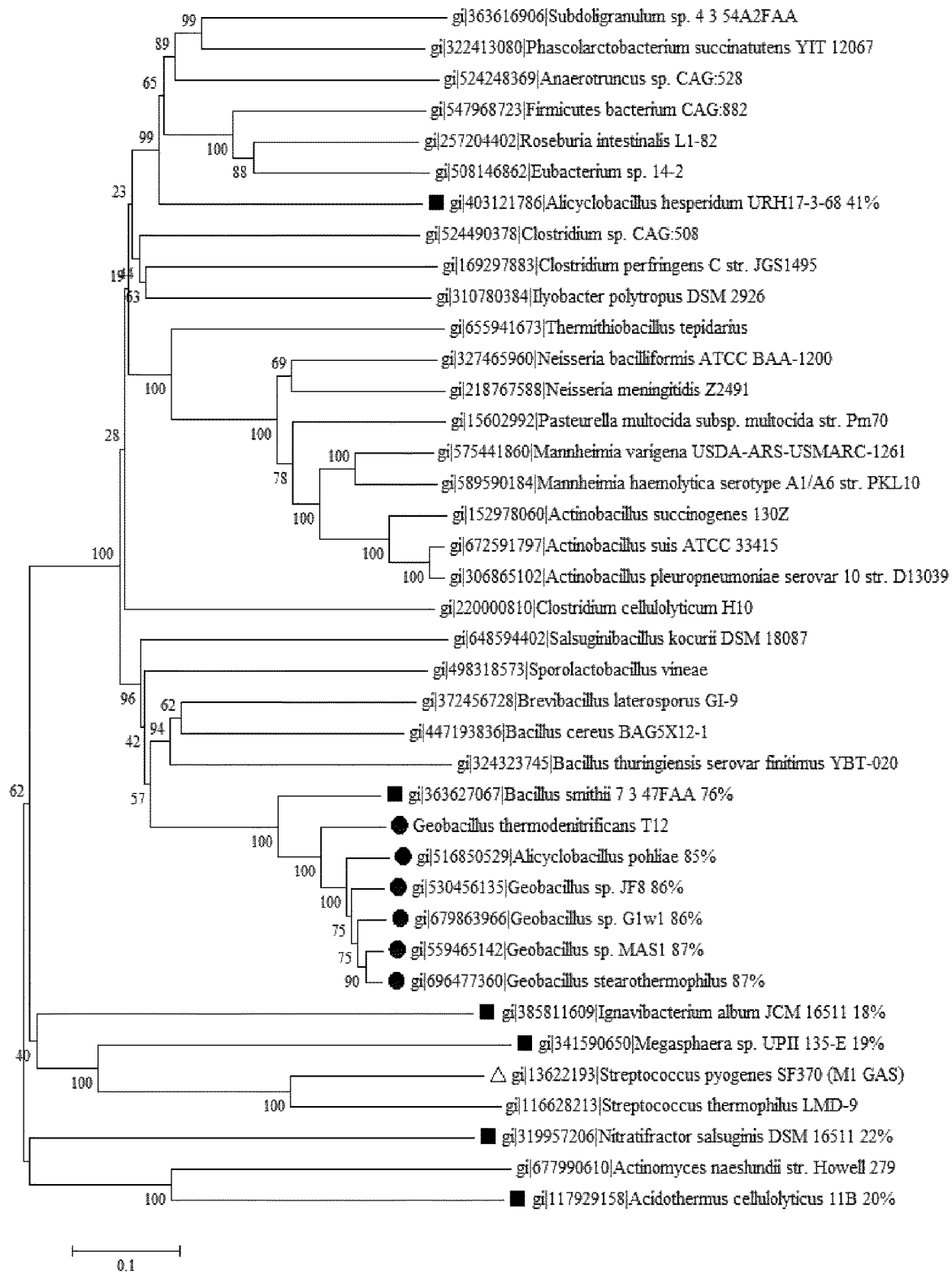
FIG. 1 shows a Neighbour-Joining tree of Cas9 protein sequences. All sequences having a sequence similarity above 40% with strain T12 based on pBLAST or PSI-BLAST were included, as well as currently well-characterized sequences (*S. pyogenes, S. thermophiles* and *A. naeslundii*), as well as all currently identified thermophilic sequences also when these were below 40% identity. For all thermophilic sequences, the percentage identity to T12 is indicated after the strain name. Gene identifier (gi) numbers are indicated before the species name. Legend: Closed circles: thermophilic (optimum above 60° C.) Cas9 sequences, closed squares: thermotolerant (optimum <50° C.) Cas9 sequences, open triangle: Cas9 sequence currently most used for genome editing purposes from mesophilic origin; no sign: mesophilic Cas9. Values at the nodes represent 1000-replicate bootstrap values; scale bar represents estimated amino acid substitutions per site.

The sequences resulting from the PSI-BLAST, as well as the sequences with more than 40% identity to T12 from the internal server pBLAST that did not appear in the PSI-BLAST were aligned together with currently well-characterized mesophilic sequences and all currently identified thermophilic sequences also if these were more distantly related, from which a Neighbour-Joining tree was constructed (see FIG. 1). Alignment was performed in Mega6 using ClustalW, after which a tree was constructed using the Neighbour-Joining method and bootstrap analysis was performed using 1000 replicates.

Figure 2:
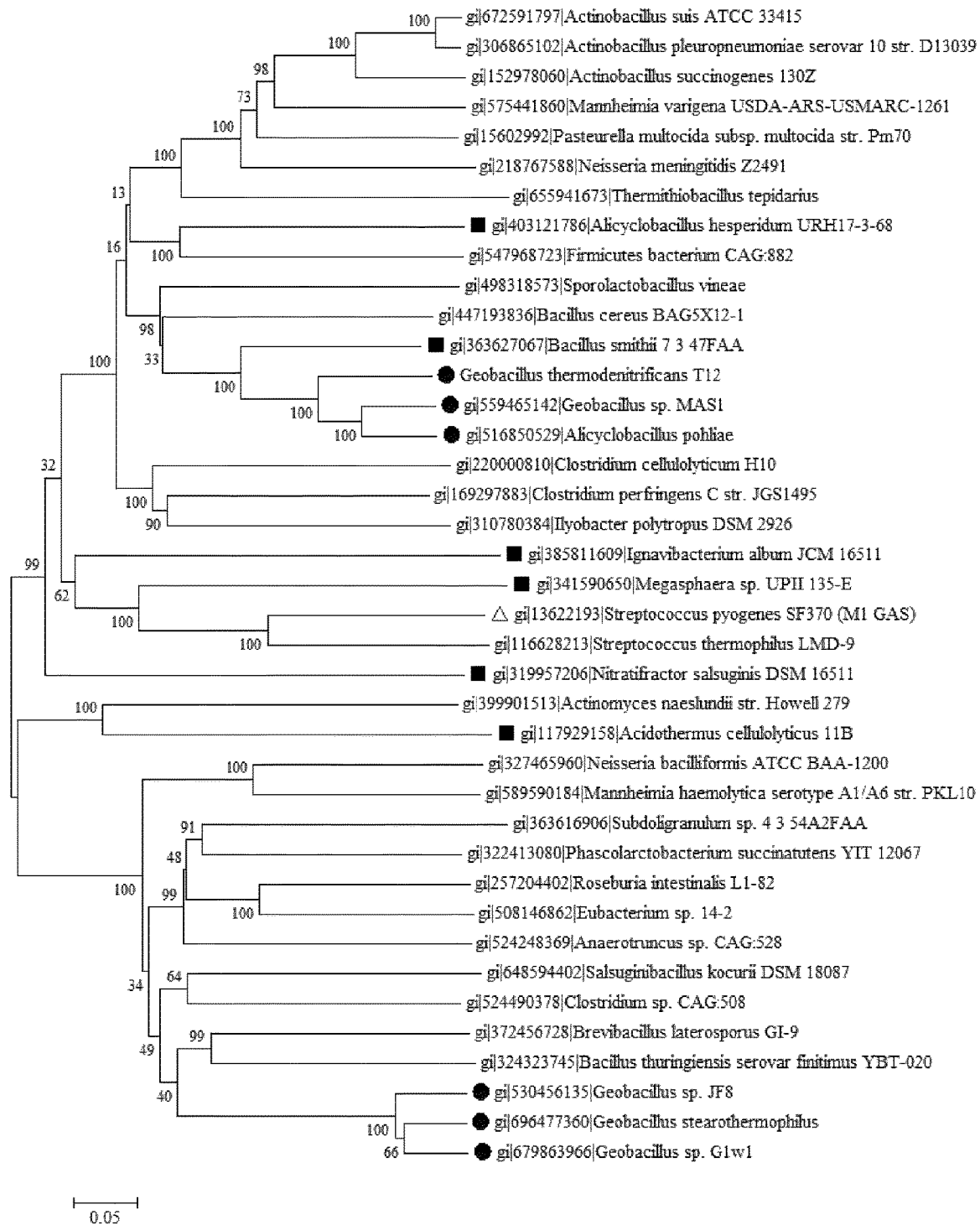
FIG. 2 shows a Neighbour-Joining tree of Cas9 gene sequences. Identity at the gene level was extremely poor; sequences from the same organisms as those used for the protein alignment were used for the gene alignment. Gene identifier (gi) numbers are indicated before the species name. Legend: Closed circles: thermophilic (optimum above 60° C.) Cas9 sequences, closed squares: thermotolerant (optimum <50° C.) Cas9 sequences, open triangle: Cas9 sequence currently most used for genome editing purposes from mesophilic origin; no sign: mesophilic Cas9. Values at the nodes represent 1000-replicate bootstrap values.

When BLASTn was performed using *Geobacillus* sp. MAS1 as the query sequence, only *Geobacillus* sp. JF8 Cas9 was identified with 88% identity, indicating very little homology at the gene level. FIG. 2 is a Neighbour-Joining tree of Clustal-aligned Cas9 gene sequences.

Protein sequences of *G. thermodenitrificans* T12, *A. naeslundii* and *S. pyogenes* were further analyzed for protein domain homology (see FIG. 3) by aligning them in Clone-Manager using BLOSUM62 with default settings.

Figure 3:
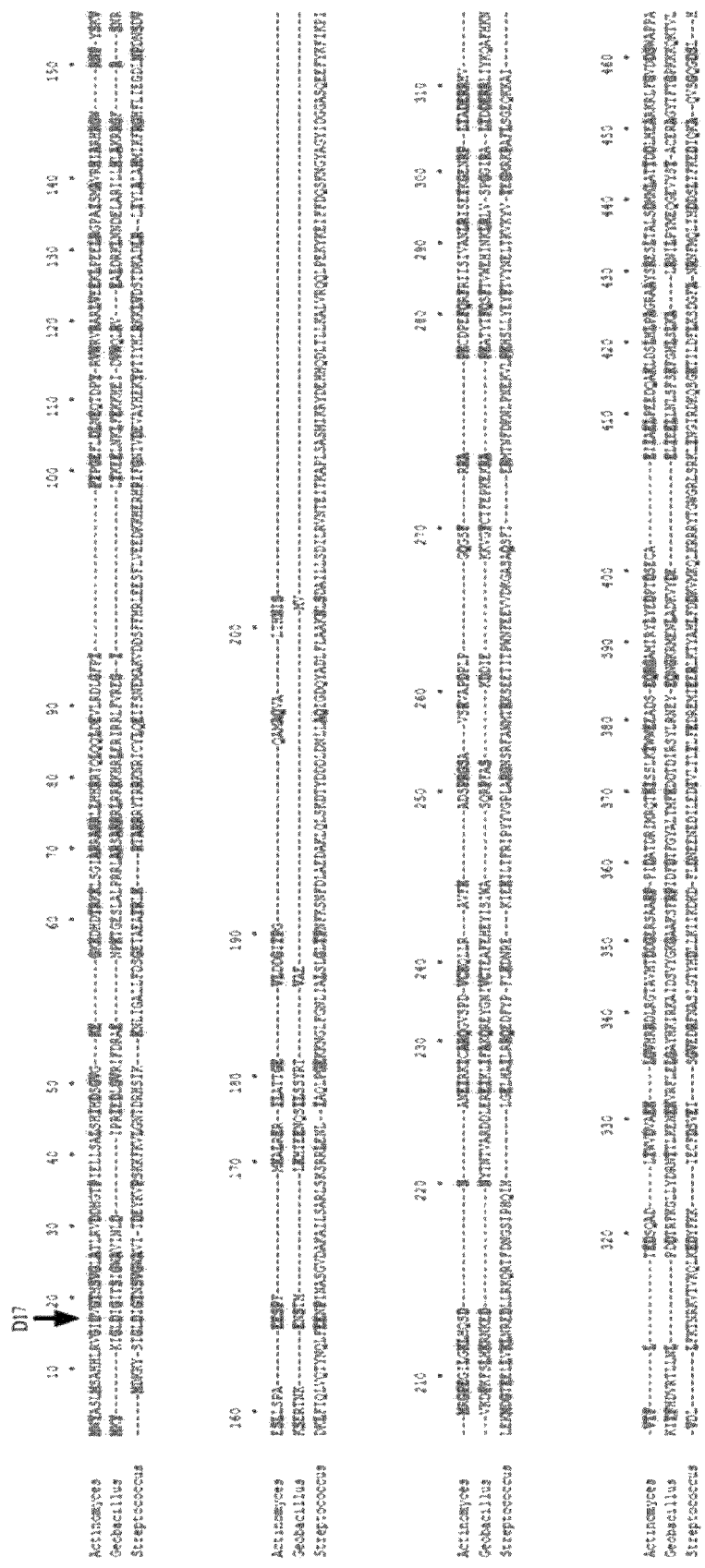
FIG. 3 shows a protein sequence alignment for gtCas9 (SEQ ID NO: 1) (Type II-C) with well-characterized Type II-C (*A. naeslundii*/'ana'; SEQ ID NO: 8) and Type II-A (*S. pyogenes*/'pyo'; SEQ ID NO: 9 and *S. thermophilus*) Cas9 sequences. Important active site residues are well conserved and indicated with black arrows. Protein domains as described for Ana-Cas9 and Pyo-Cas9 (Jinek, et al., 2014, Science 343: 1247997) are indicated with shaded boxes and similarly coloured letters. The PAM recognition domain has been determined for the *S. pyogenes* Type II-A system but not for any Type II-C system and is therefore only indicated in the *S. pyogenes* sequence.
Figure 3:
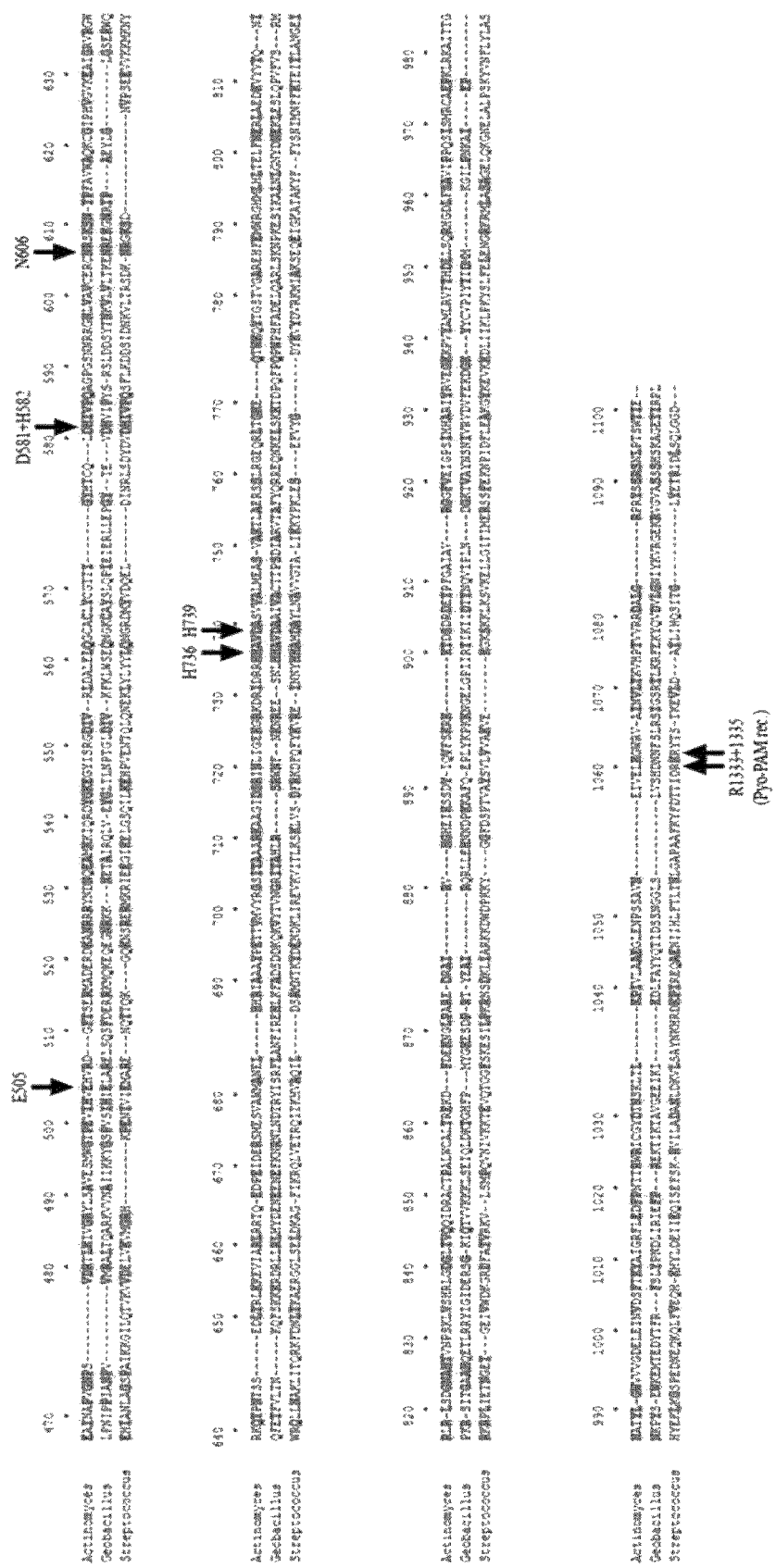
Figure 4:
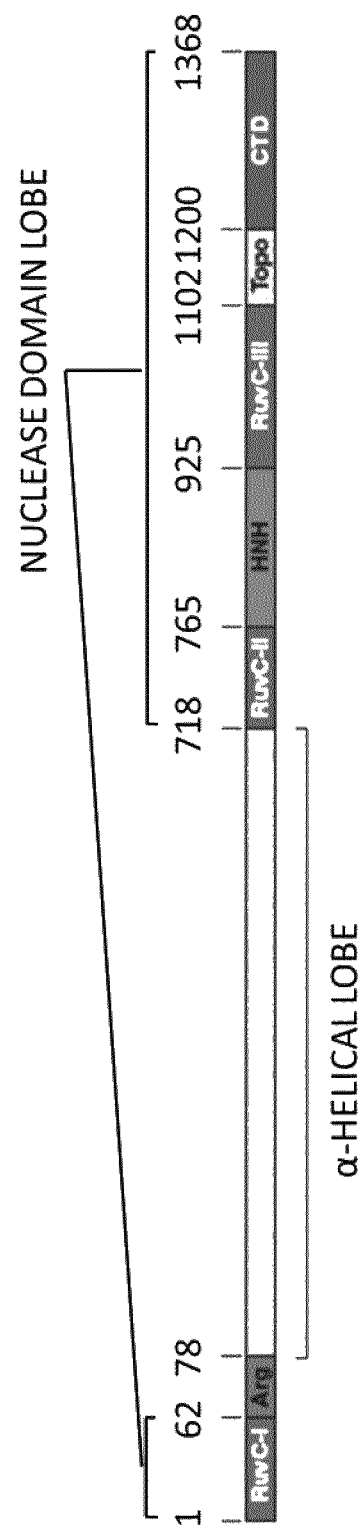
FIG. 4 shows protein architecture of *A. naeslundii* Cas9 (Cas9-Ana) (Jinek et al., 2014). gtCas9 belongs to the same Type II-C CRISPR system and active site residues could be identified.
Figure 5:
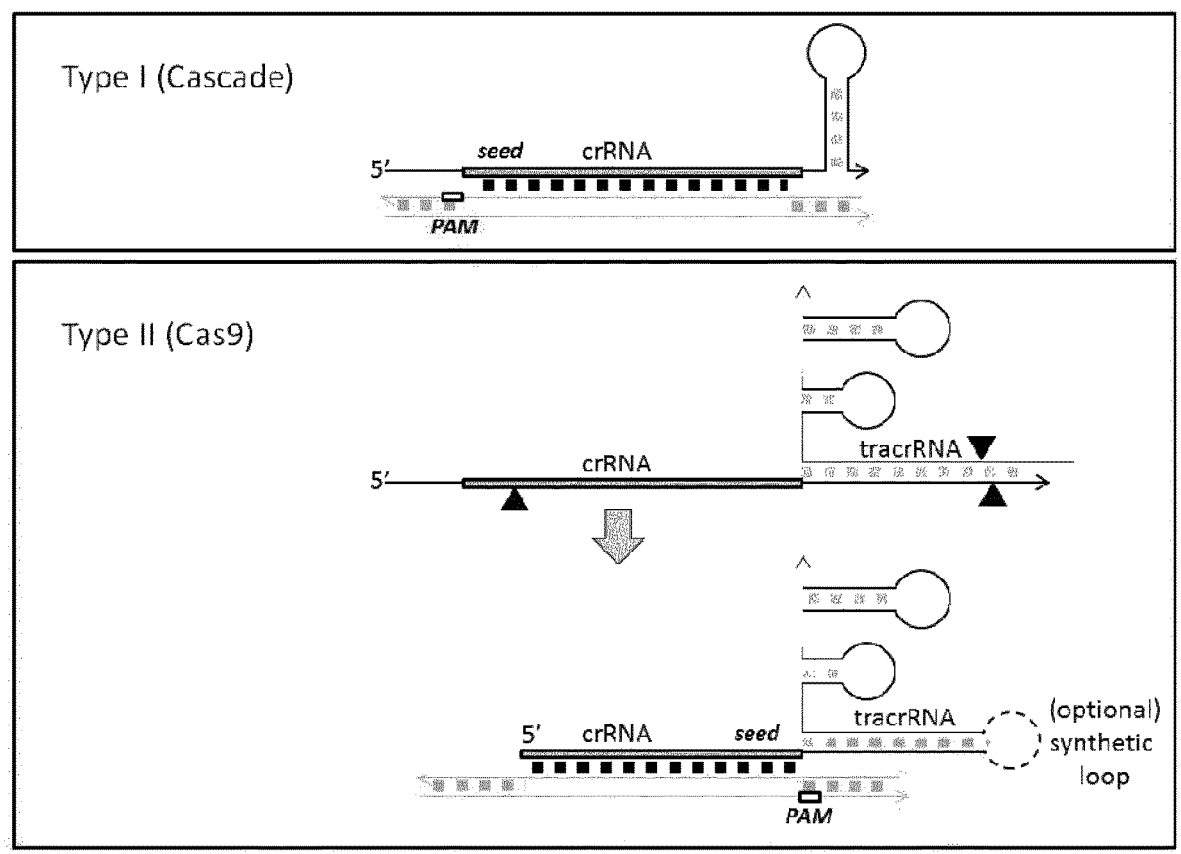
FIG. 5 shows a comparison of crRNA-guided targeting of complementary dsDNA. Base pairing is indicated with dashed lines. RNA is depicted in black, DNA in grey. Base pairing between crRNA spacer and target protospacer is indicated with thick black dashed line, base pairing between DNA strands and between RNA strands is indicated with thick grey dashed lines. The 5' end of the crRNA is indicated. Note that PAM (small white box) in Type I resides downstream of target strand (protospacer), whereas in Type II it resides at the other end on the displaced strand. Likewise, the seed (the predicted sequence of the guide where base pairing with target DNA strand starts, and where no mismatches are allowed) is located close to the PAM, and as such differs in types I and II (Van der Oost, 2014 ibid.). Panel A shows a schematic of a Type I Cascade system of *E. coli*. crRNA has internal spacer (grey box, 31-32 nt that allows for target recognition), flanked bt a 8 nt 5' handle and a 29 nt 3' handle that consists of a stem-loop structure (hairpin) (Jore 2011 ibid.). Panel B shows a schematic of a Type II Cas9 system of *S. pyogenes*. crRNA basepairs with tracrRNA, that allows for processing by RNaseIII (opposite black triangles). Additionally, the 5' end of the crRNA is trimmed by an RNase (black triangle), typically resulting in a 20 nt spacer. Note that a synthetic loop may be introduced to link the crRNA and tracrRNA, resulting in a single guide RNA (sgRNA) (Jinek et al., 2012 ibid.).

Example 3: Identifying Core Amino Acid Motifs which are Essential for the Function of CAS9 and Those which Confer Thermostability in Thermophilic Cas9 Nucleases Percentages identity of the above described aligned protein sequences are provided in FIG. 1. gtCas9 belongs to Type II-C. The best-studied and recently crystallized structure of a Type II-C system is from *Actinomyces naeslundii* (Jinek et al., 2014, Science 343: 1247997). This protein sequence shows only 20% identity to gtCas9 but can be used to estimate highly conserved residues. Two well-characterized Type II-A systems (*S. pyogenes* and *S. thermophilus*) were also included in the analyses (Jinek et al., 2014, Science 343: 1247997; Nishimasu et al., 2014, Cell 156: 935-949). Alignments of these four protein sequences are shown in FIG. 3; FIG. 4 shows the protein architecture as determined for *A. naeslundii* ('Ana-Cas9') (Jinek et al., 2014, Science 343: 1247997). The length of Cas9 from t12 (gtCas9) and *Actinomyces naeslundii* is highly similar (*A. naeslundii* 1101 aa, gtCas9 1082 aa) and gtCas9 is expected to have similar protein architecture but this remains to be determined, as the overall sequence identity to cas9-Ana is only 20%. All active side residues described by Jinek et al. (Jinek et al., 2014, Science 343: 1247997) in Cas9 from *A. naeslundii* and *S. pyogenes* could be identified in gtCas9 (see FIG. 3). The PAM-binding domain has been determined for the *S. pyogenes* Type II-A system but not for any Type II-C system and is therefore only indicated in the *S. pyogenes* sequence. Moreover, the PAM-recognition site varies strongly, not only between CRISPR systems but also between species containing the same system.

Example 4: Determination of the PAM Sequence of *G. thermodenitrificans* gtCas9

It has been established that the prokaryotic CRISPR systems serve their hosts as adaptive immune systems (Jinek et al., 2012, Science 337: 816-821) and can be used for quick and effective genetic engineering (Mali et al., 2013, Nat Methods 10: 957-963.).

Cas9 proteins function as sequence-specific nucleases for the type II CRISPR systems (Makarova et al., 2011, Nat Rev Micro 9: 467-477). Small crRNA molecules, which consist of a "spacer" (target) linked to a repetition region, are the transcription and processing products of a CRISPR loci. "Spacers" naturally originate from the genome of bacteriophages and mobile genetic elements, but they can also be designed to target a specific nucleotide sequence during a genetic engineering process (Bikard et al., 2013, Nucleic Acids Research 41: 7429-7437). The crRNA molecules are employed by the Cas9 as guides for the identification of their DNA targets. The spacer region is identical to the targeted for cleavage DNA region, the "protospacer" (Brouns et al., 2012, Science 337: 808-809). A PAM (Protospacer Adjacent Motif), next to the protospacer, is required for the recognition of the target by the Cas9 (Jinek et al., 2012, Science 337: 816-821).

In order to perform in vitro or in vivo PAM-determination studies for Type II systems, it is necessary to in silico predict the CRISPR array of the system, the tracrRNA-expressing module. The CRISPR array is used for the identification of the crRNA module. The tracrRNA-expressing sequence is located either within a 500 bp-window flanking Cas9 or between the Cas genes and the CRISPR locus (Chylinski, K., et al. (2014) Classification and evolution of type II CRISPR-Cas systems. *Nucleic Acids Res.* 42, 6091-6105). The tracrRNA should consist of a 5'-sequence with high level of complementarity to the direct repeats of the CRISPR array, followed by a predicted structure of no less than two stem-loop structures and a Rho-independent transcriptional termination signal (Ran, F. A., et al. (2015) In vivo genome editing using *Staphylococcus aureus* Cas9. Nature 520, 186-191). The crRNA and tracrRNA molecule can then be used to design a chimeric sgRNA module. The 5'-end of the sgRNA consists of a truncated 20 nt long spacer followed by the 16-20 nt long truncated repeat of the CRISPR array. The repeat is followed by the corresponding truncated anti-repeat and the stem loop of the tracrRNA module. The repeat and anti-repeat parts of the sgRNA are generally connected by a GAAA linker (Karvelis, T., et al. (2015) Rapid characterization of CRISPR-Cas9 protospacer adjacent motif sequence elements. Genome Biol. 16, 253).

The cas genes (the cas9 followed by the cas1 and the cas2 genes) of the *G. thermodenitrificans* T12 type IIc CRISPR system are transcribed using the antisense strand of the T12 chromosome. The cas2 gene is followed by a 100 bp long DNA fragment which upon transcription forms an RNA structure with multiple loops. This structure obviously acts as a transcriptional terminator.

A CRISPR array with 11 repeats and 10 spacer sequences is located upstream of the transcriptional termination sequence and the leader of the array is located at the 5' end of the array. The DNA locus which is transcribed into the tracrRNA is expected to be downstream of the cas9 gene. The alignment of the 325 bp long sequence right downstream of the cas9 gene with the 36 bp long repeat from the CRISPR array revealed that there is a 36 bp long sequence in the tracrRNA locus almost identical to the repeat (shown in FIG. 6). This result led us to the conclusion that the direction of the transcription of the tracrRNA locus should be opposite to the direction of the transcription of the CRISPR array. Consequently the 5'-end of the tracrRNA will be complementary to the 3'-end of the crRNA, leading to the formation of the—required by the Cas9-dual-RNA molecule.

Example 5: Target Generation with Randomized PAM

Two different spacers from the CRISPR II loci of the *G. thermodenitrificans* T12 strain were amplified by PCR using the *G. thermodenitrificans* T12 genomic DNA as template. Two pairs of degenerate primers were used for the amplification of each spacer:

Firstly, a pair that cause the introduction of six random nucleotides upstream of the "protospacer" fragment were used, leading to the production of a pool of protospacers with randomized PAM sequences.

Secondly, a pair that cause the introduction of six random nucleotides downstream of the "protospacer" fragment were used, leading to the production of a pool of protospacers with randomized PAM sequences.

The produced fragments were ligated to the pNW33n vector, producing 4 pools of "protospacer" constructs, with all the possible 4096 different combinations of 6-nucleotide long PAMs each. The assembled DNA was used for the transformation of *G. thermodenitrificans* T12 cells. The cells were plated on chloramphenicol selection and more than $2 \times 10^6$ cells from each protospacer pool will be pooled. The plasmid DNA was extracted from the pools, the target region will be PCR amplified and the products sent for deep sequencing. The PAMs with the fewest reads will be considered active and the process will be repeated only with pNW33n constructs that contain spacers with these PAMs. Reduced transformation efficiency of the *G. thermodenitrificans* T12 will confirm the activity of the PAMs.

Example 6: In Vitro Determination of PAM Sequences for gtCas9

Construction of the pRham:Cas9$_{gt}$ Vector

The cas9$_{gt}$ gene was PCR amplified from the *G. thermodenitrificans* T12 genome, using the BG6927 and BG6928 primers, and combined with the pRham C-His Kan Vector (Lucigen) in one mixture. The mixture was used for transforming *E. cloni* thermo-competent cells according to the provided protocol. 100 µl from the transformation mixture were plated on LB+50kanamycin plates for overnight growth at 37° C. Out of the formed *E. cloni*::pRham:cas9$_{gt}$ single colonies 3 were randomly selected and inoculated in 10 ml LB medium containing 50 µg/ml kanamucin. Glycerol stocks were prepared from the cultures by adding sterile glycerol to 1 ml from each culture up to a final concentration of 20% (v/v). The glycerol stocks were stored at −80° C. The remaining 9 ml from each culture were used for plasmid isolation according to the "GeneJET Plasmid Miniprep Kit" (Thermoscientific) protocol. The plasmids were sent for sequence verification of the cas9$_{gt}$ and one of the plasmids was verified to contain the gene with the right sequence. The corresponding culture was further used for heterologous expression and purification of the gtCas9.

Heterologous Expression of gtCas9 in *E. cloni*::pRham: Cas9$_{gt}$ Vector

An *E. cloni*::pRham:cas9$_{gt}$ preculture was prepared after inoculating 10 ml LB+50kanamycin with the corresponding glycerol stocks. After overnight growth at 37° C. and 180 rpm, 2 ml from the preculture were used for inoculating 200 ml of LB+50kanamycin medium. The *E. cloni*::pRham:cas9$_{gt}$ culture was incubated at 37° C., 180 rpm until an OD$_{600}$ of 0.7. The gtCas9 expression was then induced by adding L-rhamnose to a final concentration of 0.2% w/v. The expression was allowed to proceed for 8 h, after which the cultures were centrifuged for 10 minutes at 4700 rpm, 4° C. to harvest the cells. The medium was discarded and the pelleted cells were either stored at −20° C. or used for the preparation of the cell free extract (CFE) according to the following protocol:
1. Resuspend the pellet in 20 ml Sonication Buffer (20 mM Sodium Phosphate buffer (pH=7.5), 100 mM NaCl, 5 mM MgCl2, 5% (v/v) Glycerol, 1 mM DTT)
2. Disrupt 1 ml of cells by sonication (8 pulses of 30 seconds, cool for 20 seconds on ice in between)
3. Centrifuge for 15 minutes at 35000 g, 4° C. in order to precipitate insoluble parts
4. Remove the supernatant and store it at 4° C. or on ice Designing and Construction of the PAM Library Targeting sgRNA Module for gtCas9

After in silico determination of the tracrRNA expressing DNA module in the genome of *G. thermodenitrificans* T12 strain (see Example 4 above), a single guide (sg)RNA expressing DNA module that combines the crRNA and tracrRNA modules of the CRISPR/Cas9 system in a single molecule was designed. The spacer at the 5'-end of the sgRNA was designed to be complementary to the protospacer of the plasmid library and the module was set under the transcriptional control of a T7 promoter. The pT7_sgRNA DNA module was synthesized by Baseclear and received in a pUC57 vector, forming the pUC57: pT7_sgRNA vector. DH5α competent *E. coli* cells (NEB) were transformed with the vector and the transformation mixture was plated on LB-agar plates containing 100 µg/ml ampicillin. The plates were incubated overnight at 37° C. Three of the formed single colonies were inoculated in 10 ml LB medium containing 100 µg/ml ampicillin. Glycerol stocks were prepared from the cultures by adding sterile glycerol to 1 ml from each culture up to a final concentration of 20% (v/v). The glycerol stocks were stored at −80° C. The remaining 9 ml from each culture were used for plasmid isolation according to the "GeneJET Plasmid Miniprep Kit" (Thermoscientific) protocol. The isolated plasmid was used as a PCR template for amplification of the pT7_sgRNA module. The 218 bp long pT7_sgRNA DNA module (of which the first 18 bp correspond to the pT7) was obtained using the primers BG6574 and BG6575. The complete PCR mixture was run on a 1.5% agarose gel. The band with the desired size was excised and purified according to the "Zymoclean™ Gel DNA Recovery Kit" protocol.

In vitro transcription (IVT) was performed using the "HiScribe™ T7 High Yield RNA Synthesis Kit" (NEB). The purified pT7_sgRNA DNA module was used as template. The IVT mixture was mixed with an equal volume of RNA loading dye (NEB) and heated at 70° C. for 15 minutes in order to disrupt the secondary structure. The heat treated IVT mixture was run on a denaturing Urea-PAGE and the resulting polyacrylamide gel was embaptised for 10 minutes in 100 ml 0.5×TBE buffer containing 10 µl of SYBR Gold (Invitrogen) for staining purposes. The band at the desired size (200 nt) was excised and the sgRNA was purified according to the following RNA purification protocol:
1. Cut RNA gel fragments with a scalpel and add 1 ml of RNA elution buffer, leave overnight at room temperature.
2. Divide 330 µl aliquots into new 1.5 ml tubes.
3. Add 3 volumes (990 µl) of pre-chilled (−20° C.) 100% EtOH.
4. Incubate for 60 minutes at −20° C.
5. Centrifuge for 20 minutes at 13000 rpm in a microfuge at room temperature.
6. Remove EtOH, wash pellet with 1 ml 70% EtOH.
7. Centrifuge for 5 minutes at 13000 rpm in a microfuge at room temperature.
8. Remove 990 µl of the supernatant.
9. Evaporate the rest EtOH in a thermomixer at 55° C. for 15 to 20 minutes.
10. Resuspend pellet in 20 µl MQ, store at −20° C.

Designing and Construction of a 7 nt Long PAM Library, and Linearization of the Library The design and construction of the PAM library was based on the pNW33n vector. A 20 bp long protospacer was introduced to the vector, flanked at its 3'side by a 7 degenerate nucleotides long sequence; the degenerate sequence serves as the PAM and when the protospacer is flanked by a right PAM then it can be recognized as a target by an sgRNA loaded Cas9 and cleaved. The PAM library was prepared according to the following protocol:
1. Prepare the SpPAM double stranded DNA insert by annealing the single stranded DNA oligos 1 (BG6494) and 2 (BG6495)
   I. 10 µl 10×NEBuffer 2.1
   II. 1 µl 50 µM oligo 1 (~1.125 µg)
   II. 1 µl 50 µM oligo 2 (~1.125 µg)
   IV. 85 µl MQ
   V. Incubate the mixture at 94° C. for 5 min and cool down to 37° C. at a rate of 0.03° C./sec
2. Add 1 µl Klenow 3'→5' exo-polymerase (NEB) to each annealed oligos mixture and then add 2.5 µl of 10 µM dNTPs. Incubate at 37° C. for 1 h and then at 75° C. for 20 min.
3. Add 2 µl of the HF-BamHI and 2 µl of the BspHI restriction enzymes to 46 µl of the annealing mixture. Incubate at 37° C. for 1 h. This process will lead to the SpPAMbb insert with sticky ends. Use the Zymo DNA cleaning and concentrator kit (Zymo Research) to clean the created insert.
4. Digest pNW33n with the HF-BamHI and BspHI (NEB) and purify the 3.400 bp long linear pNW33nbb fragment with sticky ends, using the Zymo DNA cleaning and concentrator kit (Zymo Research).
5. Ligate 50 ng of pNW33nBB with 11 ng of the SPPAMbb insert using the NEB T4 ligase according to the provided protocol. Purify the ligation mixture using the Zymo DNA cleaning and concentrator kit (Zymo Research).
6. Transform DH10b electro-competent cells (200 µl of cells with 500 ng of DNA). Recover the cells in SOC medium (200 µl cells in 800 µl SOC) for an hour and then inoculate 50 ml of LB+12.5 µg/ml chloramphenicol with the recovered cells. Incubate overnight the culture at 37° C. and 180 rpm.
7. Isolate plasmid DNA from the culture using the JetStar 2.0 maxiprep kit (GENOMED).
8. Use the SapI (NEB) restriction according to the provided protocol for linearizing the isolated plasmids.

Designing and Execution of the PAM Determination Reactions

The following cleavage reaction was set up for gtCas9-induced introduction of dsDNA breaks to the PAM library members that contain the right PAM downstream of the 3' end of the targeted protospacer:

1. 2.5 µg of E. cloni::pRham:cas9$_{gt}$ CFE per reaction
2. sgRNA to 30 nM final concentration
3. 200 ng of linearized PAM library per reaction
4. 2 µl of cleavage buffer (100 mM Sodium Phosphate buffer (pH=7.5), 500 mM NaCl, 25 mM MgCl2, 25% (v/v) Glycerol, 5 mM DTT)
5. MQ water up to 20 µl final volume The reaction was incubated for 1 h at 60° C. and stopped after adding 4 µl of 6× gel loading dye (NEB). The reaction mixture was then loaded to a 1% agarose gel. The gel was subjected to an 1 h and 15 min long electrophoresis at 100V and then it was incubated for 30 min in 100 ml 0.5×TAE buffer containing 10 µl of SYBR Gold dye (ThermoFisher). After visualizing the DNA bands with blue light, the band that corresponded to the successfully cleaved and PAM containing DNA fragments was cut-off the gel and gel purified using the "Zymoclean™ Gel DNA Recovery Kit" according to the provided protocol.

Tagging of the PAM-Containing gtCAs9 Cleaved DNA Fragments for Sequencing

The Cas9-induced DNA breaks are usually introduced between the $3^{rd}$ and the $4^{th}$ nucleotide of a protospacer, proximally to the PAM sequence. As a result, it is not possible to design a pair of primers that can PCR amplify the PAM-containing part of the cleaved DNA fragments, in order to further on sequence and determine the PAM sequence. For this purpose a 5-step process was employed:

Step 1: A-Tailing with Taq Polymerase

A-Tailing is a process to add a non-templated adenine to the 3' end of a blunt, double-stranded DNA molecule using Taq polymerase Reaction components:
gtCas9-cleaved and PAM-containing DNA fragments—200 ng
10× ThermoPol® Buffer (NEB)—5 µl
1 mMdATP-10 µl
Taq DNA Polymerase (NEB)—0.2 µl
H2O—up to 50 µl final reaction volume
Incubation time—20 min
Incubation temperature—72° C.

Step 2: Construction of the Sequencing Adaptors

Two complementary short ssDNA oligonucleotides were phosphorylated and annealed to form the sequencing adaptor for the PAM-proximal site of the DNA fragments from step 1. One of the oligonucleotides had an additional thymine at its 3' end, in order to facilitate the ligation of the adaptor to the A-tailed fragments.

Adaptor Oligonucleotides phosphorylation (Separate phosphorylation reactions for each oligo)
100 µM oligonucleotide stock—2 µL
10× T4 DNA ligase buffer (NEB)—2 µL
Sterile MQ water—15 µL
T4 Polynucleotide Kinase (NEB)—1 µL
Incubation time—60 min
Incubation temperature—37° C.
T4 PNK inactivation—65° C. for 20 min Annealing of the phosphorylated oligonucleotides
Oligonucleotide 1-5 µL from the corresponding phosphorylation mixture
Oligonucleotide 1-5 µL from the corresponding phosphorylation mixture
Sterile MQ water—90 µL
Incubate the phosphorylated oligos at 95° C. for 3 minutes. Cool the reaction slowly at room temperature for—30 min to 1 hr Step 3: Ligation of the gtCas9-Cleaved, A-Tailed Fragments with the Sequencing Adaptors The products of step 1 and 2 were ligated according to the following protocol:
10× T4 DNA Ligase Buffer—2 µl
Product step 1-50 ng
Product step 2-4 ng
T4 DNA Ligase—1 µl
Terile MQ water—to 20 µl
Incubation time—10 min
Incubation temperature—20-25° C.
Heat inactivation at 65° C. for 10 min Step 4: PCR Amplification of a 150-Nucleotides Long PAM-Containing Fragment 5 µl from the ligation mixture of step 4 were used as template for PCR amplification using Q5 DNA polymerase (NEB). The oligonucleotide with the thymine extension from step 2 was employed as the forward primer and the reverse primer was designed to anneal 150 nucleotides downstream of the PAM sequence.

The same sequence was amplified using non-gtCas9 treated PAM-library DNA as template. Both PCR products were gel purified and sent for Illumina HiSeq 2500 paired-end sequencing (Baseclear).

Analysis of the Sequencing Results and Determination of the Candidate PAM Sequences After analysing the sequencing results the following frequency matrices were constructed. The matrices depict the relative abundance of each nucleotide at every PAM position of the gtCas9 digested and non-digested libraries:

| Non-digested | pos1 | pos2 | pos3 | pos4 | pos5 | pos6 | pos7 |
|---|---|---|---|---|---|---|---|
| A | 19.22 | 20.83 | 19.12 | 24.43 | 24.59 | 21.75 | 18.22 |
| C | 34.75 | 30 | 31.9 | 30.54 | 25.96 | 27.9 | 27.17 |
| T | 19.16 | 22.19 | 25.34 | 21.28 | 26.09 | 26 | 21.56 |
| G | 26.87 | 26.98 | 23.64 | 23.75 | 23.36 | 24.35 | 33.05 |
| Digested | pos1 | pos2 | pos3 | pos4 | pos5 | pos6 | pos7 |
| A | 10.63 | 18.65 | 14.6 | 14.49 | 3.36 | 8.66 | 27.54 |
| C | 66.22 | 49.59 | 56.82 | 60.35 | 92.4 | 62.26 | 34.94 |
| T | 8.09 | 11.21 | 19.12 | 12.15 | 2.35 | 14.66 | 5.58 |
| G | 15.05 | 20.54 | 9.45 | 13.01 | 1.89 | 14.43 | 31.94 |

These results indicate a clear preference for targets with cytosine at the $5^{th}$ PAM position and preference for targets with cytosines at the first 4 PAM positions.

Example 7: In Silico PAM Prediction for gtCas9

Figure 8:
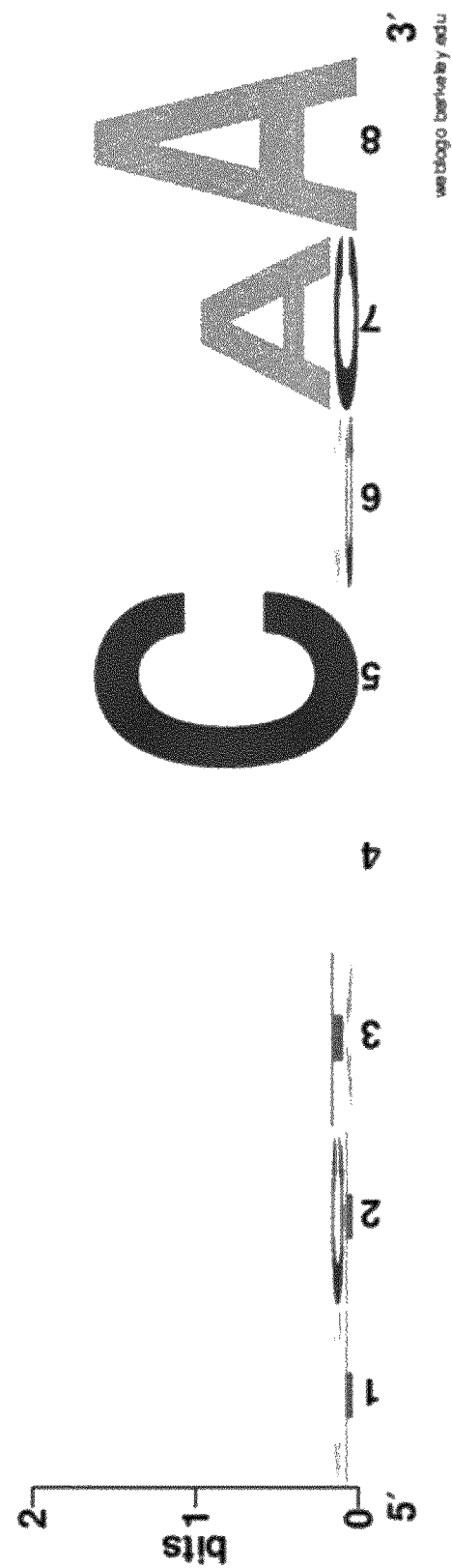
FIG. 8 shows a weblogo combining the results of the alignments illustrated in FIG. 7. The weblogo was generated using weblogo.berkeley.edu.

In silico predictions of PAMs are possible if enough protospacer sequences are available in genome databases. The in silico prediction of gtCas9 PAM started with identification of hits of spacers from the CRISPR array in the genome of G. thermodenitrificans T12 strain by comparison to sequences in genome databases such as GenBank. The "CRISPR finder" (crispr.u-psud.fr/Server/) tool was used to identify candidate CRISPR loci in T12. The identified CRISPR loci output was then loaded into "CRISPR target" (bioanalysis.otago.ac.nz/CRISPRTarget/crispr_analysis.html) tool, which searches selected databases and provides an output with matching protospacers. These protospacer sequences were then screened for unique hits and for complementarity to spacers—for example, mismatches in the seed sequence were considered to be likely false positive hits and were excluded from further analysis. Hits with identity to prophage sequences and (integrated) plasmids demonstrated that the obtained hits were true positives. Overall, this process yielded 6 single hits (FIG. 7). Subsequently, the flanking regions (3' for Type II gtCas nuclease) of the remaining, unique protospacer hits were aligned and compared for consensus sequences using a WebLogo (weblogo.berkeley.edu/loqo.cqi) (Crooks G E, Hon G, Chandonia J M, Brenner S E WebLogo: A sequence logo generator, *Genome Research,* 14:1188-1190, (2004)) tool (FIG. 8).

The in silico results were comparable to the in vitro PAM identification experimental results (see Example 6) in which there was a bias for the identity of the $5^{th}$ residue of the PAM sequence to be a cytosine.

Example 8: Determination of 8 Nucleotide Long PAM Sequences for gtCas9

The in silico data from Example 8 suggested that gtCas9 had some preference for adenosine at the $8^{th}$ position, therefore further PAM determination experiments were carried out where the $8^{th}$ position of the PAM sequence was also tested. This is consistent with the characterisation of mesophilic *Brevibacillus laterosporus* SSP360D4 (Karvelis et al., 2015) Cas9 PAM sequence which was found to extend between the $5^{th}$ and the $8^{th}$ positions at the 3' end of a protospacer.

Specific 8 nucleotide-long sequence variants of the PAMs were trialed with gtCas9:

1) CNCCCCAC,     [SEQ ID NO: 17]

2) CCCCCCAG,     [SEQ ID NO: 18]

3) CCCCCCAA,     [SEQ ID NO: 11]

4) CCCCCCAT,     [SEQ ID NO: 19]

5) CCCCCCAC,     [SEQ ID NO: 20]

6) NNNNTNNC (negative control PAM)

Figure 9:
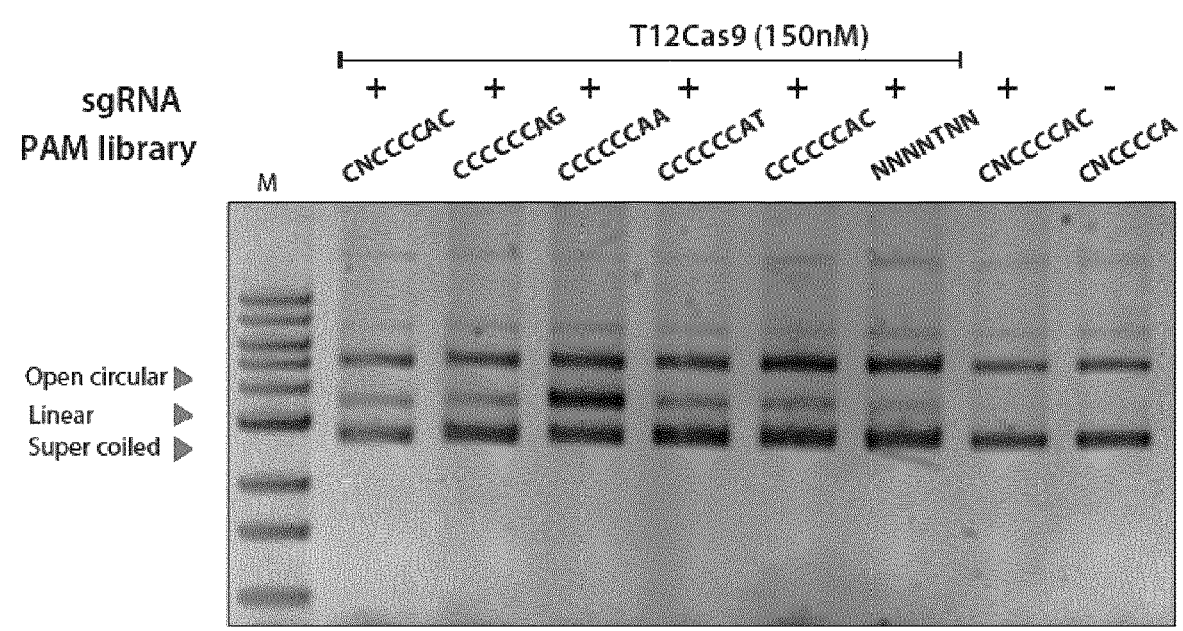
FIG. 9 shows the results of an in vitro cleavage assay at 60° C. targeting plasmids with purified gtCas9. The plasmids included specific 8 nucleotide-long sequence variants of the PAM sequences.

After performing an in vitro cleavage assay at 60° C. targeting these (non-linearized) plasmids with purified gtCas9 and the same sgRNA as before (see Example 6) an increased gtCas9 cleavage activity when the CCCCCCAA [SEQ ID NO: 11] sequence was employed as PAM was observed (FIG. 9). However, cleavage activity was clearly detectable for all the tested PAM sequences, even for the negative control PAM sequence a faint cleavage band was observed. Without wishing to be bound to a particular theory, it is possible that use of high gtCas9 concentration contributed to the cleavage observed with the negative control. It has been generally observed that high Cas9 concentrations in in vitro assays lead to Cas9-induced DNA cleavage without stringent PAM requirement.

Figure 10:
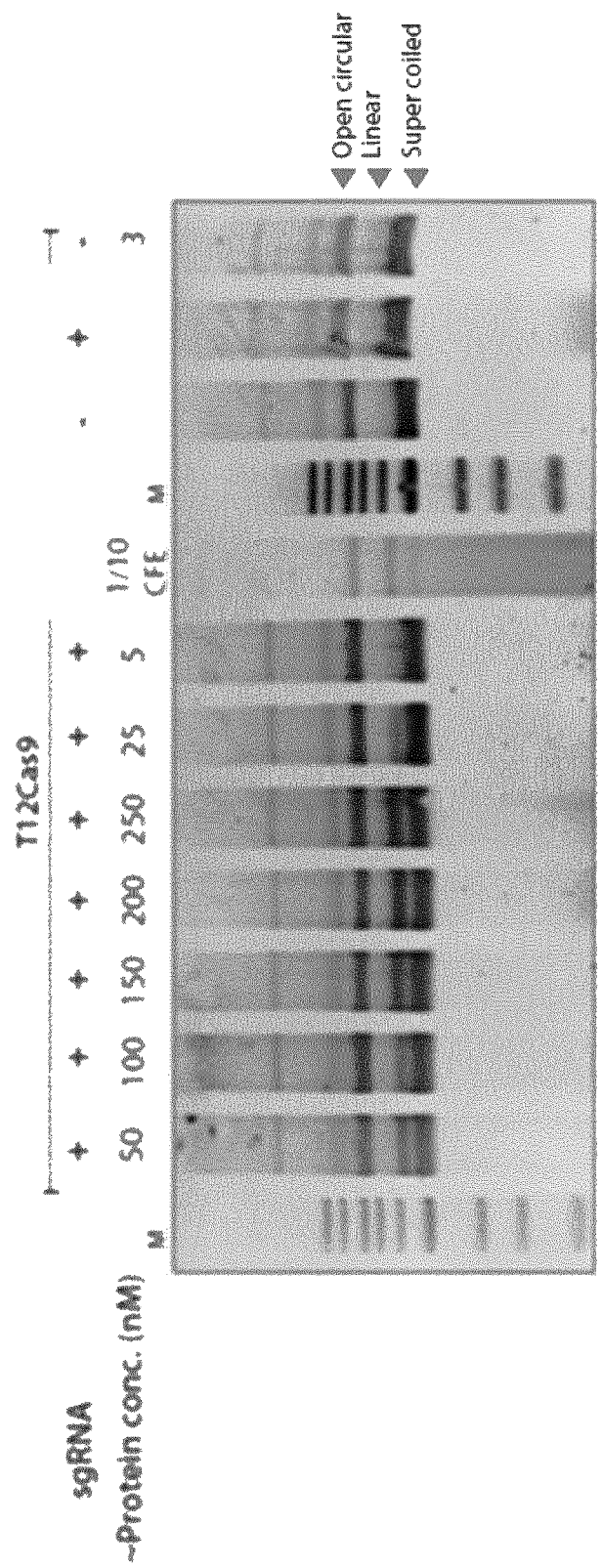
FIG. 10 shows the results of in vitro assays to investigate the effect of gtCas9 concentration, using a targeted plasmid with the CCCCCCAA [SEQ ID NO: 11] PAM sequence.

Cas9 concentration in general is known to influence the efficiency of the Cas9 induced DNA cleavage (higher Cas9 concentration results in higher Cas9 activity). This was also observed when performing in vitro assays using the targeted plasmid with the CCCCCCAA [SEQ ID NO: 11] PAM sequence and different gtCas9 concentrations (FIG. 10)

Figure 11:
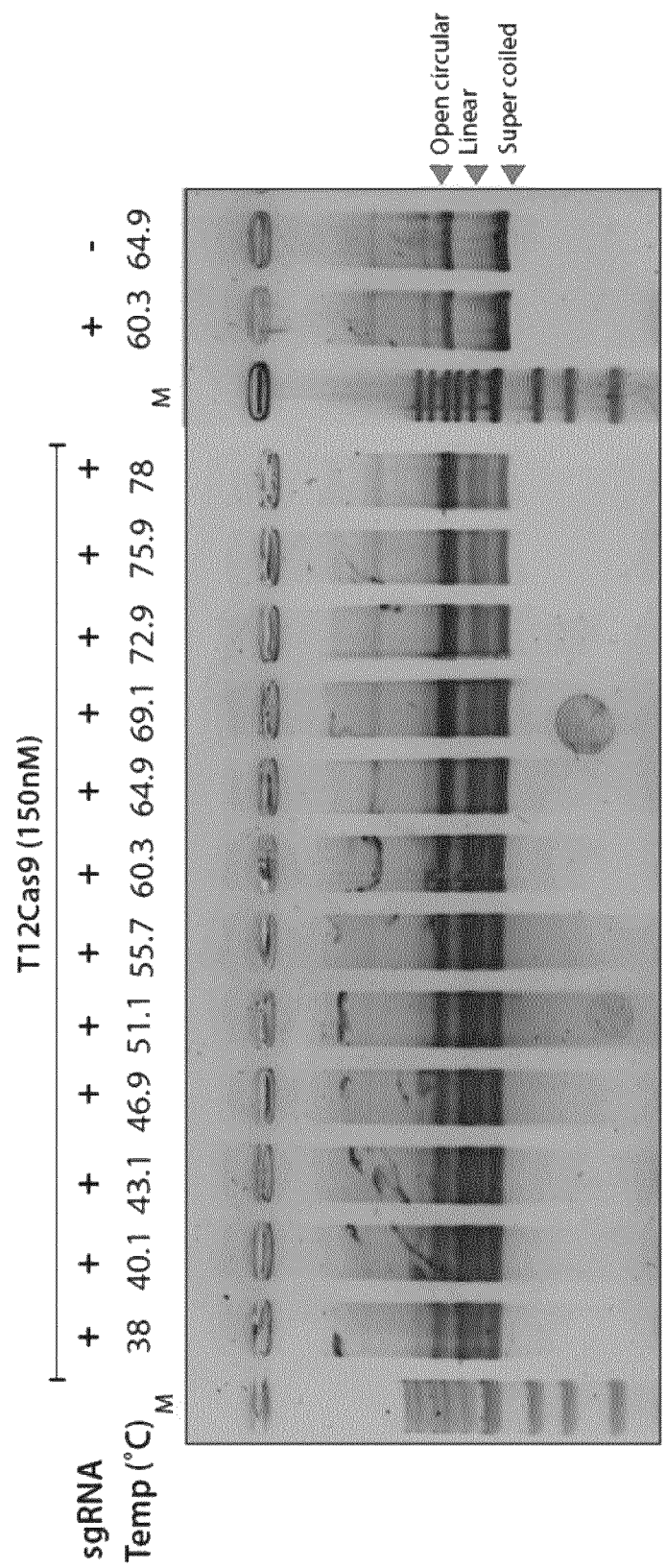
FIG. 11 shows the results of in vitro assays using a targeted plasmid with the CCCCCCAA [SEQ ID NO: 11] PAM sequence over a range of temperatures.

The targeted plasmid with the CCCCCCAA [SEQ ID NO: 11] PAM sequence for in vitro assays as described above was conducted over a wide temperature range between 38 and 78° C. (FIG. 11). Surprisingly, gtCas9 was active at all the temperatures showing the highest activity between 40.1 and 64.9° C.

Thus the optimal temperature range of Cas9 from *Geobacillus* species is much higher than that of Cas9 proteins which have been characterised to date. Similarly the upper extent of the range in which it retains nuclease activity is much higher than that of known Cas9 proteins. A higher optimal temperature and functional range provides a significant advantage in genetic engineering at high temperatures and therefore in editing the genomes of thermophilic organisms, which have utility in a range of industrial, agricultural and pharmaceutical processes conducted at elevated temperatures.

Example 9: In Vivo Genome Editing of *Bacillus smithii* ET138 with gtCas9 and 8 Nucleotide Length PAM Sequences To confirm that the 8 nucleotide PAMs were also recognised by gtCas9 in vivo, an experiment was designed to delete the pyrF gene in the genome of *Bacillus smithii* ET138 at 55° C.

This method relies upon providing a homologous recombination template construct in which regions complimentary to the upstream and downstream of the target (pyrF) gene are provided to *B. smithii* ET 138 cells. Introduction of the template allows for the process of homologous recombination to be used to introduce the homologous recombination template (with no pyrF gene) into the genome such that it also replaces the WT pyrF gene in the genome of a cell.

Inclusion of a gtCas9 and a sgRNA in the homologous recombination construct can be used to introduce double stranded DNA breaks (DSDBs) into bacterial genomes that contain WT pyrF. DSDBs in a bacterial genome typically results in cell death. Therefore, a sgRNA that recognises a sequence in the WT pyrF could result in DSDB and death of cells containing the WT pyrF only. Introduction of DSDB is also dependent on a suitable PAM sequence being located downstream at the 3' end of the protospacer that is recognised by gtCas9.

The pNW33n plasmid was used as a backbone to clone:
i) the $cas9_{gt}$ gene under the control of an in-house developed glucose repressible promoter; and
ii) the 1 kb upstream and 1 kb downstream regions of the pyrF gene in the genome of *B. smithii* ET138 as a template for homologous recombination that would result in deletion of the pyrF gene from the genome of *B. smithii* ET138; and
iii) single guide RNA (sgRNA) expressing module under the transcriptional control of a constitutive promoter.

Three separate constructs were generated in which the sequence of the single guide RNAs differed at the first 20 nucleotides, which correspond to the sequence that guides the gtCas9 to its specific DNA target in the genome (also known as the spacer). The three different spacer sequences were designed to target three different candidate protospacers all in the pyrF gene of *B. smithii* ET138. The constructs are herein referred to as constructs 1, 2 and 3 respectively.

The three different targeted protospacers had at their 3'-end the following candidate PAM sequences:
1. TCCATTCC (negative control according to the results of the in vitro assays; 3'-end of the protospacer targeted by the sgRNA encoded on construct number 3)
2. ATCCCCAA (3'-end of the protospacer targeted by the sgRNA encoded on construct number 1; [SEQ ID NO: 21])
3. ACGGCCAA (3'-end of the protospacer targeted by the sgRNA encoded on construct number 2, [SEQ ID NO: 22])

After transforming *B. smithii* ET 138 cells with one of the three constructs and plating on selection plates, the following results were obtained:
1. When the cells were transformed with the construct targeting the protospacer that had the negative control TCCATTCC PAM sequence at the 3' end (construct number 3) the transformation efficiency was not affected (FIG. 12 A). The number of colonies was in the same range as the number of colonies after transformation with the pNW33n positive control construct (FIG. 12 B). Of the 15 colonies that were subjected to colony PCR to screen for colonies in which the pyrF gene was deleted, none showed the deletion genotype −2.1 kb expected band size-, all were wild-type −2.9 kb expected band size—(FIG. 13). This indicates that the tested PAM was indeed not recognised by the gtCas9 in vivo.
2. When the cells were transformed with construct number 1 only a few colonies were obtained (FIG. 12 C) when compared to the positive control (cells transformed with pNW33n). 20 colonies were subjected to colony PCR to screen for colonies in which the pyrF gene was deleted. The majority (19) of the colonies contained both the wild type and pyrF deletion genotype whilst one colonies had a pyrF deletion genotype (FIG. 14). This result indicated that the PAM sequence ATCCCCAA [SEQ ID NO: 21] is recognised in vivo by gtCas9 because no WT only genotypes were observed. The reduced transformation efficiency is also indicative that a proportion of the cell population has been reduced, which could be attributable to cell death caused of WT only genotype cells by DSDB due to successful targeting by gtCas9.
3. When the cells were transformed with construct number 2 no colonies were obtained (FIG. 12 D). The lack of colonies is indicative that all of the cell population had been successfully targeted by the gtCas9, which led to cell death caused by DSDB. This suggests that ACGGCCAA [SEQ ID NO: 22] PAM sequence is recognised by gtCas9.

These results indicate that gtCas9 is active at 55° C. in vivo with the above mentioned PAM sequences, a result that comes in agreement with the in vitro PAM determination results. Moreover it can be used as a genome editing tool at the same temperature in combination with a plasmid borne homologous recombination template.

The following section of the description consists of numbered paragraphs simply providing statements of the invention already described herein. The numbered paragraphs in this section are not claims. The claims are set forth below in the later section headed "claims".

1. An isolated clustered regularly interspaced short palindromic repeat (CRISPR)-associated (Cas) protein or polypeptide comprising;

a. the amino acid motif EKDGKYYC [SEQ ID NO: 2]; and/or b. the amino acid motif $X_1X_2CTX_3X_4$[SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and/or c. the amino acid motif $X_5LKX_6IE$ [SEQ ID NO: 4] wherein $X_5$ is independently selected from Methionine or Phenylalanine and $X_6$ is independently selected from Histidine or Asparagine; and/or d. the amino acid motif $X_7VYSX_8K$ [SEQ ID NO: 5] wherein $X_7$ is Glutamate or Isoleucine and $X_8$ is one of Tryptophan, Serine or Lysine; and/or e. the amino acid motif $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine;

wherein the Cas protein is capable of nucleic acid cleavage between 50° C. and 100° C. when associated with at least one targeting RNA molecule, and a polynucleotide comprising a target nucleic acid sequence recognised by the targeting RNA molecule.

2. An isolated Cas protein or polypeptide fragment having an amino acid sequence of SEQ ID NO: 1 or a sequence of at least 77% identity therewith, wherein the Cas protein is capable of binding, cleaving, modifying or marking a polynucleotide comprising a target nucleic acid sequence at a temperature between 50° C. and 100° C. when associated with at least one RNA molecule which recognizes the target sequence.

3. A Cas protein or polypeptide fragment as in numbered paragraph 1 or 2, wherein the Cas protein or fragment is capable of nucleic acid binding, cleavage, marking or modification at a temperature between 50° C. and 75° C., preferably at a temperature above 60° C.; more preferably at a temperature between 60° C. and 80° C.; more preferably at a temperature between 60° C. and 65° C.

4. A Cas protein or polypeptide fragment as in any of numbered paragraphs 1 to 3, wherein the nucleic acid binding, cleavage, marking or modification is DNA cleavage.

5. A Cas protein or polypeptide fragment as in any preceding numbered paragraph, wherein the amino acid sequence comprises an amino acid sequence of SEQ ID NO: 1 or a sequence of at least 77% identity therewith.

6. A Cas protein or polypeptide fragment as in any preceding numbered paragraph, wherein the Cas protein is obtainable from a bacterium, archaeon or virus.

7. A Cas protein or polypeptide fragment as in any preceding numbered paragraph, wherein the Cas protein is obtainable from *Geobacillus* sp., preferably from *Geobacillus thermodenitrificans.*

8. A ribonucleoprotein complex comprising a Cas protein as in any preceding numbered paragraph, and comprising at least one targeting RNA molecule which recognises a sequence in a target polynucleotide.

9. A ribonucleoprotein complex as in numbered paragraph 8, wherein the targeting RNA molecule comprises a crRNA and optionally a tracrRNA.

10. A ribonucleoprotein complex as in any of numbered paragraphs 7 to 9, wherein the length of the at least one RNA molecule is in the range 35-135 nucleotide residues.

11. A ribonucleoprotein complex as in numbered paragraph 8 or 9, wherein the target sequence is 31 or 32 nucleotide residues in length.

12. A Cas protein or polypeptide as in any of numbered paragraphs 1 to 7 or a ribonucleoprotein complex as in any of 8 to 11, wherein the protein or polypeptide is provided as part of a protein complex comprising at least one further functional or non-functional protein.

13. A Cas protein, polypeptide, or ribonucleoprotein complex as in numbered paragraph 12, wherein the Cas protein or polypeptide, and/or the at least one further protein further comprise at least one functional moiety.

14. A Cas protein or polypeptide, or ribonucleoprotein complex as in numbered paragraph 13, wherein the at least one functional moiety is fused or linked to the N-terminus and/or the C-terminus of the Cas protein, polypeptide or ribonucleoprotein complex; preferably the N-terminus.

15. A Cas protein or polypeptide, or a ribonucleoprotein complex as in numbered paragraph 13 or 14, wherein the at least one functional moiety is a protein; optionally selected from a helicase, a nuclease, a helicase-nuclease, a DNA methylase, a histone methylase, an acetylase, a phosphatase, a kinase, a transcription (co-)activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag.

16. A Cas protein or polypeptide, or a ribonucleoprotein complex as in numbered paragraph 15, wherein the native activity of the Cas9 nuclease activity is inactivated and the Cas protein is linked to at least one functional moiety.

17. A Cas protein or polypeptide, or a ribonucleoprotein complex as in numbered paragraph 15 or 16, wherein the at least one functional moiety is a nuclease domain; preferably a FokI nuclease domain.

18. A Cas protein or polypeptide, or a ribonucleoprotein complex as in any of numbered paragraphs 15 to 17, wherein the at least one functional moiety is a marker protein, for example GFP.

19. An isolated nucleic acid molecule encoding a Cas protein or polypeptide, comprising;

a. the amino acid motif EKDGKYYC [SEQ ID NO: 2]; and/or b. the amino acid motif $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and/or c. the amino acid motif $X_5LKX_6IE$ [SEQ ID NO: 4] wherein $X_5$ is independently selected from Methionine or Phenylalanine and $X_6$ is independently selected from Histidine or Asparagine; and/or d. the amino acid motif $X_7VYSX_8K$ [SEQ ID NO: 5] wherein $X_7$ is Glutamate or Isoleucine and $X_8$ is one of Tryptophan, Serine or Lysine; and/or e. the amino acid motif $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine;

wherein the Cas protein or polypeptide is capable of DNA binding, cleavage, marking or modification between 50° C. and 100° C. when associated with at least one targeting RNA molecule, and a polynucleotide comprising a target nucleic acid sequence recognised by the targeting RNA molecule.

20. An isolated nucleic acid molecule encoding a clustered regularly interspaced short palindromic repeat (CRISPR)-associated (Cas) protein having an amino acid sequence of SEQ ID NO: 1 or a sequence of at least 77% identity therewith; or a polypeptide fragment thereof.

21. An isolated nucleic acid molecule as in numbered paragraph 19 or 20, further comprising at least one nucleic acid sequence encoding an amino acid sequence which upon translation is fused with the Cas protein or polypeptide.

22. An isolated nucleic acid molecule as in numbered paragraph 21, wherein the at least one nucleic acid sequence fused to the nucleic acid molecule encoding the Cas protein or polypeptide, encodes a protein selected from a protein selected from a helicase, a nuclease, a helicase-nuclease, a DNA methylase, a histone methylase, an acetylase, a phosphatase, a kinase, a transcription (co-)activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag.

23. An expression vector comprising a nucleic acid molecule as in any of numbered paragraphs 19 to 22.

24. An expression vector as in numbered paragraph 23, further comprising a nucleotide sequence encoding at least one targeting RNA molecule.

25. A method of modifying a target nucleic acid comprising contacting the nucleic acid with:

a. a ribonucleoprotein complex of any of numbered paragraphs 6 to 11; or b. a protein or protein complex of any of numbered paragraphs 12 to 18 and at least one targeting RNA molecule as defined in any of numbered paragraphs 6 to 11.

26. A method of modifying a target nucleic acid in a cell, comprising transforming, transfecting or transducing the cell with an expression vector of numbered paragraph 24; or alternatively transforming, transfecting or transducing the cell with an expression vector of numbered paragraph 23 and a further expression vector comprising a nucleotide sequence encoding a targeting RNA molecule as defined in any of numbered paragraphs 6 to 11.

27. A method of modifying a target nucleic acid in a cell comprising transforming, transfecting or transducing the cell with an expression vector of numbered paragraph 23, and then delivering a targeting RNA molecule as defined in any of numbered paragraphs 6 to 11 to or into the cell.

28. A method of modifying a target nucleic acid as in any of numbered paragraphs 25 to 28, wherein the at least one functional moiety is a marker protein or reporter protein and the marker protein or reporter protein associates with the target nucleic acid; preferably wherein the marker is a fluorescent protein, for example a green fluorescent protein (GFP).

29. A method as in any of numbered paragraphs 25 to 28, wherein the target nucleic acid is DNA; preferably dsDNA.

30. A method as in any of numbered paragraphs 25 to 28, wherein the target nucleic acid is RNA.

31. A method of modifying a target nucleic acid as in numbered paragraph 29, wherein the nucleic acid is dsDNA, the at least one functional moiety is a nuclease or a helicase-nuclease, and the modification is a single-stranded or a double-stranded break at a desired locus.

32. A method of silencing gene expression at a desired locus according to any of the methods in any of numbered paragraphs 26, 27, 29 or 31.

33. A method of modifying or deleting and/or inserting a desired nucleotide sequence at a desired location according to any of the methods as in any of numbered paragraphs 26, 27, 29 or 31.

34. A method of modifying gene expression in a cell comprising modifying a target nucleic acid sequence as in a method of any of numbered paragraphs 25 to 29; wherein the nucleic acid is dsDNA and the functional moiety is selected from a DNA modifying enzyme (e.g. a methylase or acetylase), a transcription activator or a transcription repressor.

35. A method of modifying gene expression in a cell comprising modifying a target nucleic acid sequence as in a method of numbered paragraph 30, wherein the nucleic acid is an mRNA and the functional moiety is a ribonuclease; optionally selected from an endonuclease, a 3' exonuclease or a 5' exonuclease.

36. A method of modifying a target nucleic acid as in any of numbered paragraphs 25 to 35, wherein the method is carried out at a temperature between 50° C. and 100° C.

37. A method of modifying a target nucleic acid as in numbered paragraph 36, wherein the method is carried out at a temperature at or above 60° C., preferably between 60° C. and 80° C., more preferably between 60° C. and 65° C.

38. A method as in any of numbered paragraphs 25 to 37 wherein the cell is a prokaryotic cell.

39. A method as in any of numbered paragraphs 25 to 38 wherein the cell is a eukaryotic cell.

40. A host cell transformed by a method as in any of numbered paragraphs 22 to 36.

The invention claimed is:

1. A method of binding, cleaving, marking or modifying a double stranded target polynucleotide, wherein the double stranded target polynucleotide comprises a target nucleic acid strand comprising a target nucleic acid sequence, and a non-target nucleic acid strand comprising a protospacer nucleic acid sequence complementary to the target nucleic acid sequence, said method comprising:
   a) designing at least one targeting RNA molecule, wherein the targeting RNA molecule recognizes the target sequence in the target strand, and the non-target strand further comprises a protospacer adjacent motif (PAM) sequence directly adjacent the 3' end of the protospacer sequence, wherein the PAM sequence comprises 5'-NNNNCNN-3';
   b) forming a ribonucleoprotein complex comprising the targeting RNA molecule and a Cas protein, wherein the isolated Cas protein has the amino acid sequence of SEQ ID NO: 1 or a sequence of at least 89% identity therewith; and
   c) the ribonucleoprotein complex binding, cleaving, marking or modifying the target polynucleotide.

2. The method as claimed in claim 1, wherein the binding, cleaving, marking or modifying occurs at a temperature between 20° C. and 100° C.

3. The method as claimed in claim 1, wherein the double stranded target polynucleotide comprising the target nucleic acid sequence is cleaved by the Cas protein.

4. The method as claimed in claim 1, wherein the target polynucleotide comprising the target nucleic acid sequence is double stranded DNA, the Cas protein lacks the ability to cut the double stranded DNA and said method results in gene silencing of the target polynucleotide.

5. The method as claimed in claim 1, wherein the PAM sequence comprises at least one sequence selected from the group consisting of 5'-NNNNCNNA-3', 5'-CNNNCNN-3', 5'-NNNCCNN-3', 5'-NNCNCNN-3', 5'-NNNNCCN-3', 5'-NCNNCNN-3', 5'-CCCCCCNA-3' (SEQ ID NO: 10) and 5'-CCCCCCAA-3' (SEQ ID NO: 11).

6. The method as claimed in claim 1, wherein the Cas protein is obtainable from a species selected from the group consisting of a bacterium, an archaeon, a virus, a thermophilic bacterium; a *Geobacillus* sp. and *Geobacillus thermodenitrificans*.

7. The method as claimed in claim 1, wherein the targeting RNA molecule comprises a crRNA and a tracrRNA.

8. The method as claimed in claim 1, wherein the length of the at least one targeting RNA molecule is in the range 35-200 nucleotide residues.

9. The method as claimed in claim 1, wherein the target nucleic acid sequence is from 15 to 32 nucleotide residues in length.

10. The method as claimed in claim 1, wherein the Cas protein further comprises at least one functional moiety selected from the group consisting of a helicase, a nuclease, a helicase-nuclease, a DNA methylase, a histone methylase, an acetylase, a phosphatase, a kinase, a transcription activator, a transcription coactivator, a transcription repressor, a DNA binding protein, a DNA structuring protein, a marker protein, a reporter protein, a fluorescent protein, a ligand binding protein, a signal peptide, a subcellular localisation sequence, an antibody epitope and an affinity purification tag.

11. The method as claimed in claim 10, wherein the native activity of the Cas9 nuclease is inactivated and the Cas protein is linked to the at least one functional moiety.

12. The method as claimed in claim 10, wherein the double stranded target polynucleotide is dsDNA, the at least one functional moiety is selected from the group consisting of a nuclease and a helicase-nuclease, and the modification is selected from the group consisting of a single-stranded and a double-stranded break at a desired locus.

13. The method as claimed in claim 10, wherein the double stranded target polynucleotide is dsDNA and the functional moiety is selected from the group consisting of a DNA modifying enzyme, a methylase, an acetylase, a transcription activator and a transcription repressor and the binding, cleaving, marking or modifying results in modification of gene expression.

14. The method as claimed in claim 1, wherein said binding, cleaving, marking or modifying occurs in vivo.

15. The method as claimed in claim 1, wherein the binding, cleaving, marking or modifying results in at least one selected from the group consisting of modifying a desired nucleotide sequence at a desired location, deleting a desired nucleotide sequence at a desired location, inserting a desired nucleotide sequence at a desired location, and silencing gene expression at a desired locus.

16. A transformed cell, having a double stranded target polynucleotide comprising a target nucleic acid sequence, wherein the double stranded target polynucleotide comprises a target nucleic acid strand, comprising said target nucleic acid sequence, and a non-target nucleic acid strand, comprising a protospacer nucleic acid sequence complementary to the target nucleic acid sequence, said cell comprising:
   a clustered regularly interspaced short palindromic repeat (CRISPR)-associated (Cas) protein having the amino acid sequence of SEQ ID NO: 1 or a sequence of at least 89% identity therewith;
   at least one targeting RNA molecule which recognizes the target nucleic acid sequence in the target nucleic acid strand, wherein the non-target strand further comprises a protospacer adjacent motif (PAM) sequence directly adjacent the 3' end of the protospacer sequence, wherein the PAM sequence comprises 5'-NNNNCNN-3'; and
   an expression vector comprising a nucleic acid encoding at least one of said Cas protein and said targeting RNA molecule.

17. The transformed cell as claimed in claim 16, wherein the cell is a prokaryotic cell.

18. The transformed cell as claimed in claim 16, wherein the Cas protein is expressed from an expression vector.

19. A nucleoprotein complex comprising a Cas protein, at least one targeting RNA molecule which recognizes a target nucleic acid sequence in a double stranded target polynucleotide, and the target polynucleotide, wherein
   the Cas protein has the amino acid sequence of SEQ ID NO: 1 or a sequence of at least 89% identity therewith;
   the double stranded target polynucleotide comprises a target nucleic acid strand, comprising said target nucleic acid sequence, and a non-target nucleic acid strand, comprising a protospacer nucleic acid sequence complementary to the target nucleic acid sequence and a protospacer adjacent motif (PAM) sequence directly adjacent the 3' end of the protospacer sequence, wherein the PAM sequence comprises 5'-NNNNCNN-3'.

20. The nucleoprotein complex as claimed in claim 19, wherein the nucleoprotein complex is in a prokaryotic cell.

* * * * *

SEQUENCE LISTING

```
<160> NUMBER OF SEQ ID NOS: 42

<210> SEQ ID NO 1
<211> LENGTH: 1082
<212> TYPE: PRT
<213> ORGANISM: Geobacillus thermodenitrificans T12

<400> SEQUENCE: 1

Met Lys Tyr Lys Ile Gly Leu Asp Ile Gly Ile Thr Ser Ile Gly Trp
1               5                   10                  15

Ala Val Ile Asn Leu Asp Ile Pro Arg Ile Glu Asp Leu Gly Val Arg
                20                  25                  30

Ile Phe Asp Arg Ala Glu Asn Pro Lys Thr Gly Glu Ser Leu Ala Leu
            35                  40                  45

Pro Arg Arg Leu Ala Arg Ser Ala Arg Arg Leu Arg Arg Arg Lys
    50                  55                  60

His Arg Leu Glu Arg Ile Arg Arg Leu Phe Val Arg Glu Gly Ile Leu
65                  70                  75                  80

Thr Lys Glu Glu Leu Asn Lys Leu Phe Glu Lys Lys His Glu Ile Asp
                85                  90                  95

Val Trp Gln Leu Arg Val Glu Ala Leu Asp Arg Lys Leu Asn Asn Asp
            100                 105                 110

Glu Leu Ala Arg Ile Leu Leu His Leu Ala Lys Arg Arg Gly Phe Arg
        115                 120                 125

Ser Asn Arg Lys Ser Glu Arg Thr Asn Lys Glu Asn Ser Thr Met Leu
    130                 135                 140

Lys His Ile Glu Glu Asn Gln Ser Ile Leu Ser Ser Tyr Arg Thr Val
145                 150                 155                 160

Ala Glu Met Val Val Lys Asp Pro Lys Phe Ser Leu His Lys Arg Asn
                165                 170                 175

Lys Glu Asp Asn Tyr Thr Asn Thr Val Ala Arg Asp Asp Leu Glu Arg
            180                 185                 190

Glu Ile Lys Leu Ile Phe Ala Lys Gln Arg Glu Tyr Gly Asn Ile Val
        195                 200                 205

Cys Thr Glu Ala Phe Glu His Glu Tyr Ile Ser Ile Trp Ala Ser Gln
    210                 215                 220

Arg Pro Phe Ala Ser Lys Asp Asp Ile Glu Lys Lys Val Gly Phe Cys
225                 230                 235                 240

Thr Phe Glu Pro Lys Glu Lys Arg Ala Pro Lys Ala Thr Tyr Thr Phe
                245                 250                 255
```

-continued

Gln Ser Phe Thr Val Trp Glu His Ile Asn Lys Leu Arg Leu Val Ser
            260                 265                 270

Pro Gly Gly Ile Arg Ala Leu Thr Asp Asp Glu Arg Arg Leu Ile Tyr
        275                 280                 285

Lys Gln Ala Phe His Lys Asn Lys Ile Thr Phe His Asp Val Arg Thr
    290                 295                 300

Leu Leu Asn Leu Pro Asp Asp Thr Arg Phe Lys Gly Leu Leu Tyr Asp
305                 310                 315                 320

Arg Asn Thr Thr Leu Lys Glu Asn Glu Lys Val Arg Phe Leu Glu Leu
                325                 330                 335

Gly Ala Tyr His Lys Ile Arg Lys Ala Ile Asp Ser Val Tyr Gly Lys
            340                 345                 350

Gly Ala Ala Lys Ser Phe Arg Pro Ile Asp Phe Asp Thr Phe Gly Tyr
        355                 360                 365

Ala Leu Thr Met Phe Lys Asp Asp Thr Asp Ile Arg Ser Tyr Leu Arg
    370                 375                 380

Asn Glu Tyr Glu Gln Asn Gly Lys Arg Met Glu Asn Leu Ala Asp Lys
385                 390                 395                 400

Val Tyr Asp Glu Glu Leu Ile Glu Glu Leu Leu Asn Leu Ser Phe Ser
                405                 410                 415

Lys Phe Gly His Leu Ser Leu Lys Ala Leu Arg Asn Ile Leu Pro Tyr
            420                 425                 430

Met Glu Gln Gly Glu Val Tyr Ser Thr Ala Cys Glu Arg Ala Gly Tyr
        435                 440                 445

Thr Phe Thr Gly Pro Lys Lys Lys Gln Lys Thr Val Leu Leu Pro Asn
    450                 455                 460

Ile Pro Pro Ile Ala Asn Pro Val Val Met Arg Ala Leu Thr Gln Ala
465                 470                 475                 480

Arg Lys Val Val Asn Ala Ile Ile Lys Lys Tyr Gly Ser Pro Val Ser
                485                 490                 495

Ile His Ile Glu Leu Ala Arg Glu Leu Ser Gln Ser Phe Asp Glu Arg
            500                 505                 510

Arg Lys Met Gln Lys Glu Gln Glu Gly Asn Arg Lys Lys Asn Glu Thr
        515                 520                 525

Ala Ile Arg Gln Leu Val Glu Tyr Gly Leu Thr Leu Asn Pro Thr Gly
    530                 535                 540

Leu Asp Ile Val Lys Phe Lys Leu Trp Ser Glu Gln Asn Gly Lys Cys
545                 550                 555                 560

Ala Tyr Ser Leu Gln Pro Ile Glu Ile Glu Arg Leu Leu Glu Pro Gly
                565                 570                 575

Tyr Thr Glu Val Asp His Val Ile Pro Tyr Ser Arg Ser Leu Asp Asp
            580                 585                 590

Ser Tyr Thr Asn Lys Val Leu Val Leu Thr Lys Glu Asn Arg Glu Lys
        595                 600                 605

Gly Asn Arg Thr Pro Ala Glu Tyr Leu Gly Leu Gly Ser Glu Arg Trp
    610                 615                 620

Gln Gln Phe Glu Thr Phe Val Leu Thr Asn Lys Gln Phe Ser Lys Lys
625                 630                 635                 640

Lys Arg Asp Arg Leu Leu Arg Leu His Tyr Asp Glu Asn Glu Glu Asn
                645                 650                 655

Glu Phe Lys Asn Arg Asn Leu Asn Asp Thr Arg Tyr Ile Ser Arg Phe
            660                 665                 670

Leu Ala Asn Phe Ile Arg Glu His Leu Lys Phe Ala Asp Ser Asp Asp 675                 680                 685
Lys Gln Lys Val Tyr Thr Val Asn Gly Arg Ile Thr Ala His Leu Arg
    690                 695                 700

Ser Arg Trp Asn Phe Asn Lys Asn Arg Glu Glu Ser Asn Leu His His
705                 710                 715                 720

Ala Val Asp Ala Ala Ile Val Ala Cys Thr Thr Pro Ser Asp Ile Ala
                725                 730                 735

Arg Val Thr Ala Phe Tyr Gln Arg Arg Glu Gln Asn Lys Glu Leu Ser
            740                 745                 750

Lys Lys Thr Asp Pro Gln Phe Pro Gln Pro Trp Pro His Phe Ala Asp
        755                 760                 765

Glu Leu Gln Ala Arg Leu Ser Lys Asn Pro Lys Glu Ser Ile Lys Ala
    770                 775                 780

Leu Asn Leu Gly Asn Tyr Asp Asn Glu Lys Leu Glu Ser Leu Gln Pro
785                 790                 795                 800

Val Phe Val Ser Arg Met Pro Lys Arg Ser Ile Thr Gly Ala Ala His
                805                 810                 815

Gln Glu Thr Leu Arg Arg Tyr Ile Gly Ile Asp Glu Arg Ser Gly Lys
            820                 825                 830

Ile Gln Thr Val Val Lys Lys Leu Ser Glu Ile Gln Leu Asp Lys
        835                 840                 845

Thr Gly His Phe Pro Met Tyr Gly Lys Glu Ser Asp Pro Arg Thr Tyr
    850                 855                 860

Glu Ala Ile Arg Gln Arg Leu Leu Glu His Asn Asn Asp Pro Lys Lys
865                 870                 875                 880

Ala Phe Gln Glu Pro Leu Tyr Lys Pro Lys Lys Asn Gly Glu Leu Gly
                885                 890                 895

Pro Ile Ile Arg Thr Ile Lys Ile Ile Asp Thr Thr Asn Gln Val Ile
            900                 905                 910

Pro Leu Asn Asp Gly Lys Thr Val Ala Tyr Asn Ser Asn Ile Val Arg
        915                 920                 925

Val Asp Val Phe Glu Lys Asp Gly Lys Tyr Tyr Cys Val Pro Ile Tyr
    930                 935                 940

Thr Ile Asp Met Met Lys Gly Ile Leu Pro Asn Lys Ala Ile Glu Pro
945                 950                 955                 960

Asn Lys Pro Tyr Ser Glu Trp Lys Glu Met Thr Glu Asp Tyr Thr Phe
                965                 970                 975

Arg Phe Ser Leu Tyr Pro Asn Asp Leu Ile Arg Ile Glu Phe Pro Arg
            980                 985                 990

Glu Lys Thr Ile Lys Thr Ala Val Gly Glu Glu Ile Lys Ile Lys Asp
        995                 1000                1005

Leu Phe Ala Tyr Tyr Gln Thr Ile Asp Ser Ser Asn Gly Gly Leu
        1010                1015                1020

Ser Leu Val Ser His Asp Asn Asn Phe Ser Leu Arg Ser Ile Gly
        1025                1030                1035

Ser Arg Thr Leu Lys Arg Phe Glu Lys Tyr Gln Val Asp Val Leu
        1040                1045                1050

Gly Asn Ile Tyr Lys Val Arg Gly Glu Lys Arg Val Gly Val Ala
        1055                1060                1065

Ser Ser Ser His Ser Lys Ala Gly Glu Thr Ile Arg Pro Leu
        1070                1075                1080

<210> SEQ ID NO 2

```
<211> LENGTH: 8
<212> TYPE: PRT
<213> ORGANISM: Geobacillus thermodenitrificans T12

<400> SEQUENCE: 2

Glu Lys Asp Gly Lys Tyr Tyr Cys
1               5

<210> SEQ ID NO 3
<211> LENGTH: 6
<212> TYPE: PRT
<213> ORGANISM: Artificial Sequence
<220> FEATURE:
<223> OTHER INFORMATION: amino acid motif of thermophilic Cas9
<220> FEATURE:
<221> NAME/KEY: misc_feature
<222> LOCATION: (1)..(1)
<223> OTHER INFORMATION: Xaa can be any of Ile, Met or Pro
<220> FEATURE:
<221> NAME/KEY: misc_feature
<222> LOCATION: (2)..(2)
<223> OTHER INFORMATION: Xaa can be any of Val, Ser, Asn or Ile
<220> FEATURE:
<221> NAME/KEY: misc_feature
<222> LOCATION: (5)..(5)
<223> OTHER INFORMATION: Xaa can be any of Glu or Lys
<220> FEATURE:
<221> NAME/KEY: misc_feature
<222> LOCATION: (6)..(6)
<223> OTHER INFORMATION: Xaa can be any of Ala, Glu or Arg

<400> SEQUENCE: 3

Xaa Xaa Cys Thr Xaa Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: amino acid motif of thermophilic Cas9
<220> FEATURE:
<221> NAME/KEY: misc_feature
<222> LOCATION: (1)..(1)
<223> OTHER INFORMATION: Xaa can be any of Met or Phe
<220> FEATURE:
<221> NAME/KEY: misc_feature
<222> LOCATION: (4)..(4)
<223> OTHER INFORMATION: Xaa can be any of His or Asn

<400> SEQUENCE: 4

Xaa Leu Lys Xaa Ile Glu
1               5

<210> SEQ ID NO 5
<211> LENGTH: 6
<212> TYPE: PRT
<213> ORGANISM: Artificial Sequence
<220> FEATURE:
<223> OTHER INFORMATION: amino acid motif of thermophilic Cas9
<220> FEATURE:
<221> NAME/KEY: misc_feature
<222> LOCATION: (1)..(1)
<223> OTHER INFORMATION: Xaa can be any of Glu or Ile
<220> FEATURE:
<221> NAME/KEY: misc_feature
<222> LOCATION: (5)..(5)
<223> OTHER INFORMATION: Xaa can be any of Trp, Ser or Lys

<400> SEQUENCE: 5

Xaa Val Tyr Ser Xaa Lys
1               5
```

<210> SEQ ID NO 6
<211> LENGTH: 12
<212> TYPE: PRT
<213> ORGANISM: Artificial sequence
<220> FEATURE:
<223> OTHER INFORMATION: amino acid motif of thermophilic Cas9
<220> FEATURE:
<221> NAME/KEY: misc_feature
<222> LOCATION: (1)..(1)
<223> OTHER INFORMATION: Xaa can be any of Ala or Glu
<220> FEATURE:
<221> NAME/KEY: misc_feature
<222> LOCATION: (4)..(4)
<223> OTHER INFORMATION: Xaa can be any of Gln or Lys
<220> FEATURE:
<221> NAME/KEY: misc_feature
<222> LOCATION: (5)..(5)
<223> OTHER INFORMATION: Xaa can be any of Arg or Ala
<220> FEATURE:
<221> NAME/KEY: misc_feature
<222> LOCATION: (9)..(9)
<223> OTHER INFORMATION: Xaa can be any of Asn or Ala
<220> FEATURE:
<221> NAME/KEY: misc_feature
<222> LOCATION: (12)..(12)
<223> OTHER INFORMATION: Xaa can be any of Lys or Ser

<400> SEQUENCE: 6

Xaa Phe Tyr Xaa Xaa Arg Glu Gln Xaa Lys Glu Xaa
1               5                   10

<210> SEQ ID NO 7
<211> LENGTH: 3249
<212> TYPE: DNA
<213> ORGANISM: Geobacillus thermodenitrificans T12

<400> SEQUENCE: 7

```
atgaagtata aaatcggtct tgatatcggc attacgtcta tcggttgggc tgtcattaat      60
ttggacattc ctcgcatcga agatttaggt gtccgcattt ttgacagagc ggaaaacccg     120
aaaaccgggg agtcactagc tcttccacgt cgcctcgccc gctccgcccg acgtcgtctg     180
cggcgtcgca acatcgact ggagcgcatt cgccgcctgt tcgtccgcga aggaatttta     240
acgaaggaag agctgaacaa gctgtttgaa aaaaagcacg aaatcgacgt ctggcagctt     300
cgtgttgaag cactggatcg aaaactaaat aacgatgaat tagcccgcat ccttcttcat     360
ctggctaaac ggcgtggatt tagatccaac cgcaagagtg agcgcaccaa caaagaaaac     420
agtacgatgc tcaaacatat tgaagaaaac caatccattc tttcaagtta ccgaacggtt     480
gcagaaatgg ttgtcaagga tccgaaattt ccctgcaca agcgtaataa agaggataat     540
tacaccaaca ctgttgcccg cgacgatctt gaacgggaaa tcaaactgat tttcgccaaa     600
cagcgcgaat atgggaacat cgtttgcaca gaagcatttg aacacgagta tatttccatt     660
tgggcatcgc aacgcccttt tgcttctaag gatgatatcg agaaaaaagt cggtttctgt     720
acgtttgagc ctaaagaaaa acgcgcgcca aaagcaacat acactttcca gtccttcacc     780
gtctgggaac atattaacaa acttcgtctt gtctccccgg gaggcatccg ggcactaacc     840
gatgatgaac gtcgtctat atacaagcaa gcatttcata aaaataaaat caccttccat     900
gatgttcgaa cattgcttaa cttgcctgac gacacccgtt ttaaaggtct tttatatgac     960
cgaaacacca cgctgaagga aaatgagaaa gttcgcttcc ttgaactcgg cgcctatcat    1020
aaaatacgga agcgatcga cagcgtctat ggcaaaggag cagcaaaatc atttcgtccg    1080
attgattttg atacatttgg ctacgcatta acgatgttta agacgacac cgacattgc     1140
```

-continued

```
agttacttgc gaaacgaata cgaacaaaat ggaaaacgaa tggaaaatct agcggataaa    1200
gtctatgatg aagaattgat tgaagaactt ttaaacttat cgttttctaa gtttggtcat    1260 ctatcccttta aagcgcttcg caacatcctt ccatatatgg aacaaggcga agtctactca    1320
accgcttgtg aacgagcagg atatacattt acagggccaa agaaaaaaca gaaacggta    1380 ttgctgccga acattccgcc gatcgccaat ccggtcgtca tgcgcgcact gacacaggca    1440
cgcaaagtgg tcaatgccat tatcaaaaag tacggctcac cggtctccat ccatatcgaa    1500
ctggcccggg aactatcaca atcctttgat gaacgacgta aaatgcagaa agaacaggaa    1560
ggaaaccgaa agaaaaacga aactgccatt cgccaacttg ttgaatatgg gctgacgctc    1620
aatccaactg gcttgacat tgtgaaattc aaactatgga gcgaacaaaa cggaaaatgt    1680
gcctattcac tccaaccgat cgaaatcgag cggttgctcg aaccaggcta tacagaagtc    1740
gaccatgtga ttccatacag ccgaagcttg gacgatagct ataccaataa agttcttgtg    1800
ttgacaaagg agaaccgtga aaaggaaac cgcaccccag ctgaatattt aggattaggc    1860
tcagaacgtt ggcaacagtt cgagacgttt gtcttgacaa ataagcagtt ttcgaaaaag    1920
aagcgggatc gactccttcg gcttcattac gatgaaaacg aagaaaatga gtttaaaaat    1980
cgtaatctaa atgatacccg ttatatctca cgcttcttgg ctaactttat tcgcgaacat    2040
ctcaaattcg ccgacagcga tgacaaacaa aaagtataca cggtcaacgg ccgtattacc    2100
gcccatttac gcagccgttg gaattttaac aaaaaccggg aagaatcgaa tttgcatcat    2160
gccgtcgatg ctgccatcgt cgcctgcaca acgccgagcg atatcgcccg agtcaccgcc    2220
ttctatcaac ggcgcgaaca aaacaaagaa ctgtccaaaa agacggatcc gcagtttccg    2280
cagccttggc cgcactttgc tgatgaactg caggcgcgtt tatcaaaaaa tccaaaggag    2340
agtataaaag ctctcaatct tggaaattat gataacgaga aactcgaatc gttgcagccg    2400 gttttttgtct cccgaatgcc gaagcggagc ataacaggag cggctcatca agaaacattg    2460
cggcgttata tcggcatcga cgaacggagc ggaaaaatac agacggtcgt caaaaagaaa    2520
ctatccgaga tccaactgga taaaacaggt catttcccaa tgtacgggaa agaaagcgat    2580
ccaaggacat atgaagccat cgccaacgg ttgcttgaac ataacaatga cccaaaaaag    2640
gcgtttcaag agcctctgta taaaccgaag aagaacggag aactaggtcc tatcatccga    2700
acaatcaaaa tcatcgatac gacaaatcaa gttattccgc tcaacgatgg caaaacagtc    2760
gcctacaaca gcaacatcgt gcgggtcgac gtctttgaga agatggcaa atattattgt    2820 gtccctatct atacaataga tatgatgaaa gggatcttgc caaacaaggc gatcgagccg    2880
aacaaaccgt actctgagtg gaaggaaatg acggaggact atacattccg attcagtcta    2940
tacccaaatg atcttatccg tatcgaattt ccccgagaaa aaacaataaa gactgctgtg    3000
ggggaagaaa tcaaaattaa ggatctgttc gcctattatc aaaccatcga ctcctccaat    3060
ggagggttaa gtttggttag ccatgataac aacttttcgc tccgcagcat cggttcaaga    3120
accctcaaac gattcgagaa ataccaagta gatgtgctag gcaacatcta caaagtgaga    3180
ggggaaaaga gagttggggt ggcgtcatct tctcattcga aagccgggga aactatccgt    3240
ccgttataa                                                            3249
```

<210> SEQ ID NO 8
<211> LENGTH: 1045
<212> TYPE: PRT
<213> ORGANISM: Actinomyces naeslundii

<400> SEQUENCE: 8

```
Met Trp Tyr Ala Ser Leu Met Ser Ala His His Leu Arg Val Gly Ile
1               5                   10                  15

Asp Val Gly Thr His Ser Val Gly Leu Ala Thr Leu Arg Val Asp Asp
            20                  25                  30

His Gly Thr Pro Ile Glu Leu Leu Ser Ala Leu Ser His Ile His Asp
        35                  40                  45

Ser Gly Val Gly Lys Glu Gly Lys Lys Asp His Asp Thr Arg Lys Lys
50                  55                  60

Leu Ser Gly Ile Ala Arg Arg Ala Arg Arg Leu Leu His His Arg Arg
65                  70                  75                  80

Thr Gln Leu Gln Gln Leu Asp Glu Val Leu Arg Asp Leu Gly Phe Pro
                85                  90                  95

Ile Pro Thr Pro Gly Glu Phe Leu Asp Leu Asn Glu Gln Thr Asp Pro
            100                 105                 110

Tyr Arg Val Trp Arg Val Arg Ala Arg Leu Val Glu Glu Lys Leu Pro
        115                 120                 125

Glu Glu Leu Arg Gly Pro Ala Ile Ser Met Ala Val Arg His Ile Ala
130                 135                 140

Arg His Arg Gly Trp Arg Asn Pro Tyr Ser Lys Val Glu Ser Leu Leu
145                 150                 155                 160

Ser Pro Ala Asn Ala Asn Glu Ile Arg Lys Ile Cys Ala Arg Gln Gly
                165                 170                 175

Val Ser Pro Asp Val Cys Lys Gln Leu Leu Arg Ala Val Phe Lys Ala
            180                 185                 190

Asp Ser Pro Arg Gly Ser Ala Val Ser Arg Val Ala Pro Asp Pro Leu
        195                 200                 205

Pro Gly Gln Gly Ser Phe Arg Arg Ala Pro Lys Cys Asp Pro Glu Phe
210                 215                 220

Gln Arg Phe Arg Ile Ile Ser Ile Val Ala Asn Leu Arg Ile Ser Glu
225                 230                 235                 240

Thr Lys Gly Glu Asn Arg Pro Leu Thr Ala Asp Glu Arg Arg His Val
                245                 250                 255

Val Thr Phe Leu Thr Glu Asp Ser Gln Ala Asp Leu Thr Trp Val Asp
            260                 265                 270

Val Ala Glu Lys Leu Gly Val His Arg Arg Asp Leu Arg Gly Thr Ala
        275                 280                 285

Val His Thr Asp Asp Gly Glu Arg Ser Ala Ala Arg Pro Pro Ile Asp
290                 295                 300

Ala Thr Asp Arg Ile Met Arg Gln Thr Lys Ile Ser Ser Leu Lys Thr
305                 310                 315                 320

Trp Trp Glu Glu Ala Asp Ser Glu Gln Arg Gly Ala Met Ile Arg Tyr
                325                 330                 335

Leu Tyr Glu Asp Pro Thr Asp Ser Glu Cys Ala Glu Ile Ile Ala Glu
            340                 345                 350

Leu Pro Glu Glu Asp Gln Ala Lys Leu Asp Ser Leu His Leu Pro Ala
        355                 360                 365

Gly Arg Ala Ala Tyr Ser Arg Glu Ser Leu Thr Ala Leu Ser Asp His
370                 375                 380

Met Leu Ala Thr Thr Asp Asp Leu His Glu Ala Arg Lys Arg Leu Phe
385                 390                 395                 400

Gly Val Asp Asp Ser Trp Ala Pro Pro Ala Glu Ala Ile Asn Ala Pro
                405                 410                 415
```

```
Val Gly Asn Pro Ser Val Asp Arg Thr Leu Lys Ile Val Gly Arg Tyr
            420                 425                 430

Leu Ser Ala Val Glu Ser Met Trp Gly Thr Pro Glu Val Ile His Val
            435                 440                 445

Glu His Val Arg Asp Gly Phe Thr Ser Glu Arg Met Ala Asp Glu Arg
            450                 455                 460

Asp Lys Ala Asn Arg Arg Arg Tyr Asn Asp Asn Gln Glu Ala Met Lys
465                 470                 475                 480

Lys Ile Gln Arg Asp Tyr Gly Lys Glu Gly Tyr Ile Ser Arg Gly Asp
                485                 490                 495

Ile Val Arg Leu Asp Ala Leu Glu Leu Gln Gly Cys Ala Cys Leu Tyr
                500                 505                 510

Cys Gly Thr Thr Ile Gly Tyr His Thr Cys Gln Leu Asp His Ile Val
            515                 520                 525

Pro Gln Ala Gly Pro Gly Ser Asn Asn Arg Arg Gly Asn Leu Val Ala
            530                 535                 540

Val Cys Glu Arg Cys Asn Arg Ser Lys Ser Asn Thr Pro Phe Ala Val
545                 550                 555                 560

Trp Ala Gln Lys Cys Gly Ile Pro His Val Gly Val Lys Glu Ala Ile
                565                 570                 575

Gly Arg Val Arg Gly Trp Arg Lys Gln Thr Pro Asn Thr Ser Ser Glu
            580                 585                 590

Asp Leu Thr Arg Leu Lys Lys Glu Val Ile Ala Arg Leu Arg Arg Thr
            595                 600                 605

Gln Glu Asp Pro Glu Ile Asp Glu Arg Ser Met Glu Ser Val Ala Trp
            610                 615                 620

Met Ala Asn Glu Leu His His Arg Ile Ala Ala Tyr Pro Glu Thr
625                 630                 635                 640

Thr Val Met Val Tyr Arg Gly Ser Ile Thr Ala Ala Arg Lys Ala
                645                 650                 655

Ala Gly Ile Asp Ser Arg Ile Asn Leu Ile Gly Glu Lys Gly Arg Lys
            660                 665                 670

Asp Arg Ile Asp Arg Arg His Ala Val Asp Ala Ser Val Val Ala
            675                 680                 685

Leu Met Glu Ala Ser Val Ala Lys Thr Leu Ala Glu Arg Ser Ser Leu
    690                 695                 700

Arg Gly Glu Gln Arg Leu Thr Gly Lys Glu Gln Thr Trp Lys Gln Tyr
705                 710                 715                 720

Thr Gly Ser Thr Val Gly Ala Arg Glu His Phe Glu Met Trp Arg Gly
                725                 730                 735

His Met Leu His Leu Thr Glu Leu Phe Asn Glu Arg Leu Ala Glu Asp
            740                 745                 750

Lys Val Tyr Val Thr Gln Asn Ile Arg Leu Arg Leu Ser Asp Gly Asn
            755                 760                 765

Ala His Thr Val Asn Pro Ser Lys Leu Val Ser His Arg Leu Gly Asp
            770                 775                 780

Gly Leu Thr Val Gln Gln Ile Asp Arg Ala Cys Thr Pro Ala Leu Trp
785                 790                 795                 800

Cys Ala Leu Thr Arg Glu Lys Asp Phe Asp Glu Lys Asn Gly Leu Pro
            805                 810                 815

Ala Arg Glu Asp Arg Ala Ile Arg Val His Gly His Glu Ile Lys Ser
            820                 825                 830
```

-continued

```
Ser Asp Tyr Ile Gln Val Phe Ser Lys Arg Lys Lys Thr Asp Ser Asp
            835                 840                 845

Arg Asp Glu Thr Pro Phe Gly Ala Ile Ala Val Arg Gly Gly Phe Val
850                 855                 860

Glu Ile Gly Pro Ser Ile His His Ala Arg Ile Tyr Arg Val Glu Gly
865                 870                 875                 880

Lys Lys Pro Val Tyr Ala Met Leu Arg Val Phe Thr His Asp Leu Leu
                885                 890                 895

Ser Gln Arg His Gly Asp Leu Phe Ser Ala Val Ile Pro Pro Gln Ser
            900                 905                 910

Ile Ser Met Arg Cys Ala Glu Pro Lys Leu Arg Lys Ala Ile Thr Thr
        915                 920                 925

Gly Asn Ala Thr Tyr Leu Gly Trp Val Val Gly Asp Glu Leu Glu
    930                 935                 940

Ile Asn Val Asp Ser Phe Thr Lys Tyr Ala Ile Gly Arg Phe Leu Glu
945                 950                 955                 960

Asp Phe Pro Asn Thr Thr Arg Trp Arg Ile Cys Gly Tyr Asp Thr Asn
                965                 970                 975

Ser Lys Leu Thr Leu Lys Pro Ile Val Leu Ala Ala Glu Gly Leu Glu
            980                 985                 990

Asn Pro Ser Ser Ala Val Asn Glu Ile Val Glu Leu Lys Gly Trp Arg
        995                 1000                1005

Val Ala Ile Asn Val Leu Thr Lys Val His Pro Thr Val Val Arg
    1010                1015                1020

Arg Asp Ala Leu Gly Arg Pro Arg Tyr Ser Ser Arg Ser Asn Leu
    1025                1030                1035

Pro Thr Ser Trp Thr Ile Glu
    1040                1045

<210> SEQ ID NO 9
<211> LENGTH: 1160
<212> TYPE: PRT
<213> ORGANISM: Streptococcus pyogenes

<400> SEQUENCE: 9

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160
```

```
Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Arg
            180                 185                 190

Lys Gln Arg Thr Phe Asp Asn Gly Ser Ile Pro His Gln Ile His Leu
        195                 200                 205

Gly Glu Leu His Ala Ile Leu Arg Arg Gln Glu Asp Phe Tyr Pro Phe
    210                 215                 220

Leu Lys Asp Asn Arg Glu Lys Ile Glu Lys Ile Leu Thr Phe Arg Ile
225                 230                 235                 240

Pro Tyr Tyr Val Gly Pro Leu Ala Arg Gly Asn Ser Arg Phe Ala Trp
                245                 250                 255

Met Thr Arg Lys Ser Glu Glu Thr Ile Thr Pro Trp Asn Phe Glu Glu
            260                 265                 270

Val Val Asp Lys Gly Ala Ser Ala Gln Ser Phe Ile Glu Arg Met Thr
        275                 280                 285

Asn Phe Asp Lys Asn Leu Pro Asn Glu Lys Val Leu Pro Lys His Ser
    290                 295                 300

Leu Leu Tyr Glu Tyr Phe Thr Val Tyr Asn Glu Leu Thr Lys Val Lys
305                 310                 315                 320

Tyr Val Thr Glu Gly Met Arg Lys Pro Ala Phe Leu Ser Gly Glu Gln
                325                 330                 335

Lys Lys Ala Ile Val Asp Leu Leu Phe Lys Thr Asn Arg Lys Val Thr
            340                 345                 350

Val Lys Gln Leu Lys Glu Asp Tyr Phe Lys Lys Ile Glu Cys Phe Asp
        355                 360                 365

Ser Val Glu Ile Ser Gly Val Glu Asp Arg Phe Asn Ala Ser Leu Gly
    370                 375                 380

Thr Tyr His Asp Leu Leu Lys Ile Ile Lys Asp Lys Asp Phe Leu Asp
385                 390                 395                 400

Asn Glu Glu Asn Glu Asp Ile Leu Glu Asp Ile Val Leu Thr Leu Thr
                405                 410                 415

Leu Phe Glu Asp Arg Glu Met Ile Glu Glu Arg Leu Lys Thr Tyr Ala
            420                 425                 430

His Leu Phe Asp Asp Lys Val Met Lys Gln Leu Lys Arg Arg Arg Tyr
        435                 440                 445

Thr Gly Trp Gly Arg Leu Ser Arg Lys Leu Ile Asn Gly Ile Arg Asp
    450                 455                 460

Lys Gln Ser Gly Lys Thr Ile Leu Asp Phe Leu Lys Ser Asp Gly Phe
465                 470                 475                 480

Ala Asn Arg Asn Phe Met Gln Leu Ile His Asp Asp Ser Leu Thr Phe
                485                 490                 495

Lys Glu Asp Ile Gln Lys Ala Gln Val Ser Gly Gln Gly Asp Ser Leu
            500                 505                 510

His Glu His Ile Ala Asn Leu Ala Gly Ser Pro Ala Ile Lys Lys Gly
        515                 520                 525

Ile Leu Gln Thr Val Lys Val Val Asp Glu Leu Val Lys Val Met Gly
    530                 535                 540

Arg His Lys Pro Glu Asn Ile Val Ile Glu Met Ala Arg Glu Asn Gln
545                 550                 555                 560

Thr Thr Gln Lys Gly Gln Lys Asn Ser Arg Glu Arg Met Lys Arg Ile
                565                 570                 575
```

-continued

Glu Glu Gly Ile Lys Glu Leu Gly Ser Gln Ile Leu Lys Glu His Pro
                580                 585                 590

Val Glu Asn Thr Gln Leu Gln Asn Glu Lys Leu Tyr Leu Tyr Tyr Leu
            595                 600                 605

Gln Asn Gly Arg Asp Met Tyr Val Asp Gln Glu Leu Asp Ile Asn Arg
        610                 615                 620

Leu Ser Asp Tyr Asp Val Asp His Ile Val Pro Gln Ser Phe Leu Lys
625                 630                 635                 640

Asp Asp Ser Ile Asp Asn Lys Val Leu Thr Arg Ser Asp Lys Asn Arg
                645                 650                 655

Gly Lys Ser Asp Asn Val Pro Ser Glu Glu Val Val Lys Lys Met Lys
            660                 665                 670

Asn Tyr Trp Arg Gln Leu Leu Asn Ala Lys Leu Ile Thr Gln Arg Lys
        675                 680                 685

Phe Asp Asn Leu Thr Lys Ala Glu Arg Gly Gly Leu Ser Glu Leu Asp
690                 695                 700

Lys Ala Gly Phe Ile Lys Arg Gln Leu Val Glu Thr Arg Gln Ile Thr
705                 710                 715                 720

Lys His Val Ala Gln Ile Leu Asp Ser Arg Met Asn Thr Lys Tyr Asp
                725                 730                 735

Glu Asn Asp Lys Leu Ile Arg Glu Val Lys Val Ile Thr Leu Lys Ser
            740                 745                 750

Lys Leu Val Ser Asp Phe Arg Lys Asp Phe Gln Phe Tyr Lys Val Arg
        755                 760                 765

Glu Ile Asn Asn Tyr His His Ala His Asp Ala Tyr Leu Asn Ala Val
770                 775                 780

Val Gly Thr Ala Leu Ile Lys Lys Tyr Pro Lys Leu Glu Ser Glu Phe
785                 790                 795                 800

Val Tyr Gly Asp Tyr Lys Val Tyr Asp Val Arg Lys Met Ile Ala Lys
                805                 810                 815

Ser Glu Gln Glu Ile Gly Lys Ala Thr Ala Lys Tyr Phe Phe Tyr Ser
            820                 825                 830

Asn Ile Met Asn Phe Phe Lys Thr Glu Ile Thr Leu Ala Asn Gly Glu
        835                 840                 845

Ile Arg Lys Arg Pro Leu Ile Glu Thr Asn Gly Glu Thr Gly Glu Ile
850                 855                 860

Val Trp Asp Lys Gly Arg Asp Phe Ala Thr Val Arg Lys Val Leu Ser
865                 870                 875                 880

Met Pro Gln Val Asn Ile Val Lys Lys Thr Glu Val Gln Thr Gly Gly
                885                 890                 895

Phe Ser Lys Glu Ser Ile Leu Pro Lys Arg Asn Ser Asp Lys Leu Ile
            900                 905                 910

Ala Arg Lys Lys Asp Trp Asp Pro Lys Lys Tyr Gly Gly Phe Asp Ser
        915                 920                 925

Pro Thr Val Ala Tyr Ser Val Leu Val Val Ala Lys Val Glu Lys Gly
930                 935                 940

Lys Ser Lys Lys Leu Lys Ser Val Lys Glu Leu Leu Gly Ile Thr Ile
945                 950                 955                 960

Met Glu Arg Ser Ser Phe Glu Lys Asn Pro Ile Asp Phe Leu Glu Ala
                965                 970                 975

Lys Gly Tyr Lys Glu Val Lys Lys Asp Leu Ile Ile Lys Leu Pro Lys
            980                 985                 990

Tyr Ser Leu Phe Glu Leu Glu Asn  Gly Arg Lys Arg Met  Leu Ala Ser

```
            995                 1000                1005
Ala Gly Glu Leu Gln Lys Gly Asn Glu Leu Ala Leu Pro Ser Lys
    1010                1015                1020

Tyr Val Asn Phe Leu Tyr Leu Ala Ser His Tyr Glu Lys Leu Lys
    1025                1030                1035

Gly Ser Pro Glu Asp Asn Glu Gln Lys Gln Leu Phe Val Glu Gln
    1040                1045                1050

His Lys His Tyr Leu Asp Glu Ile Ile Glu Gln Ile Ser Glu Phe
    1055                1060                1065

Ser Lys Arg Val Ile Leu Ala Asp Ala Asn Leu Asp Lys Val Leu
    1070                1075                1080

Ser Ala Tyr Asn Lys His Arg Asp Lys Pro Ile Arg Glu Gln Ala
    1085                1090                1095

Glu Asn Ile Ile His Leu Phe Thr Leu Thr Asn Leu Gly Ala Pro
    1100                1105                1110

Ala Ala Phe Lys Tyr Phe Asp Thr Thr Ile Asp Arg Lys Arg Tyr
    1115                1120                1125

Thr Ser Thr Lys Glu Val Leu Asp Ala Thr Leu Ile His Gln Ser
    1130                1135                1140

Ile Thr Gly Leu Tyr Glu Thr Arg Ile Asp Leu Ser Gln Leu Gly
    1145                1150                1155

Gly Asp
    1160

<210> SEQ ID NO 10
<211> LENGTH: 8
<212> TYPE: DNA
<213> ORGANISM: Artificial sequence
<220> FEATURE:
<223> OTHER INFORMATION: RNA, DNA or synthetic nucleic acid consensus
      PAM sequence
<220> FEATURE:
<221> NAME/KEY: misc_feature
<222> LOCATION: (7)..(7)
<223> OTHER INFORMATION: n is a, c, g, t or u

<400> SEQUENCE: 10 ccccccna                                                                8

<210> SEQ ID NO 11
<211> LENGTH: 8
<212> TYPE: DNA
<213> ORGANISM: Artificial sequence
<220> FEATURE:
<223> OTHER INFORMATION: DNA PAM sequence

<400> SEQUENCE: 11 ccccccaa                                                                8

<210> SEQ ID NO 12
<211> LENGTH: 5
<212> TYPE: DNA
<213> ORGANISM: Artificial sequence
<220> FEATURE:
<223> OTHER INFORMATION: DNA PAM sequence

<400> SEQUENCE: 12 ccccc                                                                   5

<210> SEQ ID NO 13
<211> LENGTH: 8
```

```
<212> TYPE: DNA
<213> ORGANISM: Artificial sequence
<220> FEATURE:
<223> OTHER INFORMATION: RNA, DNA or synthetic nucleic acid consensus
      PAM sequence
<220> FEATURE:
<221> NAME/KEY: misc_feature
<222> LOCATION: (6)..(7)
<223> OTHER INFORMATION: n is a, c, g, t or u

<400> SEQUENCE: 13 cccccnna                                                                 8

<210> SEQ ID NO 14
<211> LENGTH: 6
<212> TYPE: DNA
<213> ORGANISM: Artificial sequence
<220> FEATURE:
<223> OTHER INFORMATION: DNA PAM sequence

<400> SEQUENCE: 14 cccccc                                                                   6

<210> SEQ ID NO 15
<211> LENGTH: 6
<212> TYPE: DNA
<213> ORGANISM: Artificial sequence
<220> FEATURE:
<223> OTHER INFORMATION: RNA, DNA or synthetic nucleic acid consensus
      PAM sequence
<220> FEATURE:
<221> NAME/KEY: misc_feature
<222> LOCATION: (1)..(1)
<223> OTHER INFORMATION: n is a, c, g, t or u

<400> SEQUENCE: 15 ncccccc                                                                  6

<210> SEQ ID NO 16
<211> LENGTH: 8
<212> TYPE: DNA
<213> ORGANISM: Artificial sequence
<220> FEATURE:
<223> OTHER INFORMATION: RNA, DNA or synthetic nucleic acid consensus
      PAM sequence
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (7)..(7)
<223> OTHER INFORMATION: n is a, c, g, t or u

<400> SEQUENCE: 16 nccccccna                                                                8

<210> SEQ ID NO 17
<211> LENGTH: 8
<212> TYPE: DNA
<213> ORGANISM: Artificial sequence
<220> FEATURE:
<223> OTHER INFORMATION: RNA, DNA or synthetic nucleic acid consensus
      PAM sequence
<220> FEATURE:
<221> NAME/KEY: misc_feature
<222> LOCATION: (2)..(2)
<223> OTHER INFORMATION: n is a, c, g, t or u

<400> SEQUENCE: 17
```

-continued cnccccac                                                               8

<210> SEQ ID NO 18
<211> LENGTH: 8
<212> TYPE: DNA
<213> ORGANISM: Artificial sequence
<220> FEATURE:
<223> OTHER INFORMATION: DNA PAM sequence

<400> SEQUENCE: 18 cccccag                                                                8

<210> SEQ ID NO 19
<211> LENGTH: 8
<212> TYPE: DNA
<213> ORGANISM: Artificial sequence
<220> FEATURE:
<223> OTHER INFORMATION: DNA PAM sequence

<400> SEQUENCE: 19 ccccccat                                                               8

<210> SEQ ID NO 20
<211> LENGTH: 8
<212> TYPE: DNA
<213> ORGANISM: Artificial sequence
<220> FEATURE:
<223> OTHER INFORMATION: DNA PAM sequence

<400> SEQUENCE: 20 ccccccac                                                               8

<210> SEQ ID NO 21
<211> LENGTH: 8
<212> TYPE: DNA
<213> ORGANISM: Bacillus smithii ET138

<400> SEQUENCE: 21 atccccaa                                                               8

<210> SEQ ID NO 22
<211> LENGTH: 8
<212> TYPE: DNA
<213> ORGANISM: Bacillus smithii ET138

<400> SEQUENCE: 22 acggccaa                                                               8

<210> SEQ ID NO 23
<211> LENGTH: 325
<212> TYPE: DNA
<213> ORGANISM: Artificial Sequence
<220> FEATURE:
<223> OTHER INFORMATION: Chemically Synthesized, tracrRNA t12

<400> SEQUENCE: 23
attgttttcc cctcccatgc acaatagttt tatagtaaaa aagaccttga cgttttccgc       60
caaggtcttc gttcgcctaa gagtggggaa tgcccgaaga aagcgggcga taggcgatcc     120
ccaacgccac gggtcagtct gcctataggc agaaagccct tatcatagta accctgagat     180
cattgctgtg gtataaccct attactataa taatgtttat atttgggaaa atcaagtcct     240
ttttctatat ttttatact ttcatttctt cttgcattat gatgatgtga gggaggatag      300
atttctgaca ggaggtttca catcg                                           325

```
<210> SEQ ID NO 24
<211> LENGTH: 36
<212> TYPE: DNA
<213> ORGANISM: Artificial Sequence
<220> FEATURE:
<223> OTHER INFORMATION: Chemically synthesized, repeat gb

<400> SEQUENCE: 24
gtcatagttc ccctgagatt atcgctgtgg tataat                              36

<210> SEQ ID NO 25
<211> LENGTH: 30
<212> TYPE: RNA
<213> ORGANISM: Artificial Sequence
<220> FEATURE:
<223> OTHER INFORMATION: Chemically synthesized, Crispr RNA

<400> SEQUENCE: 25
uuggcggugc gaauucuaac cgucccggaa                                      30

<210> SEQ ID NO 26
<211> LENGTH: 46
<212> TYPE: DNA
<213> ORGANISM: Geobacillus virus E2

<400> SEQUENCE: 26
tgtggtgctt ccgggacggt tagaattcgc accgccaaca tgcgat                   46

<210> SEQ ID NO 27
<211> LENGTH: 46
<212> TYPE: DNA
<213> ORGANISM: Geobacillus virus E2

<400> SEQUENCE: 27
atcgcatgtt ggcggtgcga attctaaccg tcccggaagc accaca                   46

<210> SEQ ID NO 28
<211> LENGTH: 30
<212> TYPE: RNA
<213> ORGANISM: Artificial Sequence
<220> FEATURE:
<223> OTHER INFORMATION: Chemically synthesized, Crispr RNA

<400> SEQUENCE: 28
uucuaccucu acucucgauu cacgaaucgg                                      30

<210> SEQ ID NO 29
<211> LENGTH: 46
<212> TYPE: DNA
<213> ORGANISM: Bacillus alveayuensis strain 24KAM51 LG50_053

<400> SEQUENCE: 29
ttggaaaacc gattcgtgaa tcgagagtag aggtagaaag agcagc                   46

<210> SEQ ID NO 30
<211> LENGTH: 46
<212> TYPE: DNA
<213> ORGANISM: Bacillus alveayuensis strain 24KAM51 LG50_053

<400> SEQUENCE: 30
gctgctcttt ctacctctac tctcgattca cgaatcggtt ttccaa                   46

<210> SEQ ID NO 31
```

```
<211> LENGTH: 29
<212> TYPE: RNA
<213> ORGANISM: Artificial Sequence
<220> FEATURE:
<223> OTHER INFORMATION: Chemically synthesized, Crispr RNA

<400> SEQUENCE: 31
ucacggagcu uuacacaaau aaagccgga                                    29

<210> SEQ ID NO 32
<211> LENGTH: 45
<212> TYPE: DNA
<213> ORGANISM: Anoxybacillus flavithermus WK1

<400> SEQUENCE: 32
ttcgtcgctc cggctttatt tgtgtaaagc tccgtgatct tgtag                  45

<210> SEQ ID NO 33
<211> LENGTH: 45
<212> TYPE: DNA
<213> ORGANISM: Anoxybacillus flavithermus WK1

<400> SEQUENCE: 33
ctacaagatc acggagcttt acacaaataa agccggagcg acgaa                  45

<210> SEQ ID NO 34
<211> LENGTH: 29
<212> TYPE: RNA
<213> ORGANISM: Artificial Sequence
<220> FEATURE:
<223> OTHER INFORMATION: Chemically synthesized, Crispr RNA

<400> SEQUENCE: 34
ucacggagcu uuacacaaau aaagccgga                                    29

<210> SEQ ID NO 35
<211> LENGTH: 45
<212> TYPE: DNA
<213> ORGANISM: Geobacillus kaustophilus strain Et23 LG51_086

<400> SEQUENCE: 35
ttcgttgctc cggctttatt tgtgtaaagc tccgtgatct tgtac                  45

<210> SEQ ID NO 36
<211> LENGTH: 45
<212> TYPE: DNA
<213> ORGANISM: Geobacillus kaustophilus strain Et23 LG51_086

<400> SEQUENCE: 36
gtacaagatc acggagcttt acacaaataa agccggagca acgaa                  45

<210> SEQ ID NO 37
<211> LENGTH: 30
<212> TYPE: RNA
<213> ORGANISM: Artificial Sequence
<220> FEATURE:
<223> OTHER INFORMATION: Chemically synthesized, Crispr RNA

<400> SEQUENCE: 37
caacaccuuc cgcgcugucu cgucuacuuu                                   30

<210> SEQ ID NO 38
<211> LENGTH: 46
<212> TYPE: DNA
<213> ORGANISM: Geobacillus virus E2
```

```
<400> SEQUENCE: 38
ttcgtaaaaa agtagatgag acagcacgga aggtgttgaa agaagc            46

<210> SEQ ID NO 39
<211> LENGTH: 46
<212> TYPE: DNA
<213> ORGANISM: Geobacillus virus E2

<400> SEQUENCE: 39
gcttctttca acaccttccg tgctgtctca tctactttt tacgaa             46

<210> SEQ ID NO 40
<211> LENGTH: 30
<212> TYPE: RNA
<213> ORGANISM: Artificial Sequence
<220> FEATURE:
<223> OTHER INFORMATION: Chemically synthesized, Crispr RNA

<400> SEQUENCE: 40
uugauuagca auuugacuug ggaauuuagc                              30

<210> SEQ ID NO 41
<211> LENGTH: 46
<212> TYPE: DNA
<213> ORGANISM: Pasteurella bettyae

<400> SEQUENCE: 41
ttggcattac taaattccgc agtcaaattg ctaatcaaat gttaat            46

<210> SEQ ID NO 42
<211> LENGTH: 46
<212> TYPE: DNA
<213> ORGANISM: Pasteurella bettyae

<400> SEQUENCE: 42
attaacattt gattagcaat ttgactgcgg aatttagtaa tgccaa            46
```